US006828420B2

(12) United States Patent
Adelman et al.

(10) Patent No.: US 6,828,420 B2
(45) Date of Patent: Dec. 7, 2004

(54) SMALL CONDUCTANCE, CALCIUM-ACTIVATED POTASSIUM CHANNELS (SKI)

(75) Inventors: John P. Adelman, Portland, OR (US); James Maylie, Portland, OR (US); Chris T. Bond, Portland, OR (US); Christopher P. Silvia, Durham, NC (US)

(73) Assignees: Oregon Health Sciences University, Portland, OR (US); Icagen, Inc., Durham, NC (US)

(*) Notice: Subject to any disclaimer, the term of this patent is extended or adjusted under 35 U.S.C. 154(b) by 416 days.

(21) Appl. No.: 10/115,671

(22) Filed: Apr. 3, 2002

(65) Prior Publication Data

US 2003/0044910 A1 Mar. 6, 2003

Related U.S. Application Data

(62) Division of application No. 09/254,590, filed as application No. PCT/US97/16033 on May 24, 1999.
(60) Provisional application No. 60/045,233, filed on Apr. 17, 1997, provisional application No. 60/040,052, filed on Mar. 7, 1997, and provisional application No. 60/026,451, filed on Sep. 11, 1996.

(51) Int. Cl.[7] ........................ C07K 14/00; C07K 14/705
(52) U.S. Cl. ........................................................ 530/350
(58) Field of Search ........................................ 530/350

(56) References Cited

U.S. PATENT DOCUMENTS 6,277,978 B1 * 8/2001 Keating et al. ............. 536/23.5

FOREIGN PATENT DOCUMENTS

| EP | 0 614 977 A2 | 3/1994 |
|---|---|---|
| EP | WO 99 03889 | 1/1999 |
| WO | WO 89/0979 | 10/1989 |
| WO | WO 95/21252 | 8/1995 |
| WO | WO 99/03882 | 1/1999 |
| WO | WO 99/03889 | 1/1999 |
| WO | WO 99/25347 | 5/1999 |

OTHER PUBLICATIONS

Database EMBL 'Online!, (Oct. 4, 1996) Database accession No. U69883, XP002212554, the whole document.
Database EMBL 'Online!, (Oct. 4, 1996) Database accession No. U69884, XP002212555, the whole document.
Database EMBL. 'Online!, (Oct 4, 1996) Database accession No. U69882, XP002212558, the whole document.
Database Swissprot 'Online!, (Nov. 1, 1996), Database accession No. Q19186, XP002212558, the whole document.
McCobb D P et al.: "A Human Calcium–Activated Potassium Channel Gene Expressed in Vascular Smooth Muscle", American Journal of Physiology: Heart and Circulatory Physiology, The American Physiological Society, XX, vol. 269, NR. 3, page(s) H767–H777 XP002924141, ISSN: 0363–6135.
Kohler et al., Small–Conductance, Calcium–Activated Potassium Channels for Mammalian Brian, *Science*, 273:1709–1714 (9/96).

* cited by examiner

*Primary Examiner*—Michael Pak
(74) *Attorney, Agent, or Firm*—Townsend and Townsend and Crew LLP

(57) ABSTRACT

This invention relates to small and intermediate conductance, calcium-activated potassium channel proteins. More specifically, the invention relates to compositions and methods for making and detecting calcium-activated potassium channel proteins and the nucleic acids encoding calcium-activated potassium channel proteins. The invention also provides methods and compositions for assaying compounds which increase or decrease potassium ion flux through a calcium-activated potassium channel.

4 Claims, No Drawings

SMALL CONDUCTANCE, CALCIUM-ACTIVATED POTASSIUM CHANNELS (SK)

CROSS-REFERENCES TO RELATED APPLICATIONS

This application is a divisional of U.S. Ser. No. 09/254,590, filed May 24, 1999, which is a 35 USC § 371 U.S. national phase of PCT application PCT/US97/16033, filed Sep. 10, 1997, the disclosure of which is herein incorporated by reference in its entirety, which claims the benefit of the filing date of U.S. Ser. No. 60/026,451, filed on Sep. 11, 1996; U.S. Ser. No. 60/040,052, filed on Mar. 7, 1997; and U.S. Ser. No. 60/045,233, filed on Apr. 17, 1997.

STATEMENT AS TO RIGHTS TO INVENTIONS MADE UNDER FEDERALLY SPONSORED RESEARCH OR DEVELOPMENT

This invention was made with United States Government support under Grant No. 1R01NS31872-01A1, awarded by the National Institutes of Health. The United States Government has certain rights in this invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Field of the Invention

The present invention relates to compositions relating to, and methods for identifying, small conductance (SK) and intermediate conductance (IK), calcium-activated potassium channels. The invention further provides a method to assay for compounds that increase or decrease potassium ion flux through calcium-activated potassium channels.

Calcium-activated potassium currents are found in a wide variety of animal cells such as nervous, muscular, glandular or epithelial tissue and from the immune system. The channels regulating these currents open and allow the escape of potassium as the internal calcium concentration increases. This outward flow of potassium ions makes the interior of the cell more negative, counteracting depolarizing voltages applied to the cell.

Two distinct classes of calcium-activated K$^+$ channels ($K_{ca}$ channels) have been described. Large conductance calcium-activated K$^+$ channels (BK channels) are gated by the concerted actions of internal calcium ions and membrane potential, and have a unit conductance between 100 and 220 pS. Small (SK) and intermediate (IK) conductance calcium-activated K$^+$ channels are gated solely by internal calcium ions, with a unit conductance of 2–20 and 20–85 pS, respectively, and are more sensitive to calcium than are BK channels (for review see Latorre et al., 1989, *Ann Rev Phys*, 51, 385–399.). In addition, each type of $K_{Ca}$ channel shows a distinct pharmacological profile. All three classes are widely expressed, and their activity hyperpolarizes the membrane potential. Members of the BK (Atkinson et al., 1991, *Science*, 253, 551–555.; Adelman et al., 1992 *Neuron*, 9, 209–216.; Butler, 1993, *Science*, 261, 221–224) and SK (Kohler et al., 1996, *Science*, 273, 1709–1714.) subfamilies have been cloned and expressed in heterologous cell types where they recapitulate the fundamental properties of their native counterparts.

In vertebrate neurons action potentials are followed by an afterhyperpolarization (AHP) that may persist for several seconds and have profound consequences for the firing pattern of the neuron. Alterations in the AHP have been implicated in seizure activity (Alger et al., J. Physiol. 399:191–205 (1988)) and learning and memory (de Jonge et al., *Exp. Br. Res.* 80:456–462 (1990)). The AHP is composed of two prominent components, a fast component (fAHP) which mediates spike frequency at the onset of a burst, and a subsequent slow component (sABP) which is responsible for spike-frequency adaptation (Nicoll, *Science* 241:545–551 (1988)).

Each component of the AHP is kinetically distinct and is due to activation of different calcium-activated potassium channels. Activation of large-conductance (100–200 picoSiemens (pS)), voltage- and calcium-activated potassium channels (BK channels) underlies the fAHP (Lancaster et al, *J. Physiol.* 389:187–203 (1987); Viana et al., *J. Neurophysiol.* 69:2150–2163 (1993)) which develops rapidly (1–2 ms) and decays within tens of milliseconds. The channels underlying the sAHP are small conductance, calcium activated, potassium channels (SK channels) which differ from BK channels, being more calcium-sensitive, are not voltage-gated, and possessing a smaller unit conductance (Lancaster et al., *J. Neurosci.* 11:23–30 (1991); Sah, *J. Neurophysiol.* 74:1772–1776 (1995)).

The fAHP and the sAHP also differ in their pharmacology. The fAHP is blocked by low concentrations of external tetraethylammonium (TEA) and charybdotoxin (CTX), in accord with the pharmacology of the BK channels. Lancaster et al. *J. Physiol.* 389:187–203 (1987); Viana et al., *J. Neurophysiol.* 69:2150–2163 (1993); Butler et al., *Science* 261:221–224 (1993). In contrast, the sAHP is insensitive to CTX, but fall into two classes regarding sensitivity to the bee venom peptide toxin, apamin. For example, in hippocampal pyramidal neurons, the sAHP is insensitive to apamin (Lancaster et al., *J. Neurophysiol.* 55:1268–1282 (1986)), while in hippocampal interneurons and vagal neurons it is blocked by nanomolar concentrations of the toxin (Sah, *J. Neurophysiol.* 74:1772–1776 (1995); Zhang et al., *J. Physiol.* 488:661–672 (1995)).

In addition to its role in neuronal cells, non-voltage gated, apamin-sensitive potassium channels activated by submicromolar concentrations of calcium have also been described from peripheral cell types, including skeletal muscle (Blatz et al., *Nature* 323:718–720 (1986)), gland cells (Tse et al., *Science* 255:462–464 (1992); Park, *J. Physiol.* 481:555–570 (1994)) and T-lymphocytes (Grissmer et al., *J. Gen. Physiol.* 99:63–84 (1992)).

For example, SK channels have been suggested to represent the apamin receptor found in muscle membrane of patients with myotonic muscular dystrophy. Renaud et al., *Nature* 319:678–680 (1986)). Also, Grissmer et al. (*J. Gen. Physiol.* 99:63–84 (1992)) report that CTX insensitive, apamin sensitive calcium-activated potassium channels were identified in a human leukemic T cell line and suggest that calcium-activated potassium channels play a supporting role during T-cell activation by sustaining dynamic patterns of calcium signaling. And in many cells, SK channels are activated as a result of neurotransmitter or hormone action. Haylett et al., in *Potassium Channels: Structure, Classification, Function and Therapeutic Potential* (Cook, N. S., ed.), pp.71–95, John Wiley and Sons, 1990). Intermediate channels play a role in the physiology of red blood cells.

Intermediate conductance, calcium activated potassium channels have been previously described in the literature by their electrophysiology. The Gardos channel is opened by submicromolar concentrations of internal calcium and has a rectifying unit conductance, ranging from 50 pS at −120 mV to 13 pS at 120 mV (symmetrical 120 mM $K^+$; Christophersen, 1991, *J. Membrane Biol.*, 119, 75–83.). It is blocked by charybdotoxin (CTX) but not the structurally related peptide iberiotoxin (IBX), both of which block BK channels (Brugnara et al., 1995a, *J. Membr. Biol.*, 147, 71–82). Apamin, a potent blocker of certain native (Vincent et al., 1975, *J. Biochem.*, 14, 2521.; Blatz and Magleby, 1986, *Nature*, 323, 718–720.) and cloned SK channels do not block IK channels (de-Allie et al., 1996, *Br. J. Pharm.*, 117,479–487). The Gardos channel is also blocked by some imidazole compounds, such as clotrimazole, but not ketoconazole (Brugnara et al., 1993, *J. Clin. Invest.*, 92,520–526). The electrophysiological and pharmacological properties of the Gardos channel show that it belongs to the IK subfamily of this invention.

IK channels have been described in a variety of other cell types. Principle cells of the rat cortical collecting duct segregate different classes of $K^+$ channels to the luminal and basolateral membranes. IK channels are present in the basolateral membrane where they promote the recirculation of $K^+$ across this membrane, elevating the activity of the $Na^++K^+$-ATPase and thereby $Na^+$ reabsorption into the blood (Hirsch and Schlatter, 1995, *Pflügers Arch.—Eur. J. Physiol.*, 449, 338–344.) IK channels have also been implicated in the microvasculature of the kidney where they may be responsible for the vasodilatory effects of bradykinin (Rapacon et al., 1996). In brain capillary endothelial cells, IK channels are activated by endothelin, produced by neurons and glia, shunting excess $K^+$ into the blood (Renterghem et al., 1995, *J. Neurochem.*, 65, 1274–1281). Neutrophil granulocytes, mobile phagocytic cells which defend against microbial invaders, undergo a large depolarization subsequent to agonist stimulation, and IK channels have been implicated in repolarizing the stimulated granulocyte (Varnai et al., 1993, *J. Physiol.*, 472, 373–390.). IK channels have also been identified in both resting and activated human T-lymphocytes. Grissmer et al. 1993, *J. Gen. Physiol.* 102,601–630 reported that IK channels were blocked by low nanomolar concentrations of charybdotoxin, showed little or no voltage dependence, and were insensitive to apamin. This channel has also been identified in human erythrocytes, where it plays an important role in intracellular volume homeostasis (Joiner, C. H., 1993, *Am. J. Physiol.* 264: C251–270 and in smooth muscle (Van Renterghem, C. et al. 1996, *J. Neurochemistry* 65,1274–1281.

Thus, it appears that SK and IK channels comprise a subfamily of calcium-activated potassium channels which play key physiological roles in many cell types. Accordingly, given the key role of SK and IK channels in a wide variety of physiological functions, what is needed in the art is the identification of novel SK and IK channel proteins and the nucleic acids encoding them. Additionally, what is needed are methods of identifying compounds which increase or decrease SK and IK channel currents for their use in the treatment or regulation of: learning and memory disorders, seizures, myotonic dystrophies, immune responses, and neurotransmitter or hormone secretions. The present invention provides these and other advantages.

SUMMARY OF THE INVENTION

In a first broad context, this invention provides for novel proteins and their corresponding nucleic acids where the proteins are defined as monomers of calcium activated potassium ion channels. The monomers have a molecular weight of between 40 and 80 kDa and have units of conductance of between 2 and 80 pS when the monomer is in the polymeric form as expressed in *Xenopus* oocytes. In addition, the monomer specifically binds to antibodies generated against SEQ ID NO:30 or 42.

In another aspect, the present invention relates to an isolated nucleic acid encoding at least 15 contiguous amino acids of a calcium-activated potassium channel protein. The SK channel protein has a sequence selected from the group consisting of SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47 and conservatively modified variants of SEQ ID NOS:1, 2, 3, 4, 19, 20, 32, 43 or 47.

In some embodiments, the isolated nucleic acid encodes a calcium-activated potassium channel protein having a conductance of at least 2 pS when expressed in a *Xenopus* oocyte, a molecular weight of between 40 and 100 kilodaltons (kd), and selectively hybridizes, under stringent hybridization conditions, with SK or IK encoding nucleic acid such as SEQ ID NO:13 in a human genomic library or SEQ ID NO:14 in a rat genomic library. In other embodiments, the isolated nucleic acid encoding the calcium-activated potassium channel, protein encodes a protein having a sequence selected from the group consisting of: SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47. In preferred embodiments the nucleic acid has a sequence selected from the group consisting of: SEQ ID NO:13, SEQ ID NO:14, SEQ ID NO:15, SEQ ID NO:16, SEQ ID NO:21, SEQ ID NO:22, SEQ ID NO:31, SEQ ID NO:44, and SEQ ID NO:48.

In another aspect, the present invention relates to an isolated calcium-activated potassium channel protein having at least 15 contiguous amino acids of a sequence selected from the group consisting of: SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47, and conservatively modified variants of SEQ ID NOS:1, 2, 3, 4, 19, 20, 32, 43, or 47, wherein the variant specifically reacts, under immunologically reactive conditions, with an antibody reactive to a protein selected from the group consisting of: SEQ ID NO:1, SEQ ID NO:2, SEQ ID NO:3, SEQ ID NO:4, SEQ ID NO:19, SEQ ID NO:20, SEQ ID NO:30, SEQ ID NO:32, SEQ ID NO:43, and SEQ ID NO:47.

In a broad embodiment, the calcium-activated potassium channel protein is defined as having a conductance of at least 2 pS and a molecular weight of between 40 and 100 Kd. In other embodiments, the calcium-activated potassium channel protein has an amino acid sequence selected from the group consisting of: SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47.

In another aspect, the present invention is directed to an antibody specifically reactive, under immunologically reactive conditions, to a calcium-activated potassium channel protein, where the protein has a sequence selected from the group consisting of: SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47. In preferred embodiments, the antibody is limited to a monoclonal antibody.

In yet another aspect, the present invention relates to an expression vector comprising a nucleic acid encoding a monomer of a calcium-activated potassium channel where the monomer has a sequence selected from the group consisting of SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47, and conservatively modified variants of SEQ ID NOS:1, 2, 3, 4, 19, 20, 32, 43, or 47 wherein the modified variant is a protein having a conductance of at least 2 pS when expressed in a Xenopus oocyte, a molecular weight of between 40 and 100 kd, and specifically reacts, under immunologically reactive conditions, with an antibody reactive to a full-length protein selected from the group consisting of: SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47.

In another aspect, the present invention relates to a host cell transfected with a vector comprising a nucleic acid encoding a monomer of a calcium-activated potassium channel protein where the protein has a sequence selected from the group consisting of SEQ ID NO:1, SEQ ID NO:2, SEQ ID NO:3, SEQ ID NO:19, SEQ ID NO:20, SEQ ID NO:32, SEQ ID NO:43, SEQ ID NO:47, and conservatively modified variants of SEQ ID NO:1, 2, 3, 4, 19, 20, 32, 43 or 47 wherein the modified variant is a protein having a conductance of at least 2 pS when expressed in a Xenopus oocyte, a molecular weight of between 40 and 100 Kd, and specifically reacts, under immunologically reactive conditions, with an antibody reactive to a full-length protein selected from the group consisting of: SEQ ID NO:1, SEQ ID NO:2, SEQ ID NO:3, SEQ ID NO:19, SEQ ID NO:20, SEQ ID NO:32, SEQ ID NO:43, and SEQ ID NO:47. Typically, the host cell is cultured under conditions permitting expression of the nucleic acid encoding the calcium-activated potassium channel protein.

In yet a further aspect, the present invention relates to an isolated nucleic acid sequence of at least 15 nucleotides in length which specifically hybridizes, under stringent conditions, to a nucleic acid encoding a calcium-activated potassium channel protein, where the protein is selected from the group consisting of SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47.

In an additional aspect, the present invention is directed to a method for detecting the presence of a calcium-activated potassium channel protein in a biological sample. The method comprises contacting the biological sample with an antibody, wherein the antibody specifically reacts, under immunologically reactive conditions, to an calcium-activated potassium channel protein having a sequence selected from the group consisting of: SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47 and allowing the antibody to bind to the protein under immunologically reactive conditions, wherein detection of the bound antibody indicates the presence of the channel protein.

In yet another aspect, the present invention provides a method for detecting the presence, in a biological sample, of a nucleic acid sequence encoding a calcium-activated potassium channel protein of at least 25 amino acids in length. The method comprises contacting the biological sample, under stringent hybridization conditions, with a nucleic acid probe comprising a nucleic acid segment that selectively hybridizes to a nucleic acid encoding the channel protein having a sequence selected from the group consisting of SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47; allowing the nucleic acid encoding the channel protein to selectively hybridize to the probe to form a hybridization complex, wherein detection of the hybridization complex is an indication of the presence of the nucleic acid sequence in the sample. In some embodiments, the hybridization conditions are moderate stringency hybridization conditions. In another embodiment, the calcium activated channel protein is at least 400 amino acid residues in length and when expressed in oocytes has a conductance of at least 2 pS. In a further embodiment, the nucleic acid probes comprises at least 250 contiguous nucleotides encoding a subsequence within the small or intermediate calcium-activated potassium channel protein core region.

In a further aspect, the present invention relates to an isolated calcium-activated potassium channel encoded by a nucleic acid amplified by primers which selectively hybridize, under stringent hybridization conditions, to the same nucleic acid sequence as primers selected from the group consisting of: for hSK1, SEQ ID NO:5 and SEQ ID NO:6; for rSK2 SEQ ID NO:7 and SEQ ID NO:8; for endogenous rSK3, SEQ ID NO:9 and SEQ ID NO:10; for rSK1, SEQ ID NO:11 and SEQ ID NO:12; for hSK2, SEQ ID NO:23 and SEQ ID NO:24; for hSK3, SEQ ID NO:25 and SEQ ID NO:26; and for hIK the following primer pairs will amplify a probe that is selective for identifying hIK1 from a human genomic or cDNA library: 5' GCCGTGCGT-GCAGGATTTAGG 3' (SEQ ID NO:34) and 5'CCAGAG-GCCAAGCGTGAGGCC 3' (SEQ ID NO:35) yielding a probe of about 270 bases or 5' TCCAAGATGCACAT-GATCCTG 3' (SEQ ID NO:36) and 5' GGACTGCTG-GCTGGGTTCTGG 3' (SEQ ID NO:37) yielding a probe of about 165 bases. For amplification of a full length hIK1 either of the following two primer pairs will work: 5' ATGGGCGGGGATCTGGTGCTTG 3' (SEQ ID NO:38) and 5' CTACTTGGACTGCTGGCTGGGTTC 3' (SEQ ID NO:39) or 5' ATGGGCGGGGATCTGGTGCTTGG 3' (includes codon of initiator methionine) (SEQ ID NO:40) and 5' GGGTCCAGCTACTTGGACTGCTG 3' (includes stop codon for end of translation) (SEQ ID NO:41).

In yet another aspect, the present invention relates to a method of identifying a compound which increases or decreases the potassium ion flux through a small or intermediate conductance, calcium-activated potassium channel, with the provisio that the compound is not clotrimizole. The method comprises the steps of contacting the compound with a eukaryotic host cell in which has been expressed a nucleic acid encoding a calcium-activated potassium channel having a sequence selected from the group consisting of SEQ ID NO:1, SEQ ID NO:2, SEQ ID NO:3, SEQ ID NO:4, SEQ ID NO:19, SEQ ID NO:20, SEQ ID NO:32, SEQ ID NO:43, SEQ ID NO:47 and conservatively modified variants thereof, wherein said conservatively modified variant specifically binds to antibodies specifically reactive with an antigen having an amino acid sequence selected from the group consisting of: SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47, have a conductance of at least 2 pS, and a molecular weight between 40 and 100 kilodaltons; and determining the increased or decreased flux of potassium ions through said channel. In preferred embodiments, the increased or decreased flux of potassium ions is determined by measuring the electrical current or flux of ions, or indirectly the change in voltage induced by the change in current or flux of ions, across the cell membrane of said eukaryotic host cell. In a particularly preferred embodiment, the channel protein has a sequence selected from the group consisting of SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47. In another preferred embodiment, the channel protein is recombinant.

In a further aspect, the present invention relates to an isolated eukaryotic nucleic acid encoding a calcium-activated potassium channel protein of at least 400 amino acid residues in length, wherein the calcium-activated channel protein comprises an amino acid sequence having at least 55 to 60% similarity over the length of a core region of a protein selected from the group consisting of: SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47 and wherein the channel protein has a conductance of at least 2 pS. In some embodiments, the present invention is directed to the protein encoded by the aforementioned isolated eukaryotic nucleic acid. In other embodiments, the isolated nucleic acid encoding the calcium-activated channel protein has at least 85% sequence similarity over a comparison window of 20 contiguous amino acid residues within the core region.

In a further aspect, the present invention is directed to a vector comprising an isolated eukaryotic nucleic acid encoding a calcium-activated potassium channel protein of at least 400 amino acid residues in length, wherein the channel protein comprises an amino acid sequence having at least 55% similarity over the length of a core region of a protein selected from the group consisting of: SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47, and wherein the channel protein has a conductance of at least 2 pS. Typically, the vector is transfected into a host cell which is cultured under conditions permitting expression of the isolated eukaryotic nucleic acid encoding the channel protein.

In a further aspect, present invention is directed to a method of identifying a compound that increases or decreases the potassium ion flux through a calcium-activated potassium channel. The methods comprises the steps of contacting the compound with a eukaryotic host cell in which has been expressed a calcium-activated potassium channel protein of at least 400 amino acid residues in length, wherein the channel protein has an amino acid sequence having at least 55% similarity over the length of a core region of a protein selected from the group consisting of: SEQ ID NO:1, SEQ ID NO:2, SEQ ID NO:3, SEQ ID NO:4, SEQ ID NO:19, SEQ ID NO:20, SEQ ID NO:32, SEQ ID NO:43, and SEQ ID NO:47, and wherein the channel protein has a conductance of at least 2 pS; and determining the increased or decreased flux of potassium ions through the channel protein. In some embodiments the increased or decreased flux of potassium ions is determined by measuring the electrical current across the cell membrane of the eukaryotic host cell.

In another aspect, the present invention provides in a computer system a method of screening for mutations of SK and IK genes, the method comprising the steps of: (i) receiving input of a first nucleic acid sequence encoding a calcium-activated channel protein having a sequence selected from the group consisting of SEQ ID NOS:1, 2, 3, 4, 19, 20, 32, 43, 47 and conservatively modified versions thereof; (ii) comparing the first nucleic acid sequence with a second nucleic acid sequence having substantial identity to the first nucleic acid sequence; and (iii) identifying nucleotide differences between the first and second nucleic acid sequences. In one embodiment, the second nucleic acid sequence is associated with a disease state.

In another aspect, the invention provides in a computer system, a method for identifying a three-dimensional structure of SK and IK proteins, the method comprising the steps of: (i) receiving input of an amino acid sequence of a calcium-activated channel protein or a nucleotide sequence of a gene encoding the protein, the protein having an amino acid sequence selected from the group consisting of SEQ ID NOS:1, 2, 3, 4, 19, 20, 32, 43, 47, and conservatively modified versions thereof; and (ii) generating a three-dimensional structure of the protein encoded by the amino acid sequence. In one embodiment, the amino acid sequence is a primary structure and the generating step includes the steps of forming a secondary structure from the primary structure using energy terms encoded by the primary structure and forming a tertiary structure from the secondary structure using energy terms encoded by said secondary structure. In another embodiment, the generating step includes the step of forming a quaternary structure from the tertiary structure using anisotropy terms encoded by the tertiary structure. In another embodiment, the method further comprises the step of identifying regions of the three-dimensional structure of the protein that bind to ligands and using the regions to identify ligands that bind to the protein.

DETAILED DESCRIPTION OF THE INVENTION

The present invention provides novel isolated, small conductance, calcium-activated potassium (SK) channels, intermediate conductance, calcium-activated potassium (IK) channels (collectively, "calcium-activated potassium channels"), and isolated nucleic acids encoding SK and IK channels (i.e., SK and IK channel nucleic acids). The distribution, function, and pharmacology define these new classes of channels as SK or IK channels.

Expression of isolated SK or IK channel protein encoding nucleic acids in a host cell provides a composition which can be used to identify compounds that increase or decrease potassium ion flux through small conductance, calcium-activated potassium (SK) channels or intermediate conductance, calcium-activated potassium (IK) channels, respectively. Since SK channels underlie the slow component of the afterhyperpolarization (sAHP) of neurons, alteration of neuronal sAHP provides a means to inhibit epileptic seizures or modulate learning or memory disorders.

Calcium activated, SK channels are also implicated in T-cell activation. Thus, increasing or decreasing SK channel currents provides a means to inhibit or potentiate the immune response. Moreover, SK channels are associated with hormone and neurotransmitter secretions. Accordingly, altering SK channel currents provides a means to regulate cellular or glandular secretions and thereby treat imbalances thereof.

Calcium activated intermediate channels (IK) are also believed to play an important physiological role particularly in peripheral tissues. For example, intermediate channels are reported in red blood cells, and, in part, contribute to cell dehydration, a process that is exacerbated in sickle cell anemia.

The invention also relates to subsequences of isolated small conductance and intermediate conductance, calcium-activated potassium channels and for isolated nucleic acids encoding SK and IK channel proteins. Isolated nucleic acids coding for SK or IK channel proteins provide utility as probes for identification of aberrant transcription products or increased or decreased transcription levels of genes coding for SK or IK channels. Assaying for increased or decreased transcription can be used in drug screening protocols. Likewise, SK or IK channel proteins can be used as immunogens to generate antibodies for use in immunodiagnostic assays of increased or decreased expression of calcium-activated potassium channels in drug screening assays.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. The terms defined below are more fully defined by reference to the specification as a whole.

The terms "nucleic acid" "probe", or "primer" includes reference to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the perfect complementary sequence thereof. Eukaryotic nucleic acids are nucleic acids from eukaryotic cells, preferably cells of multicellular eukaryotes.

The term "recombinant" when used with reference to a cell, or protein, nucleic acid, or vector, includes reference to a cell, protein, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes and proteins that are not found within the native (non-recombinant) form of the cell or express native genes that are otherwise abnormally expressed, under expressed or not expressed at all.

The term "subsequence" in the context of a referenced nucleic acid sequence includes reference to a contiguous sequence from the nucleic acid having fewer nucleotides in length than the referenced nucleic acid. In the context of a referenced protein, polypeptide, or peptide sequence (collectively, "protein"), "subsequence" refers to a contiguous sequence from the referenced protein having fewer amino acids than the referenced protein.

The terms "identical" or "sequence identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., USA).

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol.* 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene,* 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual alignment.

The terms "substantial identity" or "similarity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BLAST) using standard parameters. One indication that two nucleic acid sequences are substantially identical is that the polypeptide which the first nucleic acid encodes is immunologically cross reactive with the polypeptide encoded by the second nucleic acid.

Another indication that two nucleic acid sequences have substantially identity is that the two molecules hybridize to each other under "moderate stringency hybridization conditions" (or "moderate conditions"). Exemplary "moderate stringency hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Nucleic acids which do not hybridize to each other under moderate stringency hybridization conditions are still substantially identical if the polypeptides which they encode are substantially identical. This occurs, e.g., when a copy of a nucleic acid is created using the maximum codon degeneracy permitted by the genetic code.

The terms "substantial identity" or "similarity" in the context of a peptide indicates that a peptide comprises a sequence with at least 60% sequence identity to a reference sequence, usually at least 70%, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Generally, similarity is determined using a comparison window having a length of any number from 20 contiguous positions to the number of residues in the full-length core region sequence (i.e., the region of optimal alignment with rSK2 from amino acid residue 135 to 462), where the comparison window is within the core sequence.

The terms "oligonucleotide" or "polynucleotide" probes include reference to both double stranded and single stranded DNA or RNA. The terms also refer to synthetically or recombinantly derived sequences essentially free of non-nucleic acid contamination.

As used herein, "contact" or "contacting" means to place in direct physical association.

"Biological sample" as used herein is a sample of biological tissue or fluid that contains an IK and/or SK channel protein or nucleic acid encoding the corresponding IK and/or SK channel protein. Such samples include, but are not limited to, sputum, amniotic fluid, blood, blood cells (e.g., white cells), or tissue. Biological samples may also include sections of tissues such as frozen sections taken for histological purposes. Examples of biological samples include a cell sample from nervous, muscular, glandular or epithelial tissue or from the immune system (e.g., T cells). A biological sample is typically obtained from a eukaryotic organism, preferably a multicellular eukaryotes such as insect, protozoa, birds, fish, reptiles, and preferably a mammal such as rat, mice, cow, dog, guinea pig, or rabbit, and most preferably a primate such as macaques, chimpanzees, or humans.

The term "antibody" also includes antigen binding forms of antibodies (e.g., Fab, F(ab)$_2$). The term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 10 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, *Fundamental Immunology*, Third Edition, W. E. Paul, ed., Raven Press, N.Y. 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Proteins* W. H. Freeman and Company.

The terms "biologically pure" or "isolated" refer to material which is substantially or essentially free from components which normally accompany or interact with it as found in its naturally occurring environment. The isolated material optionally comprises material not found with the material in its natural environment.

The phrase "encodes a protein which could be encoded by a nucleic acid that selectively hybridizes under moderate stringency hybridization conditions to a sequence selected from the group consisting of:" in the context of nucleic acids refers to those nucleic acids encoding naturally occurring proteins or derivatives of natural proteins, but which are deliberately modified or engineered to no longer hybridize to the protein of natural origin under the stated conditions.

An "expression vector" is a nucleic acid construct, generated recombinantly or synthetically, with a series of specified nucleic acid elements which permit transcription of a particular nucleic acid in a host cell. The expression vector can be part of a plasmid, virus, or nucleic acid fragment. Typically, the expression vector includes a nucleic acid to be transcribed, and a promoter.

The phrase "functional effects" in the context of assays for testing compounds affecting the channel includes the determination of any parameter that is indirectly or directly under the influence of the channel. It includes changes in ion flux and membrane potential but also includes other physiologic effects such increases or decreases of transcription or hormone release.

By "selectively hybridizing" or "selective hybridization" or "selectively hybridizes" is meant hybridization, under stringent hybridization conditions, of a nucleic acid sequence to a specified nucleic acid target sequence to a detectably greater degree than its hybridization to non-target nucleic acid sequences and/or to the substantial exclusion of non-target nucleic acids. Selectively hybridizing sequences have at least 80% sequence identity, preferably 90% sequence identity, and most preferably 100% sequence identity (i.e., complementary) with each other. "Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "stringent conditions" or "stringent hybridization conditions" refer to conditions under which a probe will hybridize to its target sequence, to a detectably greater degree than other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The $T_m$ is the temperature (under defined ionic strength and pH) at which 50% of a complementary target sequence hybridizes to a perfectly matched probe. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30% formamide, 1 M NaCl, 1% SDS at 37° C., and a wash in 2×SSC at 50° C. Exemplary high stringency conditions include hybridization in 50% formamide, 1 M NaCl, 1% SDS at 37° C., and a wash in 0.1×SSC at 60° C.

"Stringent hybridization conditions" or "stringent conditions" in the context of nucleic acid hybridization assay formats are sequence dependent, and are different under different environmental parameters. An extensive guide to the hybridization of nucleic acids is found in Tijssen (1993) *Laboratory Techniques in Biochemistry and Molecular Biology— Hybridization with Nucleic Acid Probes* Part I, Chapter 2 "Overview of principles of hybridization and the strategy of nucleic acid probe assays", Elsevier, New York. Stringent conditions are sequence-dependent and will be different in different circumstances. Longer sequences hybridize specifically at higher temperatures.

By "hybridization complex" is meant a duplex nucleic acid sequence formed by selective hybridization of two single-stranded nucleic acid sequences with each other.

By "host cell" is meant a cell which contains an expression vector and supports the replication or expression of the expression vector. Host cells may be prokaryotic cells such as *E. coli*, or eukaryotic cells such as yeast, insect, amphibian, or mammalian cells.

By "conductance" is meant electrical conductance. Electrical conductance is conveniently measured in Siemens (1/ohm=mho). Unitary conductance is determined by measuring single channel currents using a patch clamp protocol under conditions set forth in Example 6 (i.e., in an oocyte) using a symmetrical potassium ion concentration of 120 mM. See generally, Hille, B., Ionic Channels of Excitable Membranes, 2nd ed., Sinauer Assoc., Sunderland, Mass. In the context of the present invention, "conductance" refers to the unitary electrical conductance of a single homomeric protein of the referenced SK or IK channel protein.

By "when expressed in an oocyte leads to formation of an SK channel" includes reference to expression of a referenced SK protein in which a plurality of the referenced SK proteins are assembled to form, by themselves or in conjunction with other endogenous *Xenopus* oocyte molecules, an SK channel. Expression within a *Xenopus* oocyte is disclosed in the Examples provided herein, e.g., Example 3.

By "when expressed in an oocyte leads to formation of a calcium-activated potassium channel" includes reference to expression of a referenced IK and/or SK protein in which a plurality of the referenced IK and/or SK proteins are assembled to form, by themselves or in conjunction with other endogenous *Xenopus* oocyte molecules, a calcium-activated potassium channel. Expression within a *Xenopus* oocyte is disclosed in the Examples provided herein, e.g., Example 3.

By "immunologically reactive conditions" is meant conditions which allow an antibody, generated to a particular epitope, to bind to that epitope to a detectably greater degree than the antibody binds to substantially all other epitopes. Immunologically reactive conditions are dependent upon the format of the antibody binding reaction and typically are those utilized in immunoassay protocols. See Harlow and Lane (1988) *Antibodies, A Laboratory Manual*, Cold Spring Harbor Publications, New York, for a description of immunoassay formats and conditions.

By "antibody reactive to a protein" is meant the protein is "specifically immunoreactive with an antibody."

The phrase "specifically immunoreactive with an antibody", or "specifically binds to an antibody" when referring to a protein or peptide, refers to a binding reaction between an antibody and a protein having an epitope recognized by the antigen binding site of the antibody. This binding reaction is determinative of the presence of a protein having the recognized epitope amongst the presence of a heterogeneous population of proteins and other biologics.

Thus, under designated immunoassay conditions, the specified antibodies bind to a protein having the recognized epitope and bind, if at all, to a detectably lesser degree to other proteins lacking the epitope which are present in the sample.

Specific binding to an antibody under such conditions may require an antibody that is selected for its specificity for a particular protein. For example, antibodies raised to the calcium activated potassium channel protein with the amino acid sequence depicted in SEQ ID NO:1, 2, 3, 4, 19, 20, 30, 32, 43, and 47 can be selected from to obtain antibodies specifically immunoreactive with small and/or intermediate calcium activated potassium channel proteins and not with other proteins. The proteins used as immunogens can be in native conformation or denatured so as to provide a linear epitope.

A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

By "transfected" is meant the introduction of a nucleic acid into a eukaryotic cell where the nucleic acid may be incorporated into the genome of the cell (i.e., chromosome, plasmid, or mitochondrial DNA), converted into an autonomous replicon, or transiently expressed (e.g., transfected mRNA). The transfection can be in vivo or ex vivo. "Ex vivo" means outside the body of the organism from which a cell or cells is obtained or from which a cell line is isolated. Ex vivo transfection is preferably followed by re-infusion of the cells back into the organism. In contrast, by "in vivo" is meant within the body of the organism from which the cell was obtained or from which a cell line is isolated.

By "antigen" is meant a substance to which an antibody can be generated and to which the antibody is specifically immunoreactive with. An antibody immunologically reactive with a particular antigen can be generated in vivo or by recombinant methods such as selection of libraries of recombinant antibodies in phage or similar vectors. See, e.g., Huse et al. (1989) *Science* 246:1275–1281; and Ward, et al. (1989) *Nature* 341:544–546; and Vaughan et al. (1996) *Nature Biotechnology*, 14:309–314.

By "encoding" or "encoded", with respect to a specified nucleic acid, is meant comprising the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.*, 82:2306–2309 (1985), or the ciliate *Macronucleus*, may be used when the nucleic acid is expressed using these organisms.

By "contiguous amino acids from" in the context of a specified number of amino acid residues from a specified sequence, is meant a sequence of amino acids of the specified number from within the specified reference sequence which has the identical order of amino acids each of which is directly adjacent to the same amino acids as in the reference sequence.

By "small conductance, calcium activated potassium channel" or "SK channel" is meant a membrane channel which is not voltage-gated, activated by calcium from about 30 nM to 10 $\mu$M, and has a unitary conductance of from about 2 to 60 pS, often 2 to 25 pS, when measured under a symmetrical potassium concentration of 120 mM using the conditions specified in Example 6. An SK channel comprises multiple SK channel proteins as subunits, typically four SK channel proteins (e.g., full length or substantially full length SK channel proteins).

By "small conductance, calcium-activated channel protein" or "SK channel protein" is meant a peptide of at least 10 contiguous amino acids in length from an amino acid sequence which makes up an SK channel. These proteins, when full length, serve as monomers of the SK channel. Thus, an SK channel protein can have the functional characteristics to form a heteromeric or homomeric protein with the functional characteristics of an SK channel, or be a peptide fragment thereof. For example, both N-terminal extended rsk3 (SEQ ID NO:43 and truncated rsk3 (SEQ ID NO:3) demonstrate virtually identical functional characteristics.

By "intermediate conductance, calcium-activated potassium channel" or "IK channel" is meant a membrane channel which is not voltage-gated, activated by calcium from about 30 nM to 10 $\mu$M, and has in its broadest context a unitary inward conductance of from about 20 to 80 pS, but more likely 30 to 70 pS, 40 to 60 pS, or most preferably about 35 to 40 pS when measured under a symmetrical potassium concentration of 120 mM using the conditions specified in Example 6. An IK channel comprises multiple IK channel proteins as subunits, typically four IK channel proteins (e.g., full length or substantially full length IK channel proteins).

By "intermediate conductance, calcium-activated channel protein" or "IK channel protein" is meant a peptide of at least 10 contiguous amino acids in length from an amino acid sequence which makes up an IK channel. These proteins, when full length, serve as monomers of the IK channel. Thus, an IK channel protein can have the functional characteristics to form a heteromeric or homomeric protein with the functional characteristics of an IK channel, or be a peptide fragment thereof.

By "calcium-activated potassium channel" means a small conductance, calcium-activated potassium (SK) channel, and an intermediate conductance, calcium-activated potassium (IK) channel.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

By "specifically reacts" or "specifically reactive" is meant a reaction of the specificity exhibited by that between an antibody and a protein which "specifically binds" with that antibody.

By "human genomic library" is meant a collection of isolated DNA molecules which substantially represent the entire genome of a human. Construction of genomic libraries is taught in standard molecular biology references such as Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel).

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, Ed. D. H. Persing et al., American Society for Microbiology, Washington, D.C.

The term "residue" or "amino acid residue" or "amino acid" as used herein refers to an amino acid that is incorporated into a protein, polypeptide, or peptide (collectively "peptide"). The amino acid may be a naturally occurring amino acid and, unless otherwise limited, may encompass known analogs of natural amino acids that can function in a similar manner as naturally occurring amino acids.

By "segment of nucleic acid" is meant a nucleic acid sequence of any one of from 15 to about 1500 nucleotides, or nucleotide analogs, in length or concatamers of such sequence.

By "determining the functional effect" is meant examining the effect of a compound that increases or decreases potassium ion flux on a cell or cell membrane in terms of cell and cell membrane function. Preferably, the term refes to the functional effect of the compound on SK and IK channel activity, e.g., changes in conductance, voltage gating and the like. *Small and Intermediate Conductance, Calcium-Activated Potassium Channel Proteins*

The present invention provides intermediate conductance, calcium-activated (IK) potassium channel proteins, and small conductance, calcium-activated (SK) channel proteins collectively, "calcium-activated potassium channels"). The isolated small conductance, calcium-activated (SK) channel proteins of the present invention comprise at least N amino acids from any one of the sequences selected from the group consisting of: SEQ ID NO:1, SEQ ID NO:2, SEQ ID NO:3, SEQ ID NO:4, SEQ ID NO:19, SEQ ID NO:20, SEQ ID NO:43, and SEQ ID NO:47, and conservatively modified variants thereof, where N is any one of the integers selected from the group consisting of from 10 to 600 and the sequence is unique to the protein of origin.

Similarly, the isolated intermediate conductance, calcium-activated (IK) channel proteins of the present invention comprise at least N amino acids from SEQ ID NO:32 and conservatively modified variants thereof, where N is any one of the integers selected from the group consisting of from 10 to 600 and the sequence is unique to the protein of origin.

Typically, the calcium-activated potassium channel proteins and specific peptides are at least 15, 25, 35, or 50 amino acids in length, more preferably at least 100, 200, 300, 400, or 500 amino acids in length, and most preferably the full length of SEQ ID NOS:1, 2, 3, 4, 19, 20, 32, 43, or 47, or conservatively modified variants thereof. Thus, the present invention provides full-length and subsequences of SEQ ID NO:1, 2, 3, 4, 19, 20, 32, 43, and 47 and full-length and subsequences of conservatively modified variants of SEQ ID NO:1, 2, 3, 4, 19, 20, 32, 43, and 47. A "full-length" sequence of SEQ ID NO:1, 2, 3, 4, 19, 20, 32, 43, or 47 means the sequence of SEQ ID NO:1, 2, 3,4, 19, 20, 32, 43 or 47, respectively. A "full-length" sequence of a conservatively modified variant of SEQ ID NO:1, 2, 3, 4, 19, 20, 32, 43 or 47 means a conservatively modified variant of SEQ ID NO:1, 2, 3, 4, 19, 20, 32, 43 or 47 respectively. The calcium-activated potassium channel proteins and peptides of the present invention can be used as immunogens for the preparation of immunodiagnostic probes for assessing increased or decreased expression of calcium-activated potassium channels in drug screening assays.

The calcium-activated potassium channel proteins of the present invention also include proteins which have substantial identity (i.e., similarity) to a calcium-activated potassium channel protein of at least N amino acids from any one of the sequences selected from the group consisting of SEQ ID NO:1, SEQ ID NO:2, SEQ ID NO:3, SEQ ID NO:4, SEQ ID NO:19, SEQ ID NO:20, SEQ ID NO:32, SEQ ID NO: 43, and SEQ ID NO: 47 and conservatively modified variants thereof, where N is any one of the integers selected from the group consisting of 10 to 600. Generally, the calcium-activated potassium channel proteins are at least 50, typically at least 100, preferably at least 200, more preferably at least 300, and most preferably at least 400 amino acid residues in length. Typically, the substantially similar or conservatively modified variant of the calcium-activated potassium SK or IK channel protein is a eukaryotic protein, preferably from a multicellular eukaryotes such as insects, protozoans, birds, fishes, amphibians, reptiles, or mammals.

The SK channel proteins which are substantially identical to, or a conservatively modified variant of, an SK channel protein having a sequence selected from SEQ ID NO:1, SEQ ID NO:2, SEQ ID NO:3, SEQ ID NO:4, SEQ ID NO:19, SEQ ID NO:20, SEQ ID NO:43 and SEQ ID NO:47 will specifically react, under immunologically reactive conditions, with an immunoglobulin reactive to an SK channel protein selected from the group consisting of SEQ ID NO:1, SEQ ID NO:2, SEQ ID NO:3, SEQ ID NO:4, SEQ ID NO:19, SEQ ID NO:20, SEQ ID NO:43, and SEQ ID NO:47.

Similarly, IK channel proteins which are substantially identical to, or a conservatively modified variant of, an IK channel protein having a sequence selected from SEQ ID NO:32 will specifically react, under immunologically reactive conditions, with an immunoglobulin reactive to an IK channel protein such as SEQ ID NO:32. A variety of immunoassay formats may be used to assess such an immunologically specific reaction including, for example, ELISA, competitive immunoassays, radioimmunoassays, Western blots, indirect immunofluorescent assays and the like.

Alternatively, the SK channel proteins which are substantially identical to, or are a conservatively modified variant of, an SK channel protein having a sequence selected from of, SEQ ID NO:1, SEQ ID NO:2, SEQ ID NO:3, SEQ ID NO:4, SEQ ID NO:19, SEQ ID NO:20, SEQ ID NO:43, and SEQ ID NO:47 will comprise an amino acid sequence which has any one of the values from 60% to 100% similarity to a comparison window within the core sequence (or "core region") of an SK channel protein selected from the group consisting of SEQ ID NOS:1, 2, 3, 4, 19, 20, 43, and 47. IK channel proteins which are substantially identical to, or are a conservatively modified variant of, an IK channel protein having the sequence of SEQ ID NO:32 will comprise an amino acid sequence which has any one of the values from 60% to 100% similarity to a comparison window within the core sequence (or "core region") of the IK channel protein hIK1.

Thus, similarity is determined by reference to the core region or subsequence thereof. The core region of hSK1 (SEQ ID NO:1) is from amino acid residue 124 through 451 (SEQ ID NO:27). The core region of rSK2 (SEQ ID NO:2) is from amino acid residue 135 through 462. The core region of truncated rSK3 (SEQ ID NO:3) is from amino acid residue 109 through 436. The core region of N-terminal extended rSK3 (SEQ ID NO:43) is from 288–615. The core region of rSK1 (SEQ ID NO:4) is defined by the region which aligns with the foregoing regions. The core region of hSK2 (SEQ ID NO:19) is from amino acid residue 134 through 461. The core region of truncated hSK3 (SEQ ID NO:20) is from amino acid residue 109 through 436. The core region of N-terminal extended hSK3 (SEQ ID NO:47) is from 238–465. Thus, the core region of SEQ ID NOS:1–4, 19, 20, 43 and 47 are inclusive of and defined by the amino acid residue subsequences LSDYALIFGM (SEQ ID NO:17) at the amino proximal end and QRKFLQAIHQ (SEQ ID NO:18) at the carboxyl proximal end. The core region of hIK1 (SEQ ID NO:32) is amino acids 25 through 351. A subsequence of the core region has a length of any one of the numbers from 10 to the length of a core sequence of SEQ ID NOS: 1, 2, 3, 4, 19, 20, 32, 43 or 47. Preferably, SK or IK channel proteins comprise an amino acid sequence having at least 90% similarity over a comparison window of 20 contiguous amino acids from within the core sequence.

Similarity is also determined by reference to functional characteristics of the calcium activated channel protein. For example, the present invention provides several SK3 amino acid sequences, which when expressed have virtually identical currents. cDNAs encoding rSK3 have been isolated in two different forms. The first, SEQ ID NO:44 encoding SEQ ID NO:43, is the endogenous rSK3 or N-terminal extended rSK3. The second, SEQ ID NO:16, encoding SEQ ID NO:3, is truncated relative to SEQ ID NO:43 at the N-terminus. Truncated rSK3 protein (SEQ ID NO:3) also has a different C-terminus, in which the last 9 amino acids of SEQ ID NO:43 are replaced with 5 different amino acids. Although these sequences differ at both the N- and C-terminus, they express virtually identical currents. Since the N-terminal extended and truncated SK3 express the same current, the N-terminal extension not essential to channel function per se but is likely involved in targeting the protein to a specific location in the cell.

Similarly, two cDNAs for hSK3 have been identified: N-terminal extended hSK3 (SEQ ID NO:48, encoding SEQ ID NO:47) and truncated hSK3 (SEQ ID NO:22, encoding SEQ ID NO:20). In addition, a similar N-terminal extension may exist for SK2. Genomic sequences from the mouse for both SK2 and SK3 demonstrate that both have an extended open reading frame, which is contiguous with the amino acids sequences for which functional current expression has been demonstrated. Thus, substantially identical SK channel proteins, or conservatively modified variants thereof, are also identified on the basis of functional characteristics.

The present invention provides functional SK and IK channel proteins and subsequences thereof. Functional SK channels of the present invention have a unitary conductance of between 2 and 60 pS, more usually 5 and 25 pS, and molecular weights between 40 and 100 Kd for each of the SK channel proteins which make up the SK channel, more usually 50 to 80 kD. Functional IK channels have a unitary conductance of between 20 and 80 pS, and often 30 to 60 pS. Unitary conductance may be conveniently determined using inside-out or outside-out patch clamp configurations. These configurations are particularly indicated for the study of the biophysics of ionic channels (kinetics, conductivity, selectivity, mechanism of permeation and block). Patch clamp methods are well known in the art. See, e.g., the review of Franciolini, *Patch clamp technique and biophysical study of membrane channels, Experientia,* 42(6): 589–594 (1986); and Sakmann et al., *Patch clamp techniques for studying ionic channels in excitable membranes, Annual Review of Physiology,* 46:455–472 (1984).

The isolated SK and IK proteins within the scope of the present invention include those which when full-length and expressed in a cell from a quiet line, define a functionality and pharmacology indicative of an SK channel or IK channel, respectively. A quiet line is a cell line that in its native state (e.g., not expressing recombinant SK or IK channels) has low or uninteresting electric activity, e.g., a CHO cell line. For example, a control cell (without expression of a putative SK channel of the present invention) and an experimental cell (expressing a putative SK channel) are maintained under conditions standard for measurement of electrophysiological paramaters as provided in the working examples disclosed herein. Each cell is treated with a calcium ionophore. Exemplary ionophores include, but are not limited to, such standard compounds as ionomycin (Sigma Chemical Co.) or A23187 (Sigma Chemical Co.). A cell is often treated with an ionophore at a concentration of about 1 $\mu$M.

Subsequently, electrophysiological measurements of the cells are taken to detect induction of a potassium current (e.g., by radiotracer), or a change in conductance of the cell (e.g., by patch clamp), or a change in voltage (e.g., by fluorescent dye). If the presence an ion channel is indicated by a calcium induced change, subsequent tests are used to characterize the channel as an SK channel of the present invention. Preferably, at least two characteristics are determined, more preferably at least 3, or 4 are determined. Characteristics of SK channels of the present invention are disclosed more fully herein.

For example, a cell expressing an SK channel of the present invention can have a conductance of between 2 to 30 pS, often between 2 to 25 pS, can, but not necessarily, exhibit block by apamin at a range from 10 pM to about 100 nM, can comprise an SK channel protein of about 40 to 80 kD, can exhibit sequence similarity of at least 60%, and more preferably at least 70%, 80%, 90% or 95% in an alignment with the core regions of the exemplary SK channel proteins disclosed herein, and can be specifically reactive, under immunologically reactive conditions, with an antibody raised to an exemplary SK or IK channel disclosed herein (e.g., SEQ ID NO:1–4, 19, 20, 32, 43 and 47). Such standard methods aid in the identification of SK proteins of the present invention. Cells expressing an IK channel have the same functional characteristics except they are blocked by CTX but not blocked by IBX or apamin and have a unitary conductance of between 20 and 80, often 35 to 40 pS.

Solid phase synthesis of SK or IK channel proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, *Solid-Phase Peptide Synthesis;* pp. 3–284 in *The Peptides: Analysis, Synthesis, Biology. Vol. 2: Special Methods in Peptide Synthesis, Part A.,* Merrifield, et al. *J. Am. Chem. Soc.,* 85: 2149–2156 (1963), and Stewart et al., *Solid Phase Peptide Synthesis,* 2nd ed. Pierce Chem. Co., Rockford, Ill. (1984). SK or IK channel proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

*Obtaining Nucleic Acids Encoding Calcium-Activated Potassium Channel Proteins*

The present invention provides isolated nucleic acids of RNA, DNA, or chimeras thereof, which encode calcium activated, SK channel proteins ("SK channel protein nucleic acids") or calcium activated, IK channel proteins ("IK channel protein nucleic acids) as discussed more fully above. Nucleic acids of the present invention can be used as probes, for example, in detecting deficiencies in the level of mRNA, mutations in the gene (e.g., substitutions, deletions, or additions), for monitoring upregulation of SK or IK channels in drug screening assays, or for recombinant expression of SK or IK channel proteins for use as immunogens in the preparation of antibodies.

Nucleic acids encoding the calcium-activated potassium channel proteins of the present invention can be made using standard recombinant or synthetic techniques. With the amino acid sequences of the SK or IK channel proteins herein provided, one of skill can readily construct a variety of clones containing functionally equivalent nucleic acids, such as nucleic acids which encode the same protein. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Sambrook, et al., *Molecular Cloning: A Laboratory Manual* (2nd Ed., Vols. 1–3, Cold Spring Harbor Laboratory (1989)), *Methods in Enzymology*, Vol. 152: *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

1. Isolation of SK and IK Channel Proteins by Nucleic Acid Hybridization

The isolated nucleic acid compositions of this invention, whether RNA, cDNA, genomic DNA, or a hybrid of the various combinations, are isolated from biological sources or synthesized in vitro. Deoxynucleotides can be prepared by any suitable method including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.,* 22: 1859–1862 (1981); the solid phase phosphoramidite triester method described by Beaucage and Caruthers (1981), *Tetrahedron Letts.,* 22(20): 1859–1862, e.g., using an automated synthesizer, e.g., as described in Needham-VanDevanter et al. (1984) *Nucleic Acids Res.,* 12:6159–6168; and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Nucleic acids encoding an SK channel protein of SEQ ID NO:1 may be obtained by amplification of a human hippocampal cDNA library using-isolated nucleic acid primers having the sequence: ATGCCGGGTCCCCGGGCGGC-CTGC (SEQ ID NO:5) and TCACCCGCAGTC-CGAGGGGGCCAC (SEQ ID NO:6). Nucleic acids encoding an SK channel protein of SEQ ID NO:2 may be obtained by amplification of a rat brain cDNA library using isolated nucleic acid primers having the sequence: ATGAGCAGCT-GCAGGTACAACGGG (SEQ ID NO:7) and CTAGC-TACTCTCAGATGAAGTTGG (SEQ ID NO:8). Nucleic acids encoding an SK channel protein of SEQ ID NO:43 may be obtained by amplification of a rat brain cDNA library using isolated nucleic acid primers having the sequence: ATGAGCTCCTGCAAATACAGCGGT (SEQ ID NO:9) and TTAGCAACTGCTTGAACTTG (SEQ ID NO:10). Nucleic acids encoding an SK channel protein of SEQ ID NO:4 may be obtained by amplification of a rat brain cDNA library using isolated nucleic acid primers having the sequence TCAGGGAAGCCCCCGACCGTCAGT (SEQ ID NO:11) and TCACCCACAGTCTGATGCCGTGGT (SEQ ID NO:12). Nucleic acids encoding an SK channel protein of SEQ ID NO:19 may be obtained by amplification of a human hippocampal cDNA library using isolated nucleic acid primers having the sequence: ATGAGCAGCT-GCAGGTACAACG (SEQ ID NO:23) and CTAGC-TACTCTCTGATGAAGTTG (SEQ ID NO:24). Nucleic acids encoding an SK channel protein of SEQ ID NO:20 (hSK3) may be obtained by amplification of a human hippocampal cDNA library using isolated nucleic acid primers having the sequence: ATGAGCTCCTGCAAGTATAGC (SEQ ID NO:25) and TTAGCAACTGCTTGAACTTGTG (SEQ ID NO:26). Nucleic acids encoding the IK channel protein of SEQ ID NO:32 may be obtained by amplification of a human pancreas cDNA library using isolated nucleic acid primer pairs having the sequence: (SEQ ID NOS:38 and 39) and (SEQ ID NOS:40 and 41).

The isolated nucleic acids of the present invention may be cloned, or amplified by in vitro methods, such as the polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Amnheim & Levinson (Oct. 1, 1990) *C&EN* 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.,* 35: 1826; Landegren et al., (1988) *Science,* 241: 1077–1080; Van Brunt (1990) *Biotechnology,* 8: 291–294; Wu and Wallace, (1989) *Gene,* 4: 560; and Barringer et al. (1990) Gene, 89:117.

Isolated nucleic acids encoding SK channel proteins comprise a nucleic acid sequence encoding an SK channel protein selected from the group consisting of SEQ ID NO:1, SEQ ID NO:2, SEQ ID NO:3, SEQ ID NO:4, SEQ ID NO:19, SEQ ID NO:20, and subsequences thereof. In preferred embodiments, the isolated nucleic acid encoding an SK channel protein is selected from the group consisting of: SEQ ID NO:13, SEQ ID NO:14, SEQ ID NO:15, SEQ ID NO:16, SEQ ID NO:21, SEQ ID NO:22, and subsequences thereof.

Isolated nucleic acids encoding IK channel proteins comprise a nucleic acid sequence encoding an IK channel protein such as SEQ ID NO:32, and subsequences thereof. In preferred embodiments, the isolated nucleic acid encoding an IK channel protein is SEQ NO:31 and subsequences thereof.

In addition to the isolated nucleic acids identified herein, the invention also includes other isolated nucleic acids encoding calcium-activated potassium channel proteins which selectively hybridize, under stringent conditions, to a nucleic acid encoding a protein selected from the group consisting of: SEQ ID NO:1, SEQ ID NO:2, SEQ ID NO:3, SEQ ID NO:4, SEQ ID NO:19, SEQ ID NO:20, SEQ ID NO:32, SEQ ID NO:43 and SEQ ID NO:47, and subsequences thereof. Generally, the isolated nucleic acid encoding a calcium-activated potassium channel protein of the present invention will hybridize under at least moderate stringency hybridization conditions to a nucleic acid sequence from SEQ ID NOS: 13, 14, 15, 16, 21, 22, 31, 44, or 48 which encodes the core region or subsequence thereof. Alternatively, or additionally, the isolated nucleic acid encoding the calcium-activated potassium channel protein will encode an amino acid sequence of at least 60%, 70%, 80%, or 90% similarity over the length of the core region. Conveniently, the nucleic acid encoding a subsequence of the core region is obtained from SEQ ID NOS: 13, 14, 15, 16, 21, 22, 32, 44, or 48 and is at least any one of from 15 to 400 nucleotides in length, and generally at least 250 or 300 nucleotides in length; preferably the nucleic acid will encode the entire core sequence. The nucleic acid sequence, or subsequence thereof, encoding the calcium-activated potassium channel protein comprises at least N' nucleotides in length, where N' is any one of the integers selected from the group consisting of from 18 to 2000. Thus, the nucleic acids of the present invention comprise genomic DNA and nuclear transcripts encoding SK and IK channel proteins.

Where the nucleic acid encoding an SK or IK channel protein is to be used as nucleic acid probes, it is often desirable to label the nucleic acid with detectable labels. The labels may be incorporated by any of a number of means well known to those of skill in the art. However, in a preferred embodiment, the label is simultaneously incorporated during the amplification step in the preparation of the nucleic acids. Thus, for example, polymerase chain reaction (PCR) with labeled primers or labeled nucleotides will provide a labeled amplification product. In another preferred embodiment, transcription amplification using a labeled nucleotide (e.g., fluorescein-labeled UTP and/or CTP) incorporates a label into the transcribed nucleic acids.

Alternatively, a label may be added directly to an original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g., with a labeled RNA) by phosphorylation of the nucleic acid and subsequent attachment (ligation) of a nucleic acid linker joining the sample nucleic acid to a label (e.g., a fluorophore).

Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may he detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The probes are used to screen genomic or cDNA libraries from any source of interest including specific tissues (e.g., heart, brain, pancreas) and animal source such as rat, human, bird, etc. Screening techniques are known in the art and are described in the general texts cited above such as in *Sambrook and Ausubel.*

2. Isolation of SK and IK Channel Proteins by Immunoscreening

In addition to using nucleic acid probes for identifying novel forms of the protein claimed herein, it is possible to use antibodies to probe expression libraries. This is a well known technology. (See Young and Davis, 1982 Efficient isolation of genes using antibody probes *Proc. Natl. Acad. Sci., U.S.A.* 80:1194–1198.) In general, a CDNA expression library maybe prepared from commercially available kits or using readily available components. Phage vectors are preferred, but a variety of other vectors are available for the expression of protein, such vectors include but are not limited to yeast, animal cells and *Xenopus* oocytes. One selects mRNA from a source that is enriched with the target protein and creates cDNA which is then ligated into a vector and transformed into the library host cells for immunoscreening. Screening involves binding and visualization of antibodies bound to specific proteins on cells or immobilized on a solid support such as nitrocellulose or nylon membranes. Positive clones are selected for purification to homogeneity and the isolated cDNA then prepared for expression in the desired host cells. A good general review of this technology can be found in Methods of Cell Biology Vol 37 entitled Antibodies in Cell Biology, Ed. D J Asai pp 369–382, 1993.

When choosing to obtain calcium activated channel proteins antibodies selective for the entire protein or portions can be used. Suitable peptide sequences include, but are not limited to, GHRRALFEKRKRLSDY (SEQ ID NO:28), FTDASSRSIGAL (SEQ ID NO:29), and ARKLELT-KAEKHVHNFMMDTQLTKR (SEQ ID NO:30) or ARKLELTKAEKHVHNFMMDTQLTK (SEQ ID NO:42).

Nucleic Acid Assays

This invention also provides methods of detecting and/or quantifying SK or IK channel protein expression by assaying for the gene transcript (e.g., nuclear RNA, mRNA). The assay can be for the presence or absence of the normal gene or gene product, for the presence or absence of an abnormal gene or gene product, or quantification of the transcription levels of normal or abnormal SK or IK channel protein gene product.

In a preferred embodiment, nucleic acid assays are performed with a sample of nucleic acid isolated from the organism to be tested. In the simplest embodiment, such a nucleic acid sample is the total mRNA isolated from a biological sample. The nucleic acid (e.g., either genomic DNA or mRNA) may be isolated from the sample according to any of a number of methods well known to those of skill in the art.

Methods of isolating total DNA or mRNA for use in, inter alia, a nucleic acid assay are well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993). One of skill will appreciate that where alterations in the copy number of the gene encoding an SK or IK channel protein is to be detected genomic DNA is preferably isolated. Conversely, where expression levels of a gene or genes are to be detected, preferably RNA (mRNA) is isolated.

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid. Detailed protocols for quantitative PCR are provided in *PCR Protocols, A Guide to Methods and Applications*, Innis et al., Academic Press, Inc. N.Y., (1990).

The method of detecting the presence of a nucleic acid sequence encoding an SK channel protein generally comprises: (a) contacting the biological sample, under stringent hybridization conditions, with a nucleic acid probe comprising a nucleic acid segment which selectively hybridizes to a nucleic acid sequence (target) encoding an SK channel protein selected from the group consisting of SEQ ID NO:1, SEQ ID NO:2, SEQ ID NO:3, SEQ ID NO:4, SEQ ID NO:19, SEQ ID NO:20, SEQ ID NO:43, and SEQ ID NO:47; (b) allowing the probe to specifically hybridize to the nucleic acid encoding an SK channel protein to form a hybridization complex, wherein detection of the hybridization complex is an indication of the presence of the SK nucleic acid sequence in the sample. Detection of an IK channel protein is accomplished in a similar fashion using a nucleic acid segment which selectively hybridizes to a nucleic acid sequence encoding an IK channel protein of SEQ ID NO:32.

The nucleic acid segment of the probe is a subsequence of at least N" contiguous nucleotides in length from a nucleic acid encoding an SK channel selected from the group consisting of SEQ ID NO:13, SEQ ID NO:14, SEQ ID NO:15, SEQ ID NO:16, SEQ ID NO:21, SEQ ID NO:22, SEQ ID NO:44, and SEQ ID NO:48, and complementary sequences thereof N" is an any one of the integers selected from the group consisting of each of the integers from 15 to 1500. For detecting the presence of an IK channel protein the nucleic acid segment is a subsequence of at least N" contiguous nucleotides in length from a nucleic acid encoding an IK channel of SEQ ID NO:31. "Contiguous nucleotides" from a referenced nucleic acid means a sequence of nucleotides having the same order and directly adjacent to the same nucleotides (i.e., without additions or deletions) as in the referenced nucleic acid. Typically, the nucleic acid segment is at least 18 nucleotides in length. The preferred length of the nucleic acid probe is from 24 to 200 nucleotides in length.

In particularly preferred embodiments, the nucleic acid segment is derived from a nucleic acid which encodes a core region from a protein selected from the group consisting of SEQ ID NO:1, 2, 3, 4, 19, 20, 32, 43 and 47. Conveniently, the nucleic acid which encodes the core region is a subsequence of a nucleic acid selected from the group consisting of: SEQ ID NOS: 13, 14, 15, 16, 21, 22, 31, 44, 48, and complementary sequences thereof. Usually, and particularly for cross-species hybridization, the nucleic acid segment would encode an amino acid sequence from within the core region and will be at least 250 nucleotides in length, most preferably will encode the entirety of the core region, and/or will hybridize to the target sequence under moderate stringency hybridization conditions.

Those of skill will appreciate that nucleic acid sequences of the probe will be chosen so as not to interfere in the selective hybridization of the nucleic acid segment to the target. Thus, for example, any additional nucleotides attached to the nucleic acid segment will generally be chosen so as not to selectively hybridize, under stringent conditions, to the nucleic acid target (potential false negative), nor to nucleic acids not encoding an SK or IK channel proteins or peptides (potential false positive). The use of negative and positive controls to ensure selectivity and specificity is known to those of skill. In general, the length of the probe should be kept to the minimum length necessary to achieve the desired results. The length of the nucleic acid encoding an SK or IK channel protein or peptide (i.e., the "SK channel protein nucleic acid" or "IK channel protein nucleic acid", respectively) is discussed more fully, supra, but is preferably at least 30 nucleotides in length.

A variety of nucleic acid hybridization formats are known to those skilled in the art. For example, common formats include sandwich assays and competition or displacement assays. Hybridization techniques are generally described in Berger and Kimmel, (1987), supra.; "*Nucleic Acid Hybridization, A Practical Approach*" (Hames, B. D. and Higgins, S. J. (eds.), IRL Press, 1985; Gall and Pardue, (*Proc. Natl. Acad. Sci.*, U.S.A. 63:378–383 (1969)); and John, Burnsteil and Jones (*Nature*, 223:582–587 (1969)).

Sandwich assays are commercially useful hybridization assays for detecting or isolating nucleic acid sequences. Such assays utilize a "capture" nucleic acid covalently immobilized to a solid support and a labelled "signal" nucleic acid in solution. The biological sample will provide the target nucleic acid. The "capture" nucleic acid probe and the "signal" nucleic acid probe hybridize with the target nucleic acid to form a "sandwich" hybridization complex. To be effective, the signal nucleic acid cannot hybridize with the capture nucleic acid.

In in situ hybridization, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4(3):230–250 (1986); Haase et al., *Methods in Virology*, Vol. VII, pp. 189–226 (1984); Wilkinson, "The theory and practice of in situ hybridization" In: *In situ Hybridization*, Ed. D. G. Wilkinson. IRL Press, Oxford University Press, Oxford; and *Nucleic Acid Hybridization: A Practical Approach*, Ed. Hames, B. D. and Higgins, S. J., IRL Press (1987).

Typically, labelled signal nucleic acids are used to detect hybridization. Complementary nucleic acids or signal nucleic acids may be labelled by any one of several methods typically used to detect the presence of hybridized oligo-nucleotides. The most common method of detection is the use of autoradiography with $^3$H, $^{125}$I, $^{35}$S, $^{14}$C, or $^{32}$P-labelled probes or the like. Other labels include ligands which bind to labelled antibodies, fluorophores, chemi-lumninescent agents, enzymes, and antibodies which can serve as specific binding pair members for a labelled ligand.

The label may also allow for the indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen, "Practice and Theory of Enzyme Immunoassays," *Laboratory Techniques in Biochemistry and Molecular Biology*" (Burdon, van Knippenberg (eds.), Elsevier, pp. 9–20 (1985)).

The detectable label used in nucleic acids of the present invention may be incorporated by any of a number of means known to those of skill in the art, e.g., as discussed supra. Means of detecting such labels are well known to those of skill in the art.

The sensitivity of the hybridization assays may be enhanced through the use of a nucleic acid amplification system which multiplies the target nucleic acid being detected. Examples of such systems include the polymerase chain reaction (PCR) system and the ligase chain reaction (LCR) system. Other methods known in the art are the nucleic acid sequence based amplification (NASBA, Cangene, Mississauga, Ontario) and Q-Beta Replicase systems.

Those of skill will appreciate that abnormal expression levels or abnormal expression products (e.g., mutated transcripts, truncated or non-sense proteins) are identified by comparison to normal expression levels and normal expression products. Normal levels of expression or normal expression products can be determined for any particular population, subpopulation, or group of organisms according to standard methods known to those of skill in the art. Typically this involves identifying healthy organisms (i.e., organisms with a functional SK or IK channel protein as indicated by such properties as conductance and calcium sensitivity) and measuring expression levels of the SK or IK channel protein gene (as described herein) or sequencing the gene, mRNA, or reverse transcribed cDNA, to obtain typical (normal) sequence variations. Application of standard statistical methods used in molecular genetics permits determination of baseline levels of expression, and normal gene products as well as significant deviations from such baseline levels.

Nucleic Acid Assay Kits

The nucleic acids of this invention can be included in a kit which can be used to determine in a biological sample the presence or absence of the normal gene or gene product encoding an SK or IK channel of the present invention, for the presence or absence of an abnormal gene or gene product encoding an SK or IK channel, or quantification of the transcription levels of normal or abnormal SK or IK channel protein gene product. The kit typically includes a stable preparation of nucleic acid probes for performing the assay of the present invention. Further, the kit may also include a hybridization solution in either dry or liquid form for the hybridization of probes to target calcium-activated potassium channel proteins or calcium-activated potassium channel protein nucleic acids of the present invention, a solution for washing and removing undesirable and non-hybridized nucleic acids, a substrate for detecting the hybridization complex, and/or instructions for performing and interpreting the assay.

Expression of Nucleic Acids

Once the nucleic acids encoding an SK or IK channel protein of the present invention are isolated and cloned, one may express the desired protein in a recombinantly engineered cell such as bacteria, yeast, insect (especially employing baculoviral vectors), and mammalian cells. A "recombinant protein" is a protein produced using cells that do not have in their native form an endogenous copy of the DNA able to express the protein. The cells produce the recombinant protein because they have been genetically altered by the introduction of the appropriate isolated nucleic acid sequence (e.g., a vector comprising an SK or IK channel protein nucleic acid).

It is expected that those of skill in the art are knowledgeable in the numerous expression systems available for expression of DNA encoding SK or IK channel proteins. No attempt to describe in detail the various methods known for the expression of proteins in prokaryotes or eukaryotes will be made.

In brief summary, the expression of natural or synthetic nucleic acids encoding calcium-activated potassium channel proteins of the present invention will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the SK or IK channel protein. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to an SK or IK channel protein without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

1. Expression in Prokaryotes

Examples of regulatory regions suitable for this purpose in *E. coli* are the promoter and operator region of the *E. coli* tryptophan biosynthetic pathway as described by Yanofsky, *Bacteriol.* 158:1018–1024 (1984), and the leftward promoter of phage lambda ($P_L$) as described by Herskowitz and Hagen, *Ann. Rev. Genet.*, 14:399–445 (1980). The inclusion of selection markers in DNA vectors transfected in *E. coli* is also useful. Examples of such markers include genes specifying resistance to ampicillin, tetracycline, or chloramphenicol. See, Sambrook, et al. for details concerning selection markers for use in *E. coli*.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing SK channel proteins are available using *E. coli, Bacillus* sp. and *Salmonella* (Palva, et al., *Gene* 22:229–235 (1983); Mosbach, et al., *Nature* 302:543–545 (1983)).

When expressing SK or IK channel proteins in *S. typhimurium*, one should be aware of the inherent instability of plasmid vectors. To circumvent this, the foreign gene can be incorporated into a nonessential region of the host chromosome. This is achieved by first inserting the gene into a plasmid such that it is flanked by regions of DNA homologous to the insertion site in the *Salmonella* chromosome. After introduction of the plasmid into the *S. typhimurium*, the foreign gene is incorporated into the chromosome by homologous recombination between the flanking sequences and chromosomal DNA.

An example of how this can be achieved is based on the his operon of *Salmonella*. Two steps are involved in this process. First, a segment of the his operon must be deleted in the *Salmonella* strain selected as the carrier. Second, a plasmid carrying the deleted his region downstream of the gene encoding the SK or IK channel protein is transfected into the his *Salmonella* strain. Integration of both the his sequences and a gene encoding an SK or IK channel protein occurs, resulting in recombinant strains which can be selected as his$^+$.

Detection of the expressed protein is achieved by methods known in the art and include, for example, radioimmunoassays, Western blotting techniques or immunoprecipitation. Purification from *E. coli* can be achieved following procedures described in U.S. Pat. No. 4,511,503.

2. Expression in Eukaryotes

A variety of eukaryotic expression systems such as yeast, insect cell lines, bird, fish, frog, and mammalian cells, are known to those of skill in the art. As explained briefly below, SK or LK channel proteins of the present invention may be expressed in these eukaryotic systems. Expression of SK or IK channels in eukaryotes is particularly preferred.

Synthesis of heterologous proteins in yeast is well known. *Methods in Yeast Genetics*, Sherman, F., et al., Cold Spring Harbor Laboratory, (1982) is a well recognized work describing the various methods available to produce the protein in yeast. Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., 1979, *Gene,* 8:17–24; Broach, et al., 1979, *Gene,* 8:121–133).

Two procedures are used in transfecting yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, 1978, *Nature* (London), 275:104–109; and Hinnen, A., et al., 1978, *Proc. Natl. Acad. Sci. USA,* 75:1929–1933. The second procedure does not involve removal of the cell wall. Instead the cells are treated with lithium chloride or acetate and PEG and put on selective plates (Ito, H., et al., 1983, *J. Bact.,* 153:163–168).

The calcium-activated potassium channel proteins of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding the calcium-activated potassium channel proteins can also be ligated to various expression vectors for use in transfecting cell cultures of, for instance, mammalian, insect, bird, amphibian, or fish origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells. In some embodiments, *Xenopus* oocytes are used. Those of skill will recognize that preferred cell lines for expressing SK or IK channels substantially lack conductances which compete with those provided by the calcium-activated potassium channels of the present invention (i.e., "quiet lines"). Expression vectors for these cells can include expression control sequences, such as an origin of replication, a promoter (e.g., the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of SK channel proteins are available, for instance, from the American Type Culture Collection Catalogue of Cell Lines and Hybridomas (7th edition, 1992).

Appropriate vectors for expressing SK or IK channel proteins in insect cells are usually derived from the SF9 baculovirus. Suitable insect cell lines include mosquito larvae, silkworm, armyworm, moth and *Drosophila* cell lines such as a Schneider cell line (See Schneider *J. Embryol. Exp. Morphol.* 27:353–365 (1987).

As indicated above, the vector, e.g., a plasmid, which is used to transfect the host cell, preferably contains DNA sequences to initiate transcription and sequences to control the translation of the protein. These sequences are referred to as expression control sequences.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., 1983, *J. Virol.* 45: 773–781).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in *DNA Cloning Vol. II a Practical Approach* Ed. D. M. Glover, IRL Press, Arlington, Va. pp. 213–238.

The host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells. The transfected cells are cultured by means well known in the art. *Biochemical Methods in Cell Culture and Virology*, Kuchler, R. J., Dowden, Hutchinson and Ross, Inc., (1977). The expressed proteins are recovered by well known mechanical, chemical or enzymatic means.

Purification of Expressed Peptides

The SK or IK channel proteins of the present invention which are produced by recombinant DNA technology may be purified by standard techniques well known to those of skill in the art. Recombinantly produced SK or IK channel proteins can be directly expressed or expressed as a fusion protein. The recombinant calcium-activated potassium channel protein of the present invention is purified by a combination of cell lysis (e.g., sonication) and affinity chromatography. For fusion products, subsequent digestion of the fusion protein with an appropriate proteolytic enzyme releases the desired recombinant calcium-activated potassium channel protein.

The calcium-activated potassium channel proteins of this invention, recombinant or synthetic, may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982); Deutscher, Guide to Protein Purification, Academic Press, 1990. For example, the proteins of this invention may be purified by immunoaffinity columns using antibodies raised to the SK or IK channel proteins as described herein.

Antibodies to Calcium-Activated Potassium Channel Proteins

Antibodies are raised to the SK or IK channel protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

A. Antibody Production

A number of immunogens are used to produce antibodies specifically reactive with an SK or IK channel protein. An isolated recombinant, synthetic, or native SK or IK channel protein of 5 amino acids in length or greater, and selected from a subsequence of SEQ ID NO:1, 2, 3, 4, 19, 20, 32, 43, or 47 are the preferred immunogens (antigen) for the production of monoclonal or polyclonal antibodies. Those of skill will readily understand that the calcium-activated potassium channel proteins of the present invention are typically denatured prior to formation of antibodies for screening expression libraries or other assays in which a putative calcium-activated potassium channel protein of the present invention is expressed or denatured in a non-native secondary, tertiary, or quarternary structure. Exemplary proteins for use as immunogens include, but are not limited to, GHRRALFEKRKRLSDY (SEQ ID NO:28), FTDASSRSIGAL (SEQ ID NO:29), ARKLELTKAEKHVHNFMMDTQLTKR (SEQ ID NO:30), and ARKLELTKAEKHVHNFMMDTQLTK (SEQ ID NO:42). In one class of preferred embodiments, an immunogenic protein conjugate is also included as an immunogen. Naturally occurring SK or IK channel proteins are also used either in pure or impure form.

The SK or IK channel protein is then injected into an animal capable of producing antibodies. Either monoclonal or polyclonal antibodies can be generated for subsequent use in immunoassays to measure the presence and quantity of the calcium-activated potassium channel protein. Methods of producing polyclonal antibodies are known to those of skill in the art. In brief, an immunogen (antigen), preferably a purified SK or IK channel protein, an SK or IK channel protein coupled to an appropriate carrier (e.g., GST, keyhole limpet hemanocyanin, etc.), or an SK or IK channel protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the calcium-activated potassium channel protein of interest. When appropriately high titers of antibody to the immunogen are obtained, blood is collected from the animal and antisera are prepared. Further fractionation of the antisera to enrich for antibodies reactive to the SK or IK channel protein is performed where desired (see, e.g., Coligan (1991) *Current Protocols in Immunology* Wiley/Greene, NY; and Harlow and Lane (1989) *Antibodies: A Laboratory Manual* Cold Spring Harbor Press, NY).

Antibodies, including binding fragments and single chain recombinant versions thereof, against predetermined fragments of SK or IK channel protein are raised by immunizing animals, e.g.. with conjugates of the fragments with carrier proteins as described above. Typically, the immunogen of interest is an SK or IK channel protein of at least about amino acids, more typically the SK or IK channel protein is 10 amino acids in length, preferably, 15 amino acids in length and more preferably the calcium-activated potassium channel protein is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonals antibodies are screened for binding to an SK or IK channel protein from which the immunogen was derived. Specific monoclonal and polyclonal antibodies will usually bind with a $K_D$ of at least about 0.1 mM, more usually at least about 50 $\mu$M, and most preferably at least about 1 $\mu$M or better.

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen comprising an SK or IK channel protein. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transfection with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The SK or IK channel proteins and antibodies of the present invention are used with or without modification, and include chimeric antibodies such as humanized murine antibodies.

Other suitable techniques involve selection of libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology*, 14: 309–314). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14:845–851 (1996).

Frequently, the SK or IK channel proteins and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad. Sci. USA* 86: 10029–10033.

The antibodies of this invention are also used for affinity chromatography in isolating SK or IK channel proteins. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified SK or IK channel protein are released.

The antibodies can be used to screen expression libraries for particular expression products such as normal or abnormal human SK or IK channel protein. Usually the antibodies in such a procedure are labeled with a moiety allowing easy detection of presence of antigen by antibody binding.

Antibodies raised against SK or IK channel protein can also be used to raise anti-idiotypic antibodies. These are useful for detecting or diagnosing various pathological conditions related to the presence of the respective antigens.

B. Human or Humanized (Chimeric) Antibody Production

The anti-SK or anti-IK channel protein antibodies of this invention can also be administered to a mammal (e.g., a human patient) for therapeutic purposes (e.g., as targeting molecules when conjugated or fused to effector molecules such as labels, cytotoxins, enzymes, growth factors, drugs, etc.). Antibodies administered to an organism other than the species in which they are raised are often immunogenic. Thus, for example, murine antibodies administered to a human often induce an immunologic response against the antibody (e.g., the human anti-mouse antibody (HAMA) response) on multiple administrations. The immunogenic properties of the antibody are reduced by altering portions, or all, of the antibody into characteristically human sequences thereby producing chimeric or human antibodies, respectively.

i) Humanized (Chimeric) Antibodies

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos.: 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369). Detailed methods for preparation of chimeric (humanized) antibodies can be found in U.S. Pat. No. 5,482,856.

ii) Human Antibodies

In another embodiment, this invention provides for fully human anti-SK channel protein antibodies. Human antibodies consist entirely of characteristically human polypeptide sequences. The human anti-SK or anti-IK channel protein antibodies of this invention can be produced in using a wide variety of methods (see, e.g., Larrick et al., U.S. Pat. No. 5,001,065, for review).

In preferred embodiments, the human anti-SK channel protein antibodies of the present invention are usually produced initially in trioma cells. Genes encoding the antibodies are then cloned and expressed in other cells, particularly, nonhuman mammalian cells. The general approach for producing human antibodies by trioma technology has been described by Ostberg et al. (1983), *Hybridoma* 2: 361–367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

The genes encoding the heavy and light chains of immunoglobulins secreted by trioma cell lines are cloned according to methods, including the polymerase chain reaction, known in the art (see, e.g., Sambrook et al., *Molecular Cloning: A Laboratory Manual*, 2nd ed., Cold Spring Harbor, N.Y., 1989; Berger & Kimmel, *Methods in Enzymology*, Vol. 152: *Guide to Molecular Cloning Techniques*, Academic Press, Inc., San Diego, Calif., 1987; Co et al. (1992) *J. Immunol.*, 148: 1149). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Calcium-Activated Potassium Channel Protein Immunoassays

Immunoassays for SK and IK channel proteins can be used for at least two different purposes. They can be used to determine the relatedness of the protein by virtue of their being able to cross-react immunologically or for detection of the presence or absence of the channel proteins.

When determining if an unknown protein is related to the channel proteins of this invention, a variety of assays can be used. For example and preferred is a competitive immunoassay to test for cross-reactivity. For example, the protein of SEQ ID NO:2 or 32 can be immobilized to a solid support. Proteins or peptides are added to the assay which compete with the binding of the antisera to the immobilized antigen. The ability of the above proteins to compete with the binding of the antisera to the immobilized protein is compared to the protein thought to be related to the test protein.

To assure that the antisera being tested is specific or selectively binding to a particular protein, it will be tested for cross-reactivity to other closely related proteins. This allows for the production of sera that will distinguish between small, intermediate and large conductance channels. The percent crossreactivity for the above proteins can be calculated, using standard calculations. Those antisera with less than 10% crossreactivity with each of the proteins listed above are selected and pooled. The cross-reacting antibodies are optionally removed from the pooled antisera by immunoabsorption with the above-listed proteins.

The immunoabsorbed and pooled antisera are then used in a competitive binding immunoassay as described above to compare a second protein to the claimed or prototype immunogen protein. In order to make this comparison, the two proteins are each assayed at a wide range of concentrations and the amount of each protein required to inhibit 50% of the binding of the antisera to the immobilized protein is determined. If the amount of protein required is less than twice the amount of the prototype protein, then the second protein is said to specifically bind to an antibody generated to the prototype immunogen. Where the antibodies are generated to a short peptide, the test proteins are optionally denatured to fully test for selective binding. In situations where the target peptide is not readily accessible to the antibodies because the target peptide is part of a larger protein, it is proper to measure the relatedness of test proteins against prototype proteins of similar size, e.g., one would test a full length monomer against a prototype, fill length monomer even though the antisera was generated against a peptide of the prototype monomer. This simplifies the reading of the test results and avoids having to take into account conformational problems and molecular weight/molar concentrations in the determination of the data generated from the competitive immunoassays.

Means of detecting the SK or IK channel proteins of the present invention are not critical aspects of the present invention. In a preferred embodiment, the SK or IK channel proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume 37: Antibodies in Cell Biology*, Asai, ed. Academic Press, Inc. New York (1993); *Basic and Clinical Immunology* 7th Edition, Stites & Terr, eds. (1991). Immunological binding assays (or immunoassays) typically utilize a "capture agent" to specifically bind to and often immobilize the analyte (in this case a calcium-activated potassium channel protein). The capture agent is a moiety that specifically binds to the analyte. In a preferred embodiment, the capture agent is an antibody that specifically binds a calcium-activated potassium channel protein(s) of the present invention. The antibody (anti-SK or anti-IK channel protein antibody) may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled SK or IK channel protein or a labeled anti-SK or anti-IK channel protein antibody. Alternatively, the labeling agent may be a third moiety, such as another antibody, that specifically binds to the antibody/SK or antibody/IK channel protein complex.

In a preferred embodiment, the labeling agent is a second SK or IK channel protein antibody bearing a label. Alternatively, the second SK or IK channel protein antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 11: 1401–1406, and Akerstrom, et al. (1985) *J. Immunol.*, 135: 2589–2542).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting an SK or IK channel protein in a biological sample generally comprises the steps of contacting the biological sample with an antibody which specifically reacts, under immunologically reactive conditions, to the SK or IK channel protein. The antibody is allowed to bind to the SK or IK channel protein under immunologically reactive conditions, and the presence of the bound antibody is detected directly or indirectly.

A. Non-Competitive Assay Formats

Immunoassays for detecting SK or IK channel proteins of the present invention include competitive and noncompetitive formats. Noncompetitive immunoassays are assays in which the amount of captured analyte (in this case an SK or IK channel protein) is directly measured. In one preferred "sandwich" assay, for example, the capture agent (anti-SK or anti-IK channel protein antibodies) can be bound directly to a solid substrate where they are immobilized. These immobilized antibodies then capture SK or IK channel protein present in the test sample. The SK or IK channel protein thus immobilized is then bound by a labeling agent, such as a second human SK or IK channel protein antibody bearing a label. Alternatively, the second SK or IK channel protein antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

B. Competitive Assay Formats

In competitive assays, the amount of analyte (SK or IK channel protein) present in the sample is measured indirectly by measuring the amount of an added (exogenous) analyte (SK or IK channel protein) displaced (or competed away) from a capture agent (anti-SK or anti-IK channel protein antibody) by the analyte present in the sample. In one competitive assay, a known amount of, in this case, SK or IK channel protein is added to the sample and the sample is then contacted with a capture agent, in this case an antibody that specifically binds the SK or IK channel protein. The amount of SK or IK channel protein bound to the antibody is inversely proportional to the concentration of SK or IK channel protein present in the sample.

In a particularly preferred embodiment, the antibody is immobilized on a solid substrate. The amount of SK or IK channel protein bound to the antibody may be determined either by measuring the amount of SK or IK channel protein present in the corresponding SK or IK channel protein/antibody complex, or alternatively by measuring the amount of remaining uncomplexed SK or IK channel protein. The amount of SK or IK channel protein may be detected by providing a labeled SK or IK channel protein molecule.

A hapten inhibition assay is another preferred competitive assay. In this assay a known analyte, in this case the SK or IK channel protein is immobilized on a solid substrate. A known amount of anti-SK or anti-IK channel protein antibody, respectively, is added to the sample, and the sample is then contacted with the immobilized SK or IK channel protein. In this case, the amount of anti-SK or anti-IK channel protein antibody bound to the immobilized SK or IK channel protein is inversely proportional to the amount of SK or IK channel protein present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

C. Other Assay Formats

In a particularly preferred embodiment, Western blot (immunoblot) analysis is used to detect and quantify the presence of an SK or IK channel protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind SK channel protein. The anti-SK or anti-IK channel protein antibodies specifically bind to the SK or IK channel proteins, respectively, on the solid support. These antibodies may be directly labeled or alternatively may be subsequently detected using labeled antibodies (e.g., labeled sheep anti-mouse antibodies) that specifically bind to the anti-SK or anti-IK channel protein.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34–41).

D. Labels

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, radioisotopic, electrical, optical or chemical means. Useful labels in the present invention include those used in labeling of nucleic acids as discussed, supra.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Immunoassay Detection Kits

The present invention also provides for kits for the diagnosis of organisms (e.g., patients) with a deficiency in the levels of expressed SK or IK channel protein. The kits preferably include one or more reagents for detecting an the amount of SK or IK channel protein in a mammal. Preferred reagents include antibodies that specifically bind to normal SK or IK channel proteins or subsequences thereof. The antibody may be free or immobilized on a solid support such as a test tube, a microwell plate, a dipstick and the like. The kit may also contain instructional materials teaching the use of the antibody in an assay for the detection of SK or IK channel protein. The kit may contain appropriate reagents for detection of labels, positive and negative controls, washing solutions, dilution buffers and the like.

Assays for Compounds that Increase or Decrease K$^+$ Flux

Isolated SK or IK channel nucleic acids of the present invention which are expressed in cells can be used in a variety of assays to detect compounds that increase or decrease the flux (i.e., influx or efflux) of potassium through the SK or IK channels, respectively. Generally, compounds that decrease potassium ion flux will cause a decrease by at least 10% or 20%, more preferably by at least 30%, 40%, or 50%, and most preferably by at least 70%, 80%, 90% or 100%. Compounds that increase the flux of potassium ions will cause a detectable increase in the potassium ion current density by increasing the probability of a SK or IK channel being open and allowing the passage of potassium ions. Typically the flux will increase by at least 20%, 50%, 100%, or 200%, often by at least 400%, 600%, 1,000%, 5,000% or 10,000%. Increased or decreased flux of potassium may be assessed by determining changes in polarization (i.e., electrical potential) of the cell expressing the SK or IK channel. A particularly preferred means to determine changes in cellular polarization is the voltage-clamp technique. Whole cell currents are conveniently determined using the conditions set forth in Example 3. Other known assays include: radiolabeled rubidium flux assays and fluorescence assays using voltage-sensitive dyes. See, e.g., Vestergarrd-Bogind et al., *J. Membrane Biol.,* 88:67–75 (1988); Daniel et al., *J. Pharmacol. Meth.,* 25:185–193 (1991); Holevinsky et al., *J. Membrane Biology,* 137:59–70 (1994). Assays for compounds capable of inhibiting or increasing potassium flux through the SK channel protein can be performed by application of the compounds to a bath solution in contact with and comprising cells having an SK or IK channel of the present invention. See, e.g., Blatz et al., *Nature,* 323:718–720 (1986); Park,*J. Physiol.,* 481:555–570 (1994). Generally, the compounds to be tested are present in the range from 1 pM to 100 mM. Changes in function of the channels can be measured in the electrical currents or ionic flux, or by the consequences of changes in currents and flux.

The effects of the test compounds upon the function of the channels can be measured by changes in the electrical currents or ionic flux or by the consequences of changes in currents and flux. Changes in electrical current or ionic flux are measured by either increases or decreases in flux of cations such as potassium or rubidium ions. The cations can be measured in a variety of standard ways. They can be measured directly by concentration changes of the ions or indirectly by membrane potential or by radiolabeling of the ions. Consequences of the test compound on ion flux can be quite varied. Accordingly, any suitable physiological change can be used to assess the influence of a test compound on the channels of this invention. Changes in channel function can be measured by ligand displacement such as CTX release. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immuno-responses (e.g., T cell activation), changes in cell metabolism such as cell growth or pH changes.

Preferably, the SK channel of the assay will be selected from a channel protein of SEQ ID NOS:1, 2, 3, 4, 19, 20, 43 or 47 or conservatively modified variant thereof. An IK channel of the assay will preferably have a sequence as shown in SEQ ID NO:32, or conservatively modified variant thereof. Alternatively, the SK channel of the assay will be derived from a eukaryote and include an amino acid subsequence having sequence similarity to the core region of SK channel proteins of SEQ ID NOS:1 through 4, 19, 20, 43 and/or 47. The IK will typically be derived from a eukaryote and include an amino acid subsequence having sequence similarity to the core region of IK channel proteins of SEQ ID NO:32. Generally, the functional SK or IK channel protein will be at least 400, 450, 500, or 550 amino acids in length. The percentage of sequence similarity with the core region of a protein selected from the group consisting of: SEQ ID NO:1, 2, 3, 4, 19, 20, 32, 43 and 47 will be any one of the integers between 60 and 100. Generally, the sequence similarity will be at least 60%, typically at least 70%, generally at least 75%, preferably at least 80%, more preferably at least 85%, most preferably at least 90%, and often at least 95%. Thus, SK channel homologs will hybridize, under moderate hybridization conditions, to a nucleic acid of at least 300 nucleotides in length from the core region of a nucleic acid selected from the group consisting of SEQ ID NOS:13, 14, 15, 16, 21, 22, and complementary sequences thereof. IK channel homologs will hybridize, under moderate hybridization conditions, to a nucleic acid of at least 300 nucleotides in length from the core region of a nucleic acid such as SEQ ID NO:31.

The "core region" or "core sequence" of SEQ ID NOS:13–16, 21, 22, 44 and 48 corresponds to the encoded region of alignment between SEQ ID NOS: 1, 2, 3, 4, 19, 20, 43, and 47 with and from rSK2 (SEQ ID NO:2) amino acid residue 135 to 462. The core region of hIK1 is from amino acid residue 25 through residue 351. In preferred embodiments, the SK channel will have at least 90% sequence similarity, as compared to the core sequence from a sequence of ID NO: 1, 2, 3, 4, 19, 20, 43, or 47 over a comparison window of any of from any one of 20 contiguous amino acid residues to 300 contiguous amino acid residues from within the core region. In preferred embodiments, the IK channel will have at least 90% sequence similarity, as compared to the core sequence of SEQ ID NO:32, over a comparison window of any of from any one of 20 contiguous amino acid residues to 300 contiguous amino acid residues from within the core region.

The SK channel homologs will generally have substantially similar conductance characteristics (e.g., 2–60 pS) and calcium sensitivities (30 nM–10 $\mu$M). IK channel homologs will likewise have similar SK channels conductance characteristics as a IK channel (e.g., 20–80 pS) and calcium sensitivities (30 nM–10 $\mu$M). Chimeras formed by expression of at least two of SEQ ID NOS:1, 2, 3, 4, 19, 20, or 32 can also be used. In a preferred embodiment, the cell placed in contact with a compound which is assayed for increasing or decreasing potassium flux is a eukaryotic cell, more preferably an oocyte of *Xenopus* (e.g., *Xenopus laevis*).

Yet another assay for compounds that increase or decrease potassium flux in calcium activated potassium channels involves "virtual genetics," in which a computer system is used to generate a three-dimensional structure of SK and IK proteins based on the structural information encoded by the amino acid sequence. The amino acid sequence interacts directly and actively with a preestablished algorithm in a computer program to yield secondary, tertiary, and quaternary structural models of the protein. The models of the protein structure are then examined to identify regions of the structure that have the ability to bind to ligands. These regions are then used to identify ligands that bind to the protein.

The three-dimensional structural model of the protein is generated by inputting channel protein amino acid sequences or nucleic acid sequences encoding a channel protein into the computer system. The amino acid sequence of the channel protein is selected from the group consisting of: SEQ ID NOS: 1, 2, 3, 4, 19, 20, 32, 43, 47, and conservatively modified versions thereof. The amino acid sequence represents the primary sequence of the protein, which encodes the structural infomation of the protein. The amino acid sequence is input into the computer system from computer readable substrates that include, but are not limited to, electronic storage media (e.g., magnetic diskettes, tapes, cartridges, and chips), optical media (e.g., CD ROM, telephone lines), addresses to internet sites, and RAM. The three-dimensional structural model of the channel protein is then generated by the interaction of the amino acid sequence and the computer system. The software is commercially available programs such as Biopolymer, Quanta, and Insight.

The amino acid sequence represents a primary structure that encodes the information necessary to form the secondary, tertiary and quaternary structure of the protein. The software looks at certain parameters encoded by the primary sequence to generate the structural model. These parameters are refered to as "energy terms," and primarily include electrostatic potential, hydrohobic potential, solvent accessible surface, and hydrogen bonding. Secondary energy terms include van der Waals potential. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can input additional variables such as whether the protein is membrane bound or soluble, its location in the body, and whether it is cytoplasmic, surface, or nuclear. These variables along with the energy terms of the secondary structure are used to form the model of the teritary structure. In modeling the tertiary structure, the computer program matches hydrophobic protein faces of secondary structure with like, and hydrophilic secondary structure with like.

Finally, quaternary structure of multi-subunit proteins can be modeled in a similar fashion, using anisotrophy terms. These terms interface different protein subunits to energetically minize the interaction of the subunits. In the case of channel proteins, typically four identical subunits make up the quaternary structure of the channel.

Once the structure has been generated, potential ligand binding regions are identified by the computer system. Three-dimensional structures for potential ligands are generated by inputting amino acid and nucleotide sequences or chemical formulas of compounds, as described above. The three-dimensional structure of the potential ligand is then compared to that of the channel protein to identify ligands that bind to the channel protein. Binding affinity between the protein and ligands is determined using energy terms to determine which ligands have an enhanced probability of binding to the protein.

Computer systems are also used to screen for mutations of SK and IK genes. Such mutations can be associated with disease states. Once the mutations are identified, diagnostic assays can be used to identify patients having such mutated genes associated with disease states. Identification of the mutated SK and IK genes involves receiving input of a first nucleic acid sequence encoding a calcium channel protein having an amino acid sequence selected from the group consisting of SEQ ID NOS:1, 2, 3, 4, 20, 32, 43, 47, and conservatively modified versions thereof. The sequence is input into the compter system as described above. The first nucleic acid sequence is then compared to a second nucleic acid sequence that has substantial identity to the first nucleic acid sequence. The second nucleic acid sequence is input into the computer system in the manner described above. Once the first and sequence sequences are compared, nucleotide differences between the sequences are identified. Such sequences can represent allelic differences in SK and IK genes, and mutations associated with disease states.

Cellular Transfection and Gene Therapy

The present invention provides packageable SK and IK channel protein nucleic acids (cDNAs), supra, for the transfection of cells in vitro and in vivo. These packageable nucleic acids can be inserted into any of a number of well known vectors for the transfection of target cells and organisms as described below. The nucleic acids are transfected into cells, ex vivo or in vivo, through the interaction of the vector and the target cell. The SK or IK channel protein nucleic acid, under the control of a promoter, then expresses the calcium-activated potassium channel protein of the present invention thereby mitigating the effects of absent, partial inactivation, or abnormal expression of the SK or IK channel protein gene.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies. As an example, in vivo expression of cholesterol-regulating genes, genes which selectively block the replication of HIV, and tumor-suppressing genes in human patients dramatically improves the treatment of heart disease, AIDS, and cancer, respectively. For a review of gene therapy procedures, see Anderson, *Science* (1992) 256:808–813; Nabel and Felgner (1993) *TIBTECH* 11: 211–217; Mitani and Caskey (1993) *TIBTECH* 11: 162–166; Mulligan (1993) *Science* 926–932; Dillon (1993) *TIBTECH* 11: 167–175; Miller (1992) *Nature* 357: 455–460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in *Current Topics in Microbiology and Immunology* Doerfler and Böhm (eds) Springer-Verlag, Heidelberg Germany; and Yu et al., *Gene Therapy* (1994) 1:13–26.

Delivery of the gene or genetic material into the cell is the first critical step in gene therapy treatment of disease. A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Natl. Acad. Sci. USA* 84: 7413–7414), and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4:43, and Cornetta et al. *Hum. Gene Ther.* 2:215 (1991)). Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol* 63:2374–2378; Miller et al., *J. Virol.* 65:2220–2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra).

AAV-based vectors are also used to transduce cells with target nucleic acids, e.g., in the in vitro production of nucleic acids and peptides, and in in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.*, 4:2072–2081; Hermonat and Muzyczka (1984) *Proc. Natl. Acad. Sci. USA*, 81:6466–6470; McLaughlin et al. (1988) and Samulski et at. (1989) *J. Virol.*, 63:03822–3828. Cell lines that can be transfected by rAAV include those described in Lebkowski et al. (1988) *Mol. Cell. Biol.*, 8:3988–3996.

A. Ex vivo Transfection of Cells

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with an SK or IK channel protein nucleic acid (gene or cDNA), and re-infused back into the subject organism (e.g., patient). Various cell types suitable for ex vivo transfection are well known to those of skill in the art (see, e.g., Freshney et al., *Culture of Animal Cells, a Manual of Basic Technique, third edition* Wiley-Liss, New York (1994)) and the references cited therein for a discussion of how to isolate and culture cells from patients).

As indicated above, in a preferred embodiment, the packageable nucleic acid which encodes an SK or IK channel protein is under the control of an activated or constitutive promoter. The transfected cell(s) express a functional SK or IK channel protein which mitigates the effects of deficient or abnormal SK or IK channel protein gene expression.

In one particularly preferred embodiment, stem cells are used in ex-vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating $CD34^+$ cells in vitro into clinically important immune cell types using cytokines such a GM-CSF, IFN-γ and TNF-α are known (see, Inaba et al. (1992) *J. Exp. Med.* 176, 1693–1702, and Szabolcs et al. (1995) 154: 5851–5861).

Stem cells are isolated for transduction and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as $CD4^+$ and $CD8^+$ (T cells), $CD45^+$ (panB cells), GR-1 (granulocytes), and lad (differentiated antigen presenting cells). For an example of this protocol see, Inaba et al. (1992) *J. Exp. Med.* 176, 1693–1702.

In humans, bone marrow aspirations from iliac crests are performed e.g., under general anesthesia in the operating room. The bone marrow aspirations is approximately 1,000 ml in quantity and is collected from the posterior iliac bones and crests. If the total number of cells collected is less than about $2 \times 10^8$/kg, a second aspiration using the sternum and anterior iliac crests in addition to posterior crests is performed. During the operation, two units of irradiated packed red cells are administered to replace the volume of marrow taken by the aspiration. Human hematopoietic progenitor and stem cells are characterized by the presence of a CD34 surface membrane antigen. This antigen is used for purification, e.g., on affinity columns which bind CD34. After the bone marrow is harvested, the mononuclear cells are separated from the other components by means of ficol gradient centrifugation. This is performed by a semi-automated method using a cell separator (e.g.. a Baxter Fenwal CS3000+ or Terumo machine). The light density cells, composed mostly of mononuclear cells are collected and the cells are incubated in plastic flasks at 37° C. for 1.5 hours. The adherent cells (monocytes, macrophages and B-Cells) are discarded. The non-adherent cells are then collected and incubated with a monoclonal anti-CD34 antibody (e.g., the murine antibody 9C5) at 4° C. for 30 minutes with gentle rotation. The final concentration for the anti-CD34 antibody is 10 μg/ml. After two washes, paramagnetic microspheres (Dyna Beads, supplied by Baxter Immunotherapy Group, Santa Ana, Calif.) coated with sheep anti-mouse IgG (Fc) antibody are added to the cell suspension at a ratio of 2 cells/bead. After a further incubation period of 30 minutes at 4° C., the rosetted cells with magnetic beads are collected with a magnet. Chymopapain (supplied by Baxter Immunotherapy Group, Santa Ana, Calif.) at a final concentration of 200 U/ml is added to release the beads from the CD34+ cells. Alternatively, and preferably, an affinity column isolation procedure can be used which binds to CD34, or to antibodies bound to CD34 (see, the examples below). See, Ho et al. (1995) *Stem Cells* 13 (suppl. 3): 100–105. See also, Brenner (1993) *Journal of Hematotherapy* 2: 7–17.

In another embodiment, hematopoetic stem cells are isolated from fetal cord blood. Yu et al. (1995) *Proc. Natl. Acad. Sci. USA*, 92: 699–703 describe a preferred method of transducing $CD34^+$ cells from human fetal cord blood using retroviral vectors.

B. In vivo Transfection

Vectors (e.g., retroviruses, adenoviruses, liposomes, etc.) containing therapeutic nucleic acids can be administered directly to the organism for transduction of cells in vivo. Administration is by any of the routes normally used for introducing a molecule into ultimate contact with blood or tissue cells. The packaged nucleic acids are administered in any suitable manner, preferably with pharmaceutically acceptable carriers. Suitable methods of administering such packaged nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

The packaged nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose scaled containers, such as ampules and vials.

Injection solutions and suspensions can be prepared from sterile powders, granules, and tablets of the kind previously described. Cells transduced by the packaged nucleic acid as described above in the context of ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of SK or IK channel protein, the physician evaluates circulating plasma levels of the vector, vector toxicities, progression of the disease, and the production of anti-vector antibodies. In general, the dose equivalent of a naked nucleic acid from a vector is from about 1 $\mu$g to 100 $\mu$g for a typical 70 kilogram patient, and doses of vectors which include a retroviral particle are calculated to yield an equivalent amount of therapeutic nucleic acid.

For administration, inhibitors and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

In a preferred embodiment, prior to infusion, blood samples are obtained and saved for analysis. Between $1\times10^8$ and $1\times10^{12}$ transduced cells are infused intravenously over 60–200 minutes. Vital signs and oxygen saturation by pulse oximetry are closely monitored. Blood samples are obtained 5 minutes and 1 hour following infusion and saved for subsequent analysis. Leukopheresis, transduction and reinfusion can be repeated are repeated every 2 to 3 months. After the first treatment, infusions can be performed on a outpatient basis at the discretion of the clinician. If the reinfusion is given as an outpatient, the participant is monitored for at least 4, and preferably 8 hours following the therapy.

Transduced cells are prepared for reinfusion according to established methods. See, Abrahamsen et al. (1991) *J. Clin. Apheresis,* 6: 48–53; Carter et al. (1988) *J. Clin. Arpheresis,* 4:113–117; Aebersold et al. (1988) *J. Immunol. Meth.,* 112: 1–7; Muul et al. (1987) *J. Immunol. Methods,*101:171–181 and Carter et al. (1987) *Transfusion* 27: 362–365. After a period of about 2–4 weeks in culture, the cells should number between $1\times10^8$ and $1\times10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

Although the present invention has been described in some detail by way of illustration and example for purposes of clarity of understanding, it will be obvious that certain changes and modifications may be practiced within the scope of the appended claims.

EXAMPLE 1

Example 1 describes the isolation and sequencing of clones encoding small and intermediate conductance, calcium-dependent potassium channels.

A. Small conductance potassium channels, with the exception of the minK protein (Takumi et al., *Science*, 242:1042–1045 (1988), share a common structural motif within the pore region including the sequence which dictates the characteristic selectivity sequence for monovalent cations (Heginbotham et al., *Biophys. J.*, 66:1061–1067 (1994)).

A BLAST search of the EST database using the query sequence FXSIPXXXWWAXVTMTTVGYGDMXP (SEQ ID NO:45), allowing for mismatches, retrieved known potassium channel sequences and Genbank #M62043. Oligonucleotides corresponding to nucleotides 6–36 (sense) and 258–287 (antisense) of #M62043 were synthesized (Genosys, The Woodlands, Tex.), radiolabeled using polynucleotide kinase (BRL) and $^{32}$P-ATP (NEN), and used to screen ~$10^6$ recombinant phage from the human hippocampal cDNA library (40% formamide; 1 M NaCl, 1% SDS, 37° C.; washed at 1xSSC, 50° C.). Double positively hybridizing phage were purified by rescreening at reduced densities. cDNA inserts were subcloned into M13 and the nucleotide sequences determined using the dideoxy chain termination method and T7 DNA polymerase (Sequenase, UBI). A fragment of this clone containing the pore domain (amino acids 325–522) was radiolabeled using random primers (Boehringer) and used to screen a rat brain cDNA library (30% formamide, 1 M NaCl, 1% SDS, 37° C.; washed at 2xSSC, 50° C.). Positively hybridizing phage were purified and the nucleotide sequences of the inserts determined. Computer analyses were performed using the GCG software suite (Genetics Computer Group; version 8.1).

In addition to known potassium channels, one of the detected sequences from human hippocampus suggested it may contain the consensus motif, but included several ambiguities (Genbank #M62043). Based upon this sequence, oligonucleotides were synthesized having the sequence represented by nucleotides 6 to 36 of the sense strand; and nucleotides 258 to 287 of the antisense strand. The oligonucleotides were used to probe a human hippocampal cDNA library.

A full length coding sequence, hSK1 (SEQ ID NO:13), was isolated and analyzed for open reading frames, Kozak consensus sequences, potential transmembrane domains, and predicted protein structure. A fragment containing the putative pore region was radiolabelled by random priming and subsequently used to probe a rat brain cDNA library using a hybridization solution of 40% formamide, 1 M NaCl, 1% SDS, and 100 µg/ml yeast RNA, at 37° C. and washed using 0.5xSSC at 55° C. Two clones containing different full length coding sequences were isolated and analyzed: rSK2 (SEQ ID NO:15), and rSK3 (SEQ ID NO:16). In addition, a partial clone was identified representing the rat homolog of hSK1 (rSK1 (SEQ ID NO:14)).

The sequences predict proteins of 561 amino acids for hSK1 (SEQ ID NO:1), 580 amino acids for rSK2 (SEQ ID NO:2), and 553 amino acids for rSK3 (SEQ ID NO:3) which contain no stretches of homology (i.e., no signal above background under low stringency conditions) with other cloned potassium channels apart from a 12 amino acid sequence in the putative pore region. Hydrophobicity analysis predicts six transmembrane segments with the N- and C-termini residing inside the cell. The sequences are highly conserved across their transmembrane cores (80–90% identity), but diverge in sequence and length within their N- and C-terminal domains (Table 1).

TABLE 1

```
rSK2  ..........  ........MS  SCRYNGGVMR  PLSNLSSSRR  NLHEMDSEAQ
rSK3  ..........  ........MS  SCKYSGGVMK  PLSRLSASRR  NLIEAEPEGQ
rSK1  ..........  ..........  ..........  ..........  ..........
hSK1  MPGPRAACSE  PNPCTQVVMN  SHSYNGSVGR  P...LGSGPG  ALGRDPPDPE rSK2  PLQPPASVVG  GGGGASSPSA  AAAASSSAPE  IVVSKPEHNN  SNNLALYGTG
rSK3  PLQLF.....  ..........  ...SPSNPPE  IIISSREDNH  AHQTLLHHPN
rSK1  ..........  ..........  ..........  ..........  ..........
hSK1  AGHPPQPPHS  PGLQVVVAKS  EPARPSPGSP  RGQPQDQDDD  EDDEEDEAGR rSK2  GGGSTGGGGG  GGGGGGGSGH  GSSSGTKSSK  KKNQNIGYKL  GHRRALFEKR
rSK3  ATHNHQHAGT  TAGSTTFP..  ......KANK  RKNQNIGYKL  GHRRALFEKR
rSK1  ..........  ..........  .........S  GKPPTVSHRL  GHRRALFEKR
hSK1  QR........  ..........  ........AS  GKPSNVGHRL  GHRRALFEKR rSK2  KRLSDYALIF  GMFGIVVMVI  ETELSWGAYD  KASLYSLALK  CLISLSTIIL
rSK3  KRLSDYALIF  GMFGIVVMVI  ETELSWGLYS  KDSMFSLALK  CLISLSTIIL
rSK1  KRLSDYALIF  GMFGIVVMVT  ETELSWGVYT  KESLCSFALK  CLISLSTVIL
hSK1  KRLSDYALIF  GMEGIVVMVT  ETELSWGVYT  KESLYSFALK  CLISLSTAIL rSK2  LGLIIVYHAR  EIQLFMVDNG  ADDWRIAMTY  ERIFFICLEI  LVCAIHPIPG
rSK3  LGLIIAYHTR  EVQLFVIDNG  ADDWRIAMTY  ERILYISLEM  LVCAIHPIPG
rSK1  LGLVILYHAR  EIQLFLVDNG  ADDWRIAMTW  ERVSLISLEL  AVCAIHPVPG
hSK1  LGLVVLYHAR  EIQLFMVDNG  ADDWRIAMTC  ERVFLISLEL  AVCAIHPVPG rSK2  NYTFTWTARL  AFSYAPSTTT  ADVDIILSIP  MFLRLYLIAR  VMLLHSKLFT
rSK3  EYKFFWTARL  AFSYTPSRAE  ADVDIILSIP  MFLRLYLIAR  VMLLHSKLFT
rSK1  HYRFTWTARL  AFSLVPSAAE  ADVDVLLSIP  MFLRLYLLAR  VMLLHSRIFT
hSK1  HYRFTWTARL  AFTYAPSVAE  ADVDVLLSIP  MFLRLYLLGR  VMLLHSKIFT rSK2  DASSRSIGAL  NKINFNTRFV  MKTLMTICPG  TVLLVFSISL  WIIAAWTVRA
rSK3  DASSRSIGAL  NKINFNTRFV  MKTLMTICPG  TVLLMFSISL  WIIAAWTVRV
rSK1  DASSRSIGAL  NRVTFNTRFV  TKTLMTICPG  TVLLVFSISS  WIVAAWTVRV
hSK1  DASSRSIGAL  NKITFNTRFV  MKTLMTICPG  TVLLVFSISS  WIIAAWTVRV
```

TABLE 1-continued

```
rSK2  CERYHDQQDV  TSNFLGAMWL  ISITFLSIGY  GDMVPNTYCG  KGVCLLTGIM
rSK3  CERYHDQQDV  TSNFLGAMWL  ISITFLSIGY  GDMVPHTYCG  KGVCLLTGIM
rSK1  CERYHDKQEV  TSNFLGAMWL  ISITELSIGY  GDMVPHTYCG  KGVCLLTGIM
hSK1  CERYHDKQEV  TSNFLGAMWL  ISITFLSIGY  GDMVPHTYCG  KGVCLLTGIM rSK2  GAGCTALVVA  VVARKLELTK  AEKHVHNFMM  DTQLTKRVKN  AAANVLRETW
rSK3  GAGCTALVVA  VVARKLELTK  AEKHVMNFMM  DTQLTKRIKN  AAANVLRETW
rSK1  GAGCTALVVA  VVARKLELTK  AEKHVHNFMM  DTQLTKRVKN  AAANVLRETW
hSK1  GAGCTALVVA  VVARKLELTK  AEKHVHNFMM  DTQLTKRVKN  AAANVLRETW rSK2  LIYKNTKLVK  KIDHAKVRKH  QRKFLQAIHQ  ...LRSVKME  QRKLNDQANT
rSK3  LIYKHTKLLK  KIDHAKVRKH  QRKFLQAIHQ  ...LRGVKME  QRKLSDQANT
rSK1  LIYKHTRLVK  KPDQSRVAKH  QRKFLQAIHQ  AQKLRTVKIE  QGKVNDQANT
hSK1  LIYKHTRLVK  KPDQARVRKH  QRKFLQAIHQ  AQKLRSVKIE  QGKLNDQANT rSK2  LVDLAKTQNI  MYDMISDLNE  RSEDFEKRIV  TLETKLETLI  GSIHALPGLI
rSK3  LVDLSKMQNV  MYDLITELND  RSEDLEKQIG  SLESKLEHLT  ASFNSLPLLI
rSK1  LADLAKAQSI  AYEVVSELQA  QQEELEARLA  ALESRLDVLG  ASLQALPSLI
hSK1  LTDLAKTQTV  MYDLVSELHA  QHEELEARLA  TLESRLDALG  ASLQALPGLI rSK2  SQTI....RQ  QQRDFIETQM  ENYDKHVTYN  AERSRSSSRR  RRSSSTAPPT
rSK3  ADTLRQQQQQ  LLTAFVEARG  ISVAVG....  ..........  ...TSHAPPS
rSK1  AQAICPLPPP  W...PGPSHL  TTAAQSPQSH  WLPTTASDCG  *.........
```

The fourth predicted membrane spanning domain contains 3 positively charged residues that do not occupy every third position as in voltage-dependent potassium channels (Durell et al., *Biophys. J.*, 62:238–250 (1992)), but are separated by 6 and 7 residues. There are multiple consensus targets for phosphorylation by a variety of protein kinases. Some of these sites are found in all clones. However, each clone contains potential phosphorylation sites not conserved among all members. There are no conserved N-linked glycosylation sites (NXXS/T) (SEQ ID NO:46) in predicted extracellular domains, and no consensus nucleotide or calcium binding domains (E-F hands).

Northern blots of rat brain and skeletal muscle showed that rSK3 transcripts from these tissues encoded proteins that were N-terminally extended relative to the rSK3 clone SEQ ID NO:16. The nucleic acid encoding the rSK3 N-terminal extension was cloned and sequenced, and the cDNA encoding N-terminal extended rSK3 is represented by SEQ ID NO:44. In addition, endogenous rSK3 was shown to have a nucleotide sequence that encodes a protein having a C-terminus with the last 5 amino acids of SEQ ID NO:3 replaced by the last 9 amino acids of SEQ ID NO:43. Similarly, hSK3 was shown to have an N-terminal extension, and the cDNA encoding this N-terminal extension is represented by SEQ ID NO:48.

B. To isolate intermediate conductance calcium activated $K^+$ proteins, one can use PCR under standard conditions. Suitable primers are SEQ ID NOS:34 and 35 which yield a probe of about 270 bases and SEQ ID NOS:36 and 37 which yield a probe of about 165 bases. These primers can be used to amplify plasmid DNA comprising cloned hIK1 or on reverse transcribed RNA from a tissue which expresses hIK1, such as a cDNA library from pancreas. The PCR reaction will yield DNA fragments of the specified size which contain sequences specific to hIK1 and related genes. These DNA fragments are subsequently labeled for use as hybridization probes by standard random-priming protocols. The labeled probes are then used to screen libraries at high stringency to isolate only hIK1 sequences, or at moderately low stringency (30–40% formamide, 37° C. hyb/1×SSC, 55° C. wash) to isolate putatively related sequences. Alternatively, one can amplify the intact hIK1 gene from a pancreas cDNA library using PCR primer pair SEQ ID NOS:38 and 39 or 40 and 41.

EXAMPLE 2

Example 2 describes in situ hybridization of rat brain sections using sequences distinct for each of the rat SK channel clones, and determination of transcript sizes from various peripheral tissues.

Care and handling of adult female Sprague-Dawley rats were in accordance with the highest standards of institutional guidelines. Rats were deeply anesthetized with pentobarbital and perfused transcardially with ice-cold saline, followed by ice-cold 4% paraformaldehyde in 0.1 M sodium borate (pH 9.5). The brains were removed quickly and post-fixed overnight at 4° C. in 4% paraformaldehyde in borate buffer (pH 9.5) containing 10% sucrose. Cryostat microtome sections (25 mm) were mounted onto gelatin- and poly-L-lysine-coated glass slides and incubated for 15 min in 4% paraformaldehyde in 0.1 M PBS, washed twice in 0.1 M PBS, and treated for 30 min at 37° C. in 10 mg/ml proteinase K in 100 mM Tris, 50 mM EDTA (pH 8), followed by 0.0025% acetic anhydride in 0.1 M triethanolamine at room temperature. The sections were then washed in 2×SSC, dehydrated in increasing concentrations of ethanol, and vacuum-dried at room temperature.

Templates for probe synthesis represented C-terminal and 3' untranslated sequences unique to each of the clones, and were subcloned into pKS. Using linearized template DNA, $^{35}S$-labeled antisense cRNA probe heated to 65° C. for 5 min and diluted to $10^7$ cpm/ml in hybridization buffer; 66% formamide, 260 mM NaCl, 1.3×Denhardt solution, (13 mM Tris, pH 8.0,1.3 mM EDTA, 13% dextran sulfate). Sections in hybridization mixture were covered with siliconized glass coverslips and sealed using DPX mountant. After incubating at 58° C. for 20 hr, the slides were soaked in 4×SSC to remove coverslips, then rinsed in 4×SSC (4 times, 5 min each) prior to ribonuclease A treatment (20 mg/ml for 30 min at 37° C.). The slides were then rinsed in decreasing concentrations of SSC containing 1 mM DTT to a final stringency of 0.1×SSC, 1 mM DTT for 30 min at 65° C. After dehydrating the sections in increasing concentrations of ethanol, they were vacuum-dried and exposed to DuPont Cronex-4 X-ray film for 7 days. The film was scanned by a Microtek ScanMaker 1850S at 728 pixel/cm resolution and the images analyzed using Image v1.55 software (NIH) and Photoshop (Adobe).

The results indicate that mRNAs to the rat sequences are broadly distributed throughout the CNS, in characteristic but overlapping patterns. rSK1 is expressed in the hippocampus and the dentate gyrus, the granular layer of the cerebellum, and the anterior olfactory nucleus. rSK1 mRNA was also detected in the subiculum, the olfactory tubercle, and the neocortex. rSK2 mRNA is the most widely expressed, with highest expression in the hippocampus and lower levels in the dentate gyrus, the olfactory bulb and the anterior olfactory nucleus. rSK2 mRNA was also detected in the granular layer of the cerebellum, the reticular nucleus of the thalamus, and the pontine nucleus. The pattern of in situ hybridization for rSK2 mRNA is coincident with the pattern of radiolabeled apamin binding in rat brain (Gelhart, *Neuroscience*, 52:191–205 (1993)). rSK3 mRNA was detected in the olfactory tubercle and olfactory bulb, throughout the thalamus, the lateral septum, the ventral tegmental area, and the substantia nigra pars compacta. Moderate levels were detected throughout the hypothalamus, the caudate putamen, and the nucleus accumbens.

The same distinct sequences for rSK1 and rSK2 were used to probe Northern blots prepared with mRNA isolated from total brain and several peripheral tissues. Total RNA was extracted (Chirgwin et al., *Biochem.*, 18:5294–5300 (1979)) from rat brain, adrenal gland, thymus, spleen, skeletal muscle, heart, kidney, liver, and lung of 3 week old Sprague-Dawley rats. Poly (A)$^+$ mRNA was purified by oligo d(T) cellulose chromatography (Collaborative Research), and 3 $\mu$g from each tissue was prepared as a Northern blot by electrophoresis through a 1% agarose-formaldehyde gel and transfer to Genescreen (NEN) nylon membranes. Antisense riboprobes of the same sequence as used for in situ hybridization were synthesized from linearized DNA templates using $^{32}$P-UTP (NEN). Blots were hybridized in 50% formamide, 5% SDS, 400 mM NaPO$_4$, 1 mM EDTA at 60° C. for 12 hours, followed by washes in 0.05×SSC at 65° C., and visualized using a Phosphorimager 445 SI (Molecular Dynamics) after 15 hours.

rSK1 mRNA was detected in rat brain and heart, while rSK2 mRNA was detected in brain and adrenal gland. The results show that rSK1 mRNAs of different sizes are present in brain (3.2 kb) and heart (4.4 kb). rSK2 mRNA was detected in brain and adrenal gland as two bands of 2.2 and 2.4 kb. Neither rSK1 nor rSK2 mRNA was detected from lung, liver, kidney, thymus, spleen, or skeletal muscle.

EXAMPLE 3

Example 3 describes in vitro expression of SK and IK channel proteins.

3A. Example 3A describes in vitro expression of rSK2 and hSK1 mRNAs in *Xenopus* oocytes and measurements of electrical conductance.

In vitro mRNA synthesis and oocyte injections were performed as described in Adelman et al., *Neuron*, 9:209–216 (1992). *Xenopus* care and handling were in accordance with the highest standards of institutional guidelines. Frogs underwent no more than two surgeries, separated by at least three weeks, and surgeries were performed using well established techniques. Frogs were anesthetized with an aerated solution of 3-aminobenzoic acid ethyl ester.

Oocytes were studied 2–5 days after injection with 2 ng of mRNA. Whole cell currents were measured after mRNA injection using a two electrode voltage clamp with a CA-1 amplifier interfaced to a Macintosh Quadra 650 computer. Data were simultaneously acquired through Pulse (Heka, Germany) at 500 Hz and Chart (AD Instruments, Australia) at 10 Hz. During recording, oocytes were continuously superfused with ND-96 solution containing 96 mM NaCl, 2 mM KCl, 1.8 mM CaCl$_2$, 1 mM MgCl$_2$, 5 mM HEPES (pH 7.5 with NaOH) at room temperature. To minimize Cl$^-$ currents, some oocytes were soaked and studied in Cl$^-$-free ND96 solution (96 mM Nagluconate, 2 mM Kgluconate, 2.7 mM Cagluconate$_2$, 1 mM Mggluconate$_2$, 5 mM HEPES, pH 7.5 with NaOH). Voltage protocols from a holding potential of −80 mV failed to evoke currents different from control oocytes.

Because the expression pattern of rSK2 is similar to that of mGluR1a, a metabotropic glutamate receptor (Houamed et al., *Science*, 252:1318–1321 (1991); Masu et al., *Nature*, 349:760–765 (1991)), mGluR1a mRNA was injected with or without the SK mRNAS. Addition of glutamate (1 mM) to the bath comprising the oocyte injected with mGluR1a mRNA alone evoked a transient inward current due to activation of endogenous calcium-activated chloride channels following the release of intracellular calcium (Houamed et al., *Science*, 252:1318–1321 (1991); Masu et al., *Nature*, 349:760–765 (1991)). Similar results were obtained in six other oocytes injected with mGluR1a. Voltage ramps from −120 to 60 mV applied near the peak of the inward response evoked an outwardly rectifying current that reversed at −25 mv, near the Cl$^-$ reversal potential. Addition of glutamate (1 mM) to oocytes coinjected with mGluR1a and rSK2 mRNA evoked the transient calcium-activated chloride current observed with mGluR1a injected oocytes, followed by a large transient outward current. Similar results were obtained in 14 other oocytes coinjected with mGluR1a and rSK2. Voltage ramps from −120 to 60 mV applied near the peak of the outward response evoked a large inwardly rectifying current that reversed near −95 mV, close to the K$^+$ reversal potential. This result was obtained with each of the cloned subunits and suggested that the cloned sequences encode potassium channels.

Following establishment of the 2-electrode voltage clamp, the oocyte was impaled with a third electrode containing 200 mM EGTA, pH adjusted to 7.2 with KOH. The input resistance was monitored during impalement to insure oocyte viability. At the indicated time, 50 nl of the EGTA solution was injected into the oocyte. Assuming an oocyte volume of 1 $\mu$l, the predicted final concentration of EGTA was 10 mM. Intracellular injection of EGTA abolished both current responses evoked by subsequent application of glutamate indicating that both components are calcium-activated. Similar results were obtained in 3 other oocytes coinjected with mGluR1a and rSK2. Current-voltage relation of oocytes injected with rSK2 mRNA in Cl$^-$-free external solution containing 2, 6 or 20 mM K$^+$. The current was activated by injection of CaCl$_2$ to a final concentration of ~1 mM (Adelman et al., *Neuron*, 9:209–216 (1992)). Background current was determined by application of 100 nM apamin. The apamin-insensitive background current did not vary with external K$^+$.

Two days after injection, the oocytes were soaked for >24 hours in Cl$^-$ free ND96 solution to minimize Cl$^-$ currents. In the 2-electrode recording mode, the channel was activated by injection of 5 nl of 200 mM CaCl$_2$ through a third electrode resulting in a final intracellular concentration of ~1 mM Ca$^{2+}$. This procedure resulted in a longer lasting activation of the K$^+$ current than that activated by glutamate in oocytes coinjected with mGluR1a and rSK2. In these oocytes, the reversal potential was determined relative to background current in 100 nM apamin. The mean reversal potential ±S.D. plotted versus [K$^+$]$_o$ yields a slope of 55.4 mV/decade change in [K$^+$]$_o$ and a y-intercept of −110 mV at 1 mM [K$^+$]$_o$.

Macroscopic currents were also recorded from excised patches. Currents were elicited by 2.5 second voltage ramps from −100 to 100 mV in an excised inside-out patch from an oocyte expressing rSK2. Without bath applied calcium, currents were not different from control oocytes. Oocytes were injected as described for two-electrode voltage clamp recordings.

Two to nine days after injection, inside-out macropatches were excised into a bath solution containing 116 mM Kgluconate, 4 mM KCl, 10 mM HEPES (pH 7.25, adjusted with KOH) supplemented with $CaCl_2$ and/or EGTA. To obtain nominally Ca-free solution, 1 mM EGTA was added. Alternatively, $CaCl_2$ was added to the bath solution to give free calcium concentrations of 1–10 μM. In this case, the proportion of calcium binding to gluconate was determined by a computer program (CaBuf) assuming a stability constant for $Ca^{2+}$ gluconate of $15.9M^{-1}$ (Dawson et al., *Data for Biochemical Research* (Oxford University Press, New York, (1969)). To obtain $Ca^{2+}$ concentrations below 1 μM, 5 mM EGTA was added to the bath solution and $CaCl_2$ was added as calculated using the CaBuf program and published stability constants (Fabiato et al., *J. Physiol.*, 75:463–505 (1979)). For experiments in which $Mg^{2+}$ was added to the bath solution, $MgCl_2$ was added to the total concentrations stated in the text. Under these conditions, binding of $Mg^{2+}$ to gluconate is negligible (stability constant $1.7\ M^{-1}$).

Electrodes were pulled from thin-walled, filamented borosilicate glass (World Precision Instruments) and filled with 116 mM Kgluconate, 4 mM KCl, 10 mM HEPES (pH 7.25). Electrode resistance was typically 2–5 MΩ. Membrane patches were voltage clamped using an Axopatch 200A amplifier (Axon Instruments). The data were low-pass Bessel filtered at 2 kH and acquired using Pulse software (HEKA Electronik). Analysis was performed using Pulse, Kaleidograph (Abelbeck), or IGOR (Wavemetrics) software. All experiments were performed at room temperature from a holding potential of −80 mV. 2.5 second voltage ramps from −100 to 100 mV were acquired at a sampling frequency of 500 Hz. Alternatively, current-voltage relationships were obtained from the mean current during 500 ms commands to voltages between −100 and 100 mV in 20 mV increments, sampled at 5 kHz.

Addition of 5 μM $Ca^{2+}$ to the intracellular (bath) solution evoked a substantial current. Voltage ramps in symmetrical 120 mM $K^+$ and in the absence of internal $Mg^{2+}$ revealed a current-voltage relationship with slight inward rectification. Voltage steps between −100 and 100 mV, from a holding potential of −80 mV, evoked time-independent currents. The derived I-V relationship reflects the inward rectification apparent from voltage ramps. The current was evoked by voltage steps from an inside-out macropatch excised from an oocyte expressing rSK2. With 5 μM $Ca^{2+}$ in the bath, the membrane was stepped from a holding potential of −80 mV to test potentials between −100 and 100 mV and then repolarized to −50 mV. Currents activated instantaneously and showed no inactivation during the 500 ms test pulses. Similar results were obtained for hSK1, except that the inward rectification was not as pronounced. These results identify this new family as calcium-activated potassium channels.

3B. Example 3B describes the electrophysiology of the hIK1 channel. All hIK1 channel subunits were subcloned into the oocyte expression vector pBF (unpublished, graciously provided by Dr. B. Fakler) which provides 5' and 3' untranslated regions from the *Xenopus* β-globin gene flanking a polylinker containing multiple restriction sites. In vitro mRNAs were generated using SP6 polymerase (GibcoBRL); following synthesis, mRNAs were evaluated spectrophotometrically and by ethidium bromide staining after agarose gel electrophoresis.

As described above, *Xenopus* care and handling were in accordance with the highest standards of institutional guidelines. Frogs underwent no more than two surgeries, separated by at least three weeks, and All surgeries were performed using well established techniques. Frogs were anesthetized with an aerated solution of 3-aminobenzoic acid ethyl ester. Oocytes were studied 2–14 days after injection with 0.5–5 ng of mRNA.

Inside-out macropatches were excised into an intracellular solution containing 116 mM K-gluconate, 4 mM KCl, 10 mM HEPES (pH 7.2, adjusted with KOH) supplemented with $CaCl_2$ to give free calcium concentration of 5 μM; the proportion of calcium binding to gluconate was determined by a computer program (CaBuf) assuming a stability constant for $Ca^{2+}$ gluconate of $15.9M^{-1}$ (Dawson et al., 1969). To obtain $Ca^{2+}$ concentrations below 1 μM, 1 mM EGTA was added to the bath solution and $CaCl_2$ was added as calculated using the CaBuf program and published stability constants (Fabiato and Fabiato, 1979). Electrodes were pulled from thin-walled, filamented borosilicate glass (World Precision Instruments) and filled with 116 mM K-gluconate, 4 mM KCl, 10 mM HEPES (pH 7.2). Electrode resistance was typically 2–5 MΩ. For outside-out macropatches, the solutions were reversed. Membrane patches were voltage clamped using an Axopatch 200A amplifier (Axon Instruments). The data were low-pass Bessel filtered at 1 kH and acquired using Pulse software (HEKA Electronik). Analysis was performed using Pulse, Kaleidograph (Abelbeck), or IGOR (Wavemetrics) software. Unless otherwise stated all experiments were performed at room temperature from a holding potential of 0 mV. 2.5 second voltage ramps from −100 to either 60 or 100 mV were acquired at a sampling frequency of 500 Hz. Values were expressed as mean ±SD. Statistical differences were determined using an unpaired t-test; p values <0.05 were considered significant.

For single channel recordings, oocytes were bathed in 116 mM Kgluconate, 4 mM KCl, 10 mM HEPES, 5 mM EGTA, pH 7.2 adjusted with $CaCl_2$ to yield the reported concentration of free $Ca^{2+}$. All recordings were performed in the inside-out patch configuration using thick-walled quartz electrodes (13–15 MD) containing 116 mM Kgluconate, 4 mM KCl, 10 mM HEPES, pH 7.2. Membrane patches were voltage-clamped with an Axopatch 200 amplifier (Axon Instruments). Continuous recordings were low-pass Bessel filtered at 1 kHz, acquired at 10 kHz using Pulse software (Heka Electronik) and stored directly on a Macintosh Quadra 650. Single channel recordings were analyzed with MacTac (SKALAR Instruments) using the "50% threshold" technique to estimate event amplitudes and duration, and each transition was visually inspected before being accepted. Amplitude histograms were constructed using MacTacfit (SKALAR Instruments). Only events lasting at least 1 ms were included, and amplitude histograms were fitted by single Gaussian distributions. All experiments were performed at room temperature.

The expression of the hIK1 in *Xenopus* oocytes was readily detectable. Voltage ramp commands delivered to inside-out patches excised into 5 μM $Ca^{2+}$ evoked robust, inwardly rectifying macroscopic current responses, not present in patches from uninjected oocytes (not shown) or inside-out patches bathed in $Ca^{2+}$-free media. Voltage step commands evoked large time-independent currents only when $Ca^{2+}$ was included in the (bath) internal solution.

Altering the external K⁺ concentration (substituted by Na) shifted the reversal potential in accord with the Nernst prediction for a K⁺-selective conductance (57 mV/10-fold change in K⁺). Similar to SK2 channels, currents evoked by voltage ramp commands were dependent upon the concentration of $Ca^{2+}$ applied to the internal face of the membrane.

EXAMPLE 4

Example 4 describes the calcium sensitivity of rSK2 and hSK1 channels.

Using inside-out micropatches as described above, rSK2 currents evoked by voltage ramps were shown to dependent upon the concentration of calcium in the internal (bath) solution. The slope conductance at the reversal potential was plotted as a function of calcium concentration and the data points fit with the Hill equation. From 8 patches, the average $K_d$ for calcium was 0.63±0.23 $\mu M$. The steep dependence upon calcium seen from the plot is reflected by a Hill coefficient of 4.81±1.46, suggesting that at least two calcium ions are involved in channel gating. Similar experiments performed with hSK1 yielded a $K_d$ of 0.70±0.06 $\mu M$ and a Hill coefficient of 3.90±0.45.

To compare hIK1 and SK2, normalized current was plotted as a function of $Ca^{2+}$ concentration, and the data points fitted with the Hill equation. Both channels showed the same $K_{0.5}$ (concentration for half-maximal activation, 0.32±0.03 $\mu M$ (n=7) for hIK1 and 0.31±0.05 $\mu M$ (n=4) for SK2; p=0.68), but differed in the steepness of the $Ca^{2+}$-dependence; SK2 had a Hill coefficient of 3.5±0.4 (n=4), while hIK1 had a Hill coefficient of 1.7±0.3 (n=7, p<0.001). These results demonstrate that hIK1 is also a calcium-activated potassium channel.

EXAMPLE 5

Example 5 describes the magnesium induced inward rectification for the rSK2 channel.

The inward rectification for rSK2, described above, was observed in the absence of internal cations other than potassium and calcium (5 $\mu M$). Native SK channels exhibit inward rectification induced by internal $Mg^{2+}$ ions (Lancaster et al., *J. Neurosci.*, 11:23–30 (1991)). In the hippocampus, SK channels exhibit significant inward rectification in the presence of internal $Mg^{2+}$ (Id.). Currents were elicited from an inside-out macropatch excised from an oocyte expressing rSK2 in the presence of the varying concentrations of internal $Mg^{2+}$ and 10 $\mu M$ $Ca^{2+}$. When different concentrations of $Mg^{2+}$ (0.1–3 mM) were added to the solution bathing inside-out patches, outward currents were significantly reduced.

The concentration- and voltage-dependence of $Mg^{2+}$ induced inward rectification was examined. A slight decrease of the inward current with increasing $Mg^{2+}$. was observed. Therefore, the ratio of the outward current at potentials between 20 and 100 mV to the inward current at −100 mV was plotted as a function of the different concentrations of internal $Mg^{2+}$. From multiple experiments, the data points obtained at different $Mg^{2+}$ concentrations and voltages were fit with the Hill equation, yielding an average Hill coefficient of 0.94±0.27 (n=24). Subsequently, the Hill coefficient was fixed at 1, and the mean $K_d$ was plotted as a function of the test potential. The $K_d$ decreased with increasing voltages suggesting that $Mg^{2+}$ block was voltage-dependent. $K_d$ for $Mg^{2+}$ was obtained from 5 patches as shown in panel B at 20, 40, 60, 80 and 100 mV. Values at each potential were averaged, plotted as a function of voltage and fit with the Woodhull equation, $K_d(0\ mV)$ exp($\delta$zFE/RT) where the $K_d(0\ mV)$=6 mM, $\delta$ is the fraction of the electric field sensed by the $Mg^{2+}$ ion, 0.30, z is the valence, 2, and F, E, R, and T have their usual meanings (Woodhull, *J. Gen. Physiol.*, 61:687–708 (1973)). Applying the Woodhull equation suggested that the $Mg^{2+}$ ion senses approximately 0.30 of the membrane electric field.

EXAMPLE 6

Example 6 describes single channel recordings from oocytes.

6A. Example 6A describes single channels were examined using inside-out patches excised from oocytes expressing rSK2. Addition of calcium at submicromolar concentrations induced channel activity not seen in controls. A representative patch showed that 0.2 $\mu M$ calcium applied to the bath solution induced openings to a single amplitude. Channel activity increased as the calcium concentration was raised, such that in 0.6 $\mu M$ calcium unitary openings could no longer be resolved. Upon washout of calcium, channel activity disappeared. Channel activity in the presence of 0.4 $\mu M$ calcium was recorded at several voltages. Similar to macroscopic ramp recordings, channel open probability was not obviously dependent upon voltage.

Unitary openings measured at several voltages were used to construct a single channel I-V relationship. Solutions used were the same as for macropatch recordings (Example 5). Electrodes were pulled from Corning 7052 glass (Garner) and had resistances of 9–13 M$\Omega$. Data were filtered at 1 kHz (Bessel), acquired at 10 kHz using Pulse (HEKA Electronik) and stored directly on a Macintosh Quadra 650. Single channels were analyzed using MacTac (SKALAR Instruments). The "50% threshold" technique was used to estimate event amplitudes. The threshold was adjusted for each opening and each transition was inspected visually before being accepted. Amplitude histograms were constructed using MacTacfit (SKALAR Instruments) and best fit by a single Gaussian distribution. Channel open probability was estimated as NP(o), the product of the open probability multiplied by the number of channels. NP(o) was calculated as the sum of the (dwell time×level number) divided by the total time. N was estimated as the number of simultaneously open channels at 0.4 $\mu M$ calcium. Linear regression analysis on three patches from an oocyte expressing either rSK2 or hSK1 yielded a mean single channel conductance of 9.9±0.9 pS and 9.2±0.3 pS, respectively.

6B. Example 6B describes the single channel conductance of hIK1. The methodology is described above in Example 3B. Stationary recordings from inside-out patches excised into a bathing solution containing 0.2–1.0 $\mu M$ free calcium showed short-duration openings not seen in the absence of calcium. Representative traces were recorded at −60 mV. The degree of channel activity depended upon the concentration of internal calcium. Reducing intracellular calcium reduced channel activity, and removing internal calcium abolished channel activity, which returned after reapplication of $Ca^{2+}$. Sustained channel activity was seen at membrane voltages ranging from −100 mV to +100 mV and open probability was not obviously voltage-dependent. For select patchs, the amplitudes of openings were measured, assembled into histograms, and fit by Gaussian distributions. The resulting mean amplitudes were used to construct the current-voltage relationship. The single channel current-voltage relationship shows inward rectification similar to the macroscopic current-voltage relationship. For this patch, linear regression analysis of the inward current-voltage relationship yielded a single channel conductance of 35 pS;

results from four patches gave a unit conductance of 38±4 pS. Measurements of the outward conductance were more variable, ranging from 5 to 12 pS.

EXAMPLE 7

Example 7 describes the pharmacology of the novel rat and human potassium channels.

7A. Macroscopic rSK2 currents were recorded in 5 µM $Ca^{2+}$ from inside-out macropatches with either 0 or 60 pM apamin or 0 or 2 µM d-tubocurare in the patch pipette described in Example 3. The functional characteristics of the cloned channels are reminiscent of the SK class of calcium-activated potassium channels described in neurons (Lancaster and Adams, *J. Neurophysiol.*, 55:1268–1282 (1986); Lancaster et al., *J. Neurosci.*, 11:23–30 (1991); Sah et al., *J. Neurophysiol.*, 68:1834–1841 (1992)), skeletal muscle (Blatz and Magleby, *Nature*, 323:718–720 (1986)), adrenal chromaffin cells (Park, *J. Physiol.*, 481:555–570 ((1994); Artalejo et al., *Pflugers Archiv.*, 423:97–103 (1993)), and T-lymphocytes (Grissmer et al., *J. Gen. Physiol.*, 99:63–84 (1992)). Native SK channels present a distinct pharmacology. They are not blocked by the scorpion peptide, charybdotoxin (CTX), a potent blocker of BK potassium channels (Miller et al., *Nature*, 313:316–318 (1985)). However, many but not all SK channels are blocked by the bee venom toxin, apamin, and the plant alkyloid, d-tubocurare (dTC; Zhang and McBain, *J. Physiol.*, 488:661–672 (1995), Park, *J. Physiol.*, 481:555–570(1994); Dunet al., *J. Physiol.*, 375:499–514(1986)). Application of 500 nM CTX did not block rSK2 or hSK1, but abolished the activity of hSlo BK currents. rSK2 currents were potently blocked by picomolar concentrations of apamin with a $K_d$ of 63 pM. In contrast, application of 100 nM apamin did not affect hSK-1 currents (n=8). dTC also blocked rSK2 currents with a $K_d$ of 2.4 µM, while hSK1 was approximately 30-fold less sensitive, with a $K_d$ of 76.2 µM.

7B. For the pharmacology tests of hIK1, Clotrimazole was from Sigma, ketoconazole and iberiotoxin were from RPI, apamin was from Calbiochem, charybdotoxin was the generous gift of Dr. Chris Miller. The functional characteristics of hIK1 are remeniscent of intermediate conductance calcium-activated $K^+$ channels described from red blood cells (the Gardos channel; Gardos, 1958) and other tissues. Native IK channels present a distinguishing pharmacology, being blocked by charybdotoxin (CTX) but, different from large conductance voltage- and $Ca^{2+}$-activated $K^+$ channels (BK channels), are not blocked by iberiotoxin. Also, IK channels are not sensitive to the bee venom peptide toxin apamin, a blocker of certain native and cloned SK channels. In addition, some IK channels, notably the Gardos channel, are sensitive to several imidazole derivatives such as clotrimazole, but are not sensitive to others such as ketoconazole. hIK1 currents were potently blocked by CTX, with a $K_i$ of 2.5 nM (n=4), while 50 nM IBX blocked only 15±3%. Human IK1 was sensitive to clotrimazole with a Ki of 24.8 nM, but was only 24±6% blocked by 10 µM ketoconazole. 100 nM apamin reduced hIK1 currents by only 12±5%.

All publications and patents mentioned in this specification are herein incorporated by reference into the specification to the same extent as if each individual publication or patent was specifically and individually indicated to be incorporated herein by reference.

What is claimed is:

1. An isolated polypeptide monomer of an SK1 calcium-activated potassium channel, said monomer forming a potassium channel having a unit conductance of between 2 and 60 pS when a nucleic acid encoding the monomer is expressed in a *Xenopus* oocyte, wherein said polypeptide is encoded by a nucleic acid that selectively hybridizes under stringent conditions to a sequence of SEQ ID NO:13, wherein the hybridization reaction is incubated overnight at 37° C. in a solution comprising 40% formamide, 1 M NaCl and 1% SDS, and washed at 55° C. in a solution comprising 0.5× SSC.

2. The polypeptide of claim 1, wherein said polypeptide is encoded by a nucleic acid that selectively hybridizes under stringent conditions to a sequence of SEQ ID NO:14, wherein the hybridization reaction is incubated overnight at 37° C. in a solution comprising 40% formamide, 1 M NaCl and 1% SDS, and washed at 55° C. in a solution comprising 0.5×SSC.

3. The polypeptide of claim 1, comprising an amino acid sequence selected from the group consisting of SEQ ID NO:1 and SEQ ID NO:4.

4. The polypeptide of claim 1, wherein said polypeptide is encoded by a nucleic acid comprising a nucleotide sequence selected from the group consisting of SEQ ID NO:13 and SEQ ID NO:14.

* * * * *

SEQUENCE LISTING (1) GENERAL INFORMATION:

(iii) NUMBER OF SEQUENCES: 48

(2) INFORMATION FOR SEQ ID NO: 1:

(i) SEQUENCE CHARACTERISTICS:
      (A) LENGTH: 561 amino acids
      (B) TYPE: amino acid
      (C) STRANDEDNESS: <Unknown>
      (D) TOPOLOGY: linear (ii) MOLECULE TYPE: protein (ix) FEATURE:
      (A) NAME/KEY: Protein
      (B) LOCATION: 1..561
      (D) OTHER INFORMATION: /note= "human small conductance,
         calcium-activated potassium channel
         protein 1 (hSK1)"

(xi) SEQUENCE DESCRIPTION: SEQ ID NO: 1:

Met Pro Gly Pro Arg Ala Ala Cys Ser Glu Pro Asn Pro Cys Thr Gln
1               5                   10                  15

Val Val Met Asn Ser His Ser Tyr Asn Gly Ser Val Gly Arg Pro Leu
            20                  25                  30

Gly Ser Gly Pro Gly Ala Leu Gly Arg Asp Pro Pro Asp Pro Glu Ala
        35                  40                  45

Gly His Pro Pro Gln Pro Pro His Ser Pro Gly Leu Gln Val Val Val

```
            50                  55                  60
Ala Lys Ser Glu Pro Ala Arg Pro Ser Pro Gly Ser Pro Arg Gly Gln
 65                  70                  75                  80

Pro Gln Asp Gln Asp Asp Glu Asp Glu Glu Asp Glu Ala Gly
                 85                  90                  95

Arg Gln Arg Ala Ser Gly Lys Pro Ser Asn Val Gly His Arg Leu Gly
                100                 105                 110

His Arg Arg Ala Leu Phe Glu Lys Arg Lys Arg Leu Ser Asp Tyr Ala
                115                 120                 125

Leu Ile Phe Gly Met Phe Gly Ile Val Val Met Val Thr Glu Thr Glu
130                 135                 140

Leu Ser Trp Gly Val Tyr Thr Lys Glu Ser Leu Tyr Ser Phe Ala Leu
145                 150                 155                 160

Lys Cys Leu Ile Ser Leu Ser Thr Ala Ile Leu Leu Gly Leu Val Val
                165                 170                 175

Leu Tyr His Ala Arg Glu Ile Gln Leu Phe Met Val Asp Asn Gly Ala
                180                 185                 190

Asp Asp Trp Arg Ile Ala Met Thr Cys Glu Arg Val Phe Leu Ile Ser
                195                 200                 205

Leu Glu Leu Ala Val Cys Ala Ile His Pro Val Pro Gly His Tyr Arg
210                 215                 220

Phe Thr Trp Thr Ala Arg Leu Ala Phe Thr Tyr Ala Pro Ser Val Ala
225                 230                 235                 240

Glu Ala Asp Val Asp Val Leu Leu Ser Ile Pro Met Phe Leu Arg Leu
                245                 250                 255

Tyr Leu Leu Gly Arg Val Met Leu Leu His Ser Lys Ile Phe Thr Asp
                260                 265                 270

Ala Ser Ser Arg Ser Ile Gly Ala Leu Asn Lys Ile Thr Phe Asn Thr
                275                 280                 285

Arg Phe Val Met Lys Thr Leu Met Thr Ile Cys Pro Gly Thr Val Leu
                290                 295                 300

Leu Val Phe Ser Ile Ser Ser Trp Ile Ile Ala Ala Trp Thr Val Arg
305                 310                 315                 320

Val Cys Glu Arg Tyr His Asp Lys Gln Glu Val Thr Ser Asn Phe Leu
                325                 330                 335

Gly Ala Met Trp Leu Ile Ser Ile Thr Phe Leu Ser Ile Gly Tyr Gly
                340                 345                 350

Asp Met Val Pro His Thr Tyr Cys Gly Lys Gly Val Cys Leu Leu Thr
                355                 360                 365

Gly Ile Met Gly Ala Gly Cys Thr Ala Leu Val Val Ala Val Val Ala
                370                 375                 380

Arg Lys Leu Glu Leu Thr Lys Ala Glu Lys His Val His Asn Phe Met
385                 390                 395                 400

Met Asp Thr Gln Leu Thr Lys Arg Val Lys Asn Ala Ala Ala Asn Val
                405                 410                 415

Leu Arg Glu Thr Trp Leu Ile Tyr Lys His Thr Arg Leu Val Lys Lys
                420                 425                 430

Pro Asp Gln Ala Arg Val Arg Lys His Gln Arg Lys Phe Leu Gln Ala
                435                 440                 445

Ile His Gln Ala Gln Lys Leu Arg Ser Val Lys Ile Glu Gln Gly Lys
                450                 455                 460

Leu Asn Asp Gln Ala Asn Thr Leu Thr Asp Leu Ala Lys Thr Gln Thr
465                 470                 475                 480
```

```
Val Met Tyr Asp Leu Val Ser Glu Leu His Ala Gln His Glu Leu
            485                 490                 495

Glu Ala Arg Leu Ala Thr Leu Glu Ser Arg Leu Asp Ala Leu Gly Ala
            500                 505                 510

Ser Leu Gln Ala Leu Pro Gly Leu Ile Ala Gln Ala Ile Arg Pro Pro
            515                 520                 525

Pro Pro Pro Leu Pro Pro Arg Pro Gly Pro Gly Pro Gln Asp Gln Ala
            530                 535                 540

Ala Arg Ser Ser Pro Cys Arg Trp Thr Pro Val Ala Pro Ser Asp Cys
545                 550                 555                 560

Gly (2) INFORMATION FOR SEQ ID NO: 2:

(i) SEQUENCE CHARACTERISTICS:
        (A) LENGTH: 580 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Protein
        (B) LOCATION: 1..580
        (D) OTHER INFORMATION: /note= "rat small conductance,
            calcium-activated potassium channel
            protein 2 (rSK2)"

(ix) FEATURE:
        (A) NAME/KEY: Region
        (B) LOCATION: 135..462
        (D) OTHER INFORMATION: /note= "core region of rSK2"

(xi) SEQUENCE DESCRIPTION: SEQ ID NO: 2:

Met Ser Ser Cys Arg Tyr Asn Gly Gly Val Met Arg Pro Leu Ser As
1               5                   10                  15

Leu Ser Ser Arg Arg Asn Leu His Glu Met Asp Ser Glu Ala Gl
            20                  25                  30

Pro Leu Gln Pro Pro Ala Ser Val Val Gly Gly Gly Gly Gly Ala Se
            35                  40                  45

Ser Pro Ser Ala Ala Ala Ala Ser Ser Ser Ala Pro Glu Ile Va
        50                  55                  60

Val Ser Lys Pro Glu His Asn Asn Ser Asn Asn Leu Ala Leu Tyr Gl
65                  70                  75                  80

Thr Gly Gly Gly Gly Ser Thr Gly Gly Gly Gly Gly Gly Gly Gly Gl
            85                  90                  95

Gly Gly Gly Ser Gly His Gly Ser Ser Ser Gly Thr Lys Ser Ser Ly
            100                 105                 110

Lys Lys Asn Gln Asn Ile Gly Tyr Lys Leu Gly His Arg Arg Ala Le
            115                 120                 125

Phe Glu Lys Arg Lys Arg Leu Ser Asp Tyr Ala Leu Ile Phe Gly Me
            130                 135                 140

Phe Gly Ile Val Val Met Val Ile Glu Thr Glu Leu Ser Trp Gly Al
145                 150                 155                 160

Tyr Asp Lys Ala Ser Leu Tyr Ser Leu Ala Leu Lys Cys Leu Ile Se
                165                 170                 175

Leu Ser Thr Ile Ile Leu Leu Gly Leu Ile Ile Val Tyr His Ala Ar
            180                 185                 190
```

-continued

```
Glu Ile Gln Leu Phe Met Val Asp Asn Gly Ala Asp Asp Trp Arg Il
            195                 200                 205
Ala Met Thr Tyr Glu Arg Ile Phe Phe Ile Cys Leu Glu Ile Leu Va
        210                 215                 220
Cys Ala Ile His Pro Ile Pro Gly Asn Tyr Thr Phe Thr Trp Thr Al
225                 230                 235                 240
Arg Leu Ala Phe Ser Tyr Ala Pro Ser Thr Thr Thr Ala Asp Val As
                245                 250                 255
Ile Ile Leu Ser Ile Pro Met Phe Leu Arg Leu Tyr Leu Ile Ala Ar
                260                 265                 270
Val Met Leu Leu His Ser Lys Leu Phe Thr Asp Ala Ser Ser Arg Se
                275                 280                 285
Ile Gly Ala Leu Asn Lys Ile Asn Phe Asn Thr Arg Phe Val Met Ly
            290                 295                 300
Thr Leu Met Thr Ile Cys Pro Gly Thr Val Leu Leu Val Phe Ser Il
305                 310                 315                 320
Ser Leu Trp Ile Ile Ala Ala Trp Thr Val Arg Ala Cys Glu Arg Ty
                325                 330                 335
His Asp Gln Gln Asp Val Thr Ser Asn Phe Leu Gly Ala Met Trp Le
            340                 345                 350
Ile Ser Ile Thr Phe Leu Ser Ile Gly Tyr Gly Asp Met Val Pro As
            355                 360                 365
Thr Tyr Cys Gly Lys Gly Val Cys Leu Leu Thr Gly Ile Met Gly Al
        370                 375                 380
Gly Cys Thr Ala Leu Val Val Ala Val Val Ala Arg Lys Leu Glu Le
385                 390                 395                 400
Thr Lys Ala Glu Lys His Val His Asn Phe Met Met Asp Thr Gln Le
                405                 410                 415
Thr Lys Arg Val Lys Asn Ala Ala Ala Asn Val Leu Arg Glu Thr Tr
                420                 425                 430
Leu Ile Tyr Lys Asn Thr Lys Leu Val Lys Lys Ile Asp His Ala Ly
            435                 440                 445
Val Arg Lys His Gln Arg Lys Phe Leu Gln Ala Ile His Gln Leu Ar
        450                 455                 460
Ser Val Lys Met Glu Gln Arg Lys Leu Asn Asp Gln Ala Asn Thr Le
465                 470                 475                 480
Val Asp Leu Ala Lys Thr Gln Asn Ile Met Tyr Asp Met Ile Ser As
                485                 490                 495
Leu Asn Glu Arg Ser Glu Asp Phe Glu Lys Arg Ile Val Thr Leu Gl
            500                 505                 510
Thr Lys Leu Glu Thr Leu Ile Gly Ser Ile His Ala Leu Pro Gly Le
            515                 520                 525
Ile Ser Gln Thr Ile Arg Gln Gln Arg Asp Phe Ile Glu Thr Gl
            530                 535                 540
Met Glu Asn Tyr Asp Lys His Val Thr Tyr Asn Ala Glu Arg Ser Ar
545                 550                 555                 560
Ser Ser Ser Arg Arg Arg Ser Ser Ser Thr Ala Pro Pro Thr Se
                565                 570                 575
Ser Glu Ser Ser
            580
```

(2) INFORMATION FOR SEQ ID NO: 3:

(i) SEQUENCE CHARACTERISTICS:

```
    (A) LENGTH: 553 amino acids
    (B) TYPE: amino acid
    (C) STRANDEDNESS: <Unknown>
    (D) TOPOLOGY: linear (ii) MOLECULE TYPE: protein (ix) FEATURE:
    (A) NAME/KEY: Protein
    (B) LOCATION: 1..553
    (D) OTHER INFORMATION: /note= "N-terminally truncated form
        of rat small conductance,
        calcium-activated potassium channel
        protein 3 (rSK3)"

(ix) FEATURE:
    (A) NAME/KEY: Region
    (B) LOCATION: 109..436
    (D) OTHER INFORMATION: /note= "core region of rSK3"

(xi) SEQUENCE DESCRIPTION: SEQ ID NO: 3:
```

```
Met Ser Ser Cys Lys Tyr Ser Gly Gly Val Met Lys Pro Leu Ser Ar
1               5                   10                  15

Leu Ser Ala Ser Arg Arg Asn Leu Ile Glu Ala Glu Pro Glu Gly Gl
            20                  25                  30

Pro Leu Gln Leu Phe Ser Pro Ser Asn Pro Pro Glu Ile Ile Ile Se
        35                  40                  45

Ser Arg Glu Asp Asn His Ala His Gln Thr Leu Leu His His Pro As
    50                  55                  60

Ala Thr His Asn His Gln His Ala Gly Thr Thr Ala Gly Ser Thr Th
65                  70                  75                  80

Phe Pro Lys Ala Asn Lys Arg Lys Asn Gln Asn Ile Gly Tyr Lys Le
                85                  90                  95

Gly His Arg Arg Ala Leu Phe Glu Lys Arg Lys Arg Leu Ser Asp Ty
            100                 105                 110

Ala Leu Ile Phe Gly Met Phe Gly Ile Val Val Met Val Ile Glu Th
            115                 120                 125

Glu Leu Ser Trp Gly Leu Tyr Ser Lys Asp Ser Met Phe Ser Leu Al
130                 135                 140

Leu Lys Cys Leu Ile Ser Leu Ser Thr Ile Ile Leu Leu Gly Leu Il
145                 150                 155                 160

Ile Ala Tyr His Thr Arg Glu Val Gln Leu Phe Val Ile Asp Asn Gl
                165                 170                 175

Ala Asp Asp Trp Arg Ile Ala Met Thr Tyr Glu Arg Ile Leu Tyr Il
            180                 185                 190

Ser Leu Glu Met Leu Val Cys Ala Ile His Pro Ile Pro Gly Glu Ty
            195                 200                 205

Lys Phe Phe Trp Thr Ala Arg Leu Ala Phe Ser Tyr Thr Pro Ser Ar
210                 215                 220

Ala Glu Ala Asp Val Asp Ile Ile Leu Ser Ile Pro Met Phe Leu Ar
225                 230                 235                 240

Leu Tyr Leu Ile Ala Arg Val Met Leu Leu His Ser Lys Leu Phe Th
                245                 250                 255

Asp Ala Ser Ser Arg Ser Ile Gly Ala Leu Asn Lys Ile Asn Phe As
            260                 265                 270

Thr Arg Phe Val Met Lys Thr Leu Met Thr Ile Cys Pro Gly Thr Va
            275                 280                 285

Leu Leu Met Phe Ser Ile Ser Leu Trp Ile Ile Ala Ala Trp Thr Va
290                 295                 300
```

```
Arg Val Cys Glu Arg Tyr His Asp Gln Gln Asp Val Thr Ser Asn Ph
305                 310                 315                 320

Leu Gly Ala Met Trp Leu Ile Ser Ile Thr Phe Leu Ser Ile Gly Ty
                325                 330                 335

Gly Asp Met Val Pro His Thr Tyr Cys Gly Lys Gly Val Cys Leu Le
                340                 345                 350

Thr Gly Ile Met Gly Ala Gly Cys Thr Ala Leu Val Val Ala Val Va
            355                 360                 365

Ala Arg Lys Leu Glu Leu Thr Lys Ala Glu Lys His Val His Asn Ph
        370                 375                 380

Met Met Asp Thr Gln Leu Thr Lys Arg Ile Lys Asn Ala Ala Ala As
385                 390                 395                 400

Val Leu Arg Glu Thr Trp Leu Ile Tyr Lys His Thr Lys Leu Leu Ly
                405                 410                 415

Lys Ile Asp His Ala Lys Val Arg Lys His Gln Arg Lys Phe Leu Gl
                420                 425                 430

Ala Ile His Gln Leu Arg Gly Val Lys Met Glu Gln Arg Lys Leu Se
            435                 440                 445

Asp Gln Ala Asn Thr Leu Val Asp Leu Ser Lys Met Gln Asn Val Me
        450                 455                 460

Tyr Asp Leu Ile Thr Glu Leu Asn Asp Arg Ser Glu Asp Leu Glu Ly
465                 470                 475                 480

Gln Ile Gly Ser Leu Glu Ser Lys Leu Glu His Leu Thr Ala Ser Ph
                485                 490                 495

Asn Ser Leu Pro Leu Leu Ile Ala Asp Thr Leu Arg Gln Gln Gln Gl
                500                 505                 510

Gln Leu Leu Thr Ala Phe Val Glu Ala Arg Gly Ile Ser Val Ala Va
            515                 520                 525

Gly Thr Ser His Ala Pro Pro Ser Asp Ser Pro Ile Gly Ile Ser Se
            530                 535                 540

Thr Ser Phe Pro Glu Phe Leu Ile Phe
545                 550

(2) INFORMATION FOR SEQ ID NO: 4:

(i) SEQUENCE CHARACTERISTICS:
        (A) LENGTH: 458 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Protein
        (B) LOCATION: 1..458
        (D) OTHER INFORMATION: /note= "rat small conductance,
            calcium-activated potassium channel
            protein 1 (rSK1)"

(xi) SEQUENCE DESCRIPTION: SEQ ID NO: 4:

Ser Gly Lys Pro Pro Thr Val Ser His Arg Leu Gly His Arg Arg Al
1               5                   10                  15

Leu Phe Glu Lys Arg Lys Arg Leu Ser Asp Tyr Ala Leu Ile Phe Gl
                20                  25                  30

Met Phe Gly Ile Val Val Met Val Thr Glu Thr Glu Leu Ser Trp Gl
            35                  40                  45

Val Tyr Thr Lys Glu Ser Leu Cys Ser Phe Ala Leu Lys Cys Leu Il
        50                  55                  60
```

```
Ser Leu Ser Thr Val Ile Leu Gly Leu Val Ile Leu Tyr His Al
 65                  70                  75                  80

Arg Glu Ile Gln Leu Phe Leu Val Asp Asn Gly Ala Asp Asp Trp Ar
                 85                  90                  95

Ile Ala Met Thr Trp Glu Arg Val Ser Leu Ile Ser Leu Glu Leu Al
                100                 105                 110

Val Cys Ala Ile His Pro Val Pro Gly His Tyr Arg Phe Thr Trp Th
                115                 120                 125

Ala Arg Leu Ala Phe Ser Leu Val Pro Ser Ala Ala Glu Ala Asp Va
                130                 135                 140

Asp Val Leu Leu Ser Ile Pro Met Phe Leu Arg Leu Tyr Leu Leu Al
145                 150                 155                 160

Arg Val Met Leu Leu His Ser Arg Ile Phe Thr Asp Ala Ser Ser Ar
                165                 170                 175

Ser Ile Gly Ala Leu Asn Arg Val Thr Phe Asn Thr Arg Phe Val Th
                180                 185                 190

Lys Thr Leu Met Thr Ile Cys Pro Gly Thr Val Leu Leu Val Phe Se
                195                 200                 205

Ile Ser Ser Trp Ile Val Ala Ala Trp Thr Val Arg Val Cys Glu Ar
210                 215                 220

Tyr His Asp Lys Gln Glu Val Thr Ser Asn Phe Leu Gly Ala Met Tr
225                 230                 235                 240

Leu Ile Ser Ile Thr Phe Leu Ser Ile Gly Tyr Gly Asp Met Val Pr
                245                 250                 255

His Thr Tyr Cys Gly Lys Gly Val Cys Leu Leu Thr Gly Ile Met Gl
                260                 265                 270

Ala Gly Cys Thr Ala Leu Val Val Ala Val Val Ala Arg Lys Leu Gl
                275                 280                 285

Leu Thr Lys Ala Glu Lys His Val His Asn Phe Met Met Asp Thr Gl
                290                 295                 300

Leu Thr Lys Arg Val Lys Asn Ala Ala Ala Asn Val Leu Arg Glu Th
305                 310                 315                 320

Trp Leu Ile Tyr Lys His Thr Arg Leu Val Lys Pro Asp Gln Se
                325                 330                 335

Arg Val Arg Lys His Gln Arg Lys Phe Leu Gln Ala Ile His Gln Al
                340                 345                 350

Gln Lys Leu Arg Thr Val Lys Ile Glu Gln Gly Lys Val Asn Asp Gl
                355                 360                 365

Ala Asn Thr Leu Ala Asp Leu Ala Lys Ala Gln Ser Ile Ala Tyr Gl
                370                 375                 380

Val Val Ser Glu Leu Gln Ala Gln Gln Glu Glu Leu Glu Ala Arg Le
385                 390                 395                 400

Ala Ala Leu Glu Ser Arg Leu Asp Val Leu Gly Ala Ser Leu Gln Al
                405                 410                 415

Leu Pro Ser Leu Ile Ala Gln Ala Ile Cys Pro Leu Pro Pro Tr
                420                 425                 430

Pro Gly Pro Ser His Leu Thr Thr Ala Ala Gln Ser Pro Gln Ser Hi
                435                 440                 445

Trp Leu Pro Thr Thr Ala Ser Asp Cys Gly
450                 455
```

(2) INFORMATION FOR SEQ ID NO: 5:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 5:

ATGCCGGGTC CCCGGGCGGC CTGC                                              24

(2) INFORMATION FOR SEQ ID NO: 6:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 6:

TCACCCGCAG TCCGAGGGGG CCAC                                              24

(2) INFORMATION FOR SEQ ID NO: 7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 7:

ATGAGCAGCT GCAGGTACAA CGGG                                              24

(2) INFORMATION FOR SEQ ID NO: 8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 8:

CTAGCTACTC TCAGATGAAG TTGG                                              24

(2) INFORMATION FOR SEQ ID NO: 9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 9:

ATGAGCTCCT GCAAATACAG CGGT                                              24

(2) INFORMATION FOR SEQ ID NO: 10:

(i) SEQUENCE CHARACTERISTICS:
            (A) LENGTH: 20 base pairs
            (B) TYPE: nucleic acid
            (C) STRANDEDNESS: single -continued (D) TOPOLOGY: linear (ii) MOLECULE TYPE: DNA (xi) SEQUENCE DESCRIPTION: SEQ ID NO: 10:

TTAGCAACTG CTTGAACTTG                20

(2) INFORMATION FOR SEQ ID NO: 11:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 11:

TCAGGGAAGC CCCCGACCGT CAGT              24

(2) INFORMATION FOR SEQ ID NO: 12:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 12:

TCACCCACAG TCTGATGCCG TGGT              24

(2) INFORMATION FOR SEQ ID NO: 13:

(i) SEQUENCE CHARACTERISTICS:
    (A) LENGTH: 1683 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: -
    (B) LOCATION: 1..1683
    (D) OTHER INFORMATION: /note= "human small conductance,
      calcium-activated potassium channel
      protein 1 (hSK1) cDNA"

(xi) SEQUENCE DESCRIPTION: SEQ ID NO: 13:

ATGCCGGGTC CCCGGGCGGC CTGCAGCGAG CCCAACCCCT GCACCCAGGT AGTCATGAAC  60

AGCCACAGCT ACAATGGCAG CGTGGGGCGG CCGCTGGGCA GCGGGCCGGG CGCCCTGGG  120

CGAGACCCTC CGGACCCTGA GGCCGGCCAC CCCCCACAAC CCCCGCACAG CCCGGGCCT  180

CAGGTGGTAG TGGCCAAGAG TGAGCCAGCC CGGCCCTCAC CCGGCAGCCC CCGGGGGCA  240

CCCCAGGACC AGGACGATGA CGAGGATGAT GAGGAAGATG AGGCCGGCAG GCAGAGAGC  300

TCGGGGAAAC CCTCAAATGT GGGCCACCGC CTGGGCCACC GGCGGGCGCT CTTCGAGAA  360

CGGAAGCGCC TCAGCGACTA TGCCCTCATT TTCGGCATGT TTGGCATCGT CGTCATGGT  420

ACGGAGACCG AGCTGTCCTG GGGGGTGTAC ACCAAGGAGT CTCTGTACTC ATTCGCACT  480

AAATGCCTCA TGAGCCTCTC CACGGCCATC CTGCTGGGTC TCGTTGTCCT CTACCATGC  540

CGGGAGATCC AGCTGTTCAT GGTGGACAAC GGGGCTGATG ACTGGCGCAT CGCCATGAC  600

TGCGAGCGCG TGTTCCTCAT CTCGCTAGAG CTGGCAGTGT GCGCCATTCA CCCGGTGCC  660

-continued

```
GGCCACTACC GCTTCACGTG GACGGCGCGG CTGGCCTTCA CGTACGCGCC CTCGGTGGC      720

GAGGCCGACG TGGACGTGCT GCTGTCCATC CCCATGTTCC TGCGCCTCTA CCTGCTGGG      780

CGGGTGATGC TACTGCACAG CAAAATCTTC ACGGACGCCT CGAGCCGCAG CATCGGGGC      840

CTCAACAAGA TCACCTTCAA CACGCGCTTC GTCATGAAGA CACTCATGAC CATCTGCCC      900

GGCACCGTGC TGCTGGTCTT CAGCATCTCC TCCTGGATCA TCGCAGCCTG GACCGTGCG      960

GTCTGCGAGA GGTACCACGA CAAGCAGGAA GTGACCAGCA ACTTCCTGGG GGCCATGT     1020

CTGATTTCCA TCACCTTCCT CTCCATTGGC TACGGCGACA TGGTGCCCCA CACCTACT     1080

GGGAAGGGTG TGTGCCTGCT CACTGGCATC ATGGGAGCTG GCTGTACCGC GCTCGTGG     1140

GCTGTGGTGG CTCGGAAGCT GGAGCTCACC AAGGCTGAGA AGCACGTGCA CAACTTCA     1200

ATGGACACTC AGCTCACCAA GCGGGTAAAA AACGCCGCTG CTAACGTTCT CAGGGAGA     1260

TGGCTCATCT ACAAACATAC CAGGCTGGTG AAGAAGCCAG ACCAAGCCCG GGTTCGGA     1320

CACCAGCGTA AGTTCCTCCA AGCCATCCAT CAGGCTCAGA AGCTCCGGAG TGTGAAGA     1380

GAGCAAGGGA AGCTGAACGA CCAGGCTAAC ACGCTTACCG ACCTAGCCAA GACCCAGA     1440

GTCATGTACG ACCTTGTATC GGAGCTGCAC GCTCAGCACG AGGAGCTGGA GGCCCGCC     1500

GCCACCCTGG AAAGCCGCTT GGATGCGCTG GGTGCCTCTC TACAGGCCCT GCCTGGCC     1560

ATCGCCCAAG CCATACGCCC ACCCCCGCCT CCCCTGCCTC CCAGGCCCGG CCCCGGCC     1620

CAAGACCAGG CAGCCCGGAG CTCCCCCTGC CGGTGGACGC CCGTGGCCCC CTCGGACT     1680

GGG                                                                1683
```

(2) INFORMATION FOR SEQ ID NO: 14:

(i) SEQUENCE CHARACTERISTICS:
        (A) LENGTH: 1374 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1374
        (D) OTHER INFORMATION: /note= "rat small conductance,
            calcium-activated potassium channel
            protein 1 (rSK1) cDNA"

(xi) SEQUENCE DESCRIPTION: SEQ ID NO: 14:

```
TCAGGGAAGC CCCCGACCGT CAGTCACCGC CTGGGCCACC GTAGGGCCCT CTTCGAGAAG       60

CGTAAACGAC TCAGTGACTA TGCACTCATC TTTGGCATGT TCGGGATTGT CGTCATGGT      120

ACAGAAACAG AGCTGTCCTG GGTGTGTAC ACCAAGGAGT CTCTGTGCTC ATTCGCCCT       180

AAATGCCTAA TCAGCCTCTC CACTGTCATC CTGCTTGGCC TTGTCATCCT CTACCACGC      240

CGAGAGATCC AGCTGTTCCT GGTGGACAAT GGTGCCGATG ACTGGCGCAT TGCCATGAC      300

TGGGAGCGAG TGTCCCTGAT CTCGCTGGAG TTGGCTGTGT GTGCCATCCA CCCAGTGCC      360

GGCCACTACC GCTTCACATG GACGGCGCGG CTGGCCTTCT CCCTGGTGCC GTCAGCAGC      420

GAGGCGGATG TGGATGTGCT TCTGTCCATC CCCATGTTTC TGCGCCTCTA TCTGCTGGC      480

CGGGTCATGC TCCTGCACAG CCGCATCTTC ACGGACGCAT CCAGTCGCAG CATCGGAGC      540

CTGAACCGTG TCACCTTCAA CACACGCTTT GTCACCAAGA CACTCATGAC CATCTGCCC      600

GGCACCGTGC TGTTGGTCTT CAGCATCTCC TCCTGGATCG TCGCTGCATG GACAGTGCG      660
```

-continued

```
GTGTGTGAGA GGTACCATGA TAAACAGGAA GTGACCAGCA ACTTCCTGGG GGCCATGTG    720

CTCATCTCCA TTACCTTCCT GTCCATCGGC TACGGGACA TGGTGCCGCA CACCTACTG    780

GGGAAGGGCG TGTGTCTGCT CACCGGCATC ATGGGAGCAG GCTGCACTGC ACTCGTGGT    840

GCCGTCGTGG CCCGCAAGTT GGAACTCACC AAGGCTGAGA ACACGTGCA CAACTTCAT    900

ATGGACACAC AGCTCACCAA GCGGGTTAAA AACGCCGCTG CAAACGTTCT CAGGGAGAC    960

TGGCTCATCT ACAAACACAC CAGGCTAGTG AAGAAGCCAG ACCAAAGCCG GGTTCGGA   1020

CACCAGCGTA AGTTCCTTCA GGCCATCCAT CAGGCGCAGA AGCTCCGGAC TGTGAAGA   1080

GAACAAGGGA AGGTGAATGA TCAGGCCAAC ACGCTGGCTG ACCTGGCCAA GGCACAGA   1140

ATCGCATATG AGGTGGTGTC GGAGCTGCAG GCCCAGCAGG AGGAGTTGGA GGCCCGTC   1200

GCTGCCCTGG AGAGCCGCCT GGATGTCCTA GGCGCCTCCC TGCAGGCCCT ACCAAGTC   1260

ATAGCCCAAG CCATATGCCC TCTACCACCA CCCTGGCCCG GGCCCAGTCA CCTGACCA   1320

GCCGCCCAGA GCCCACAAAG CCACTGGCTG CCCACCACGG CATCAGACTG TGGG       1374

(2) INFORMATION FOR SEQ ID NO: 15:

(i) SEQUENCE CHARACTERISTICS:
        (A) LENGTH: 1740 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1740
        (D) OTHER INFORMATION: /note= "rat small conductance,
            calcium-activated potassium channel
            protein 2 (rSK2) cDNA"

(xi) SEQUENCE DESCRIPTION: SEQ ID NO: 15:

ATGAGCAGCT GCAGGTACAA CGGGGGCGTC ATGCGTCCGC TCAGCAACTT GAGCTCGTCC     60

CGCCGGAACC TGCACGAGAT GGACTCAGAG GCTCAGCCCC TGCAGCCCCC AGCGTCGGT    120

GTAGGAGGAG GTGGTGGTGC GTCCTCCCCG TCTGCTGCCG CCGCCGCCTC ATCCTCAGC    180

CCAGAGATCG TGGTGTCTAA GCCGGAGCAC AACAATTCTA ACAACCTGGC GCTCTACGG    240

ACTGGCGGCG GAGGCAGCAC CGGAGGCGGC GGCGGCGGCG GCGGCGGCGG CGGCGGCAG    300

GGGCATGGCA GCAGCAGCGG CACTAAGTCC AGCAAAAAGA AGAACCAGAA CATCGGCTA    360

AAGCTGGGCC ATCGGCGTGC CCTGTTTGAG AAGCGCAAGC GGCTCAGCGA CTATGCGCT    420

ATCTTCGGCA TGTTCGGCAT CGTGGTCATG GTCATCGAGA CCGAGCTGTC GTGGGGCGC    480

TACGACAAGG CGTCGCTGTA TTCTTTAGCT CTGAAATGCC TTATCAGTCT CTCCACGAT    540

ATCCTGCTTG GTCTGATCAT CGTATACCAC GCCAGGGAAA TACAGTTATT CATGGTGGA    600

AATGGAGCAG ATGACTGGAG AATAGCCATG ACTTATGAAC GTATTTTCTT CATCTGCTT    660

GAAATACTGG TGTGTGCTAT TCATCCCATC CCTGGGAATT ATACGTTCAC ATGGACAGC    720

CGGCTTGCCT TCTCCTATGC CCCTTCCACA ACCACTGCAG ACGTGGATAT TATTTTATC    780

ATACCAATGT TCTTAAGACT CTATCTGATT GCCAGAGTCA TGCTATTACA TAGCAAACT    840

TTCACCGATG CCTCCTCTAG AAGCATTGGG GCACTTAATA AGATAAACTT CAATACGCG    900

TTTGTTATGA AGACTTTAAT GACTATCTGC CCAGGAACTG TGCTCTTGGT TTTTAGTAT    960

TCGTTATGGA TAATTGCCGC ATGGACTGTC CGAGCTTGTG AAAGGTACCA TGATCAAC   1020

GATGTCACTA GCAACTTCCT TGGAGCAATG TGGTTGATAT CAATAACTTT TCTCTCCA   1080
```

-continued

```
GGTTATGGTG ACATGGTACC TAACACATAC TGTGGGAAAG GAGTCTGCTT GCTTACCG      1140

ATAATGGGTG CAGGTTGCAC AGCCTTGGTG GTAGCCGTAG TGGCAAGGAA GCTAGAAC      1200

ACCAAAGCAG AAAAGCATGT GCACAATTTC ATGATGGATA CTCAGCTGAC CAAAAGAG      1260

AAAAACGCAG CCGCCAATGT ACTCAGGGAA ACGTGGTTAA TCTACAAAAA CACAAAGC      1320

GTGAAAAAGA TCGACCATGC AAAAGTAAGG AAGCATCAAC GGAAATTCTT ACAAGCTA      1380

CATCAATTAA GAAGTGTGAA GATGGAACAG AGGAAACTGA ATGACCAAGC GAATACGC      1440

GTGGATCTGG CAAAGACCCA AGATATCATG TATGATATGA TTTCCGACTT AAATGTAA      1500

AGTGAAGACT TTGAGAAAAG GATCGTCACC CTGGAAACAA AATTAGAAAC TTTGATTG      1560

AGCATTCATG CCCTCCCTGG GCTTATCAGC CAGACCATCA GACAGCAGCA AAGGGACT      1620

ATAGAGACAC AGATGGAGAA CTATGACAAG CATGTCACCT ACAATGCTGA GCGTTCCC      1680

TCCTCGTCCA GGAGGCGGCG GTCCTCCTCC ACAGCGCCAC CAACTTCATC TGAGAGTA      1740
```

(2) INFORMATION FOR SEQ ID NO: 16:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1659
        (D) OTHER INFORMATION: /note= "N-terminally truncated cDNA
            for rat small conductance,
            calcium-activated potassium channel
            protein 3 (rSK3)"

(xi) SEQUENCE DESCRIPTION: SEQ ID NO: 16:

```
ATGAGCTCCT GCAAATACAG CGGTGGGGTC ATGAAGCCCC TCAGCCGCCT CAGCGCCTCT      60

CGGAGAAACC TTATCGAGGC CGAGCCTGAG GGCCAACCCC TCCAGCTCTT CAGTCCCAG      120

AACCCCCCAG AGATTATCAT CTCCTCCAGG GAGGATAACC ATGCCCACCA GACTCTGCT      180

CATCACCCCA ACGCTACCCA CAACCACCAG CATGCCGGCA CCACTGCTGG CAGCACCAC      240

TTCCCCAAAG CCAACAAGCG GAAAAACCAA ACATTGGCT ATAAGCTGGG GCACAGGAG      300

GCCCTGTTTG AAAAGAGAAA GCGACTGAGT GACTATGCTC TGATTTTTGG GATGTTTGG      360

ATTGTTGTTA TGGTGATAGA GACCGAACTG TCTTGGGGTT TGTACTCAAA GGATTCCAT      420

TTTTCGTTGG CCCTGAAATG CCTTATCAGT TTATCCACCA TCATCCTGCT TGGTTTGAT      480

ATCGCCTACC ACACAAGGGA AGTACAGCTC TTTGTGATCG ACAATGGTGC AGATGACTG      540

CGGATAGCCA TGACCTATGA GCGCATCCTC TACATCAGCC TGGAGATGCT GGTGTGCGC      600

ATCCACCCCA TTCCTGGAGA GTACAAGTTC TTCTGGACGG CACGCCTGGC CTTCTCCTA      660

ACCCCCTCTC GGGCAGAGGC TGACGTGGAC ATTATTCTGT CCATCCCCAT GTTCTTGCG      720

CTATACCTGA TCGCCCGAGT CATGCTGCTA CATAGCAAGC TCTTCACGGA TGCCTCATC      780

CGAAGCATCG GGCCCTCAA CAAGATCAAC TTCAACACCC GATTCGTCAT GAAGACGCT      840

ATGACCATCT GCCCGGGCAC GGTGCTGCTA ATGTTCAGCA TCTCTCTGTG GATCATCGC      900

GCCTGGACTG TGAGAGTCTG TGAAAGGTAC CATGACCAGC AGGACGTAAC TAGTAACTT      960

CTGGGTGCCA TGTGGCTCAT CTCCATCACG TTCCTTTCCA TTGGCTATGG GGACATGG      1020

CCCCACACAT ACTGTGGGAA AGGTGTCTGT CTTCTCACTG GCATCATGGG TGCAGGCT      1080
```

```
ACTGCCCTCG TGGTAGCTGT GGTTGCCCGG AAGCTCGAAC TCACCAAAGC AGAGAAGC      1140

GTGCACAACT TCATGATGGA CACTCAGCTC ACCAAACGGA TCAAGAACGC TGCCGCCA      1200

GTCCTCCGGG AAACATGGCT GATCTACAAA CACACAAAGC TGCTAAAGAA GATTGACC      1260

GCCAAAGTCA GGAAACACCA GAGGAAGTTC CTCCAAGCTA TTCACCAACT GAGGGGTG      1320

AAGATGGAAC AAAGGAAGCT GAGTGACCAA GCCAACACCC TGGTGGACCT TTCCAAGA      1380

CAGAACGTCA TGTATGACTT GATCACGGAG CTCAACGACC GGAGTGAAGA CCTGGAAA      1440

CAGATTGGCA GCCTGGAATC CAAGCTGGAG CACCTCACAG CCAGCTTCAA TTCCCTGC      1500

CTGCTCATCG CAGACACCCT GCGCCAACAG CAGCAGCAGC TGCTCACTGC CTTCGTGG      1560

GCCCGGGGCA TCAGTGTGGC TGTGGGAACT AGCCACGCCC CTCCCTCTGA CAGCCCTA      1620

GGGATCAGCT CCACCTCTTT CCCGGAATTC CTAATATTC                           1659
```

(2) INFORMATION FOR SEQ ID NO: 17:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 17:

```
Leu Ser Asp Tyr Ala Leu Ile Phe Gly Met
1               5                   10
```

(2) INFORMATION FOR SEQ ID NO: 18:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 18:

```
Gln Arg Lys Phe Leu Gln Ala Ile His Gln
1               5                   10
```

(2) INFORMATION FOR SEQ ID NO: 19:

(i) SEQUENCE CHARACTERISTICS:
        (A) LENGTH: 579 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Protein
        (B) LOCATION: 1..579
        (D) OTHER INFORMATION: /note= "human small conductance,
            calcium-activated potassium channel
            protein 2 (hSK2)"

(ix) FEATURE:
        (A) NAME/KEY: Region
        (B) LOCATION: 134..461
        (D) OTHER INFORMATION: /note= "core region of hSK2"

(xi) SEQUENCE DESCRIPTION: SEQ ID NO: 19:

Met Ser Ser Cys Arg Tyr Asn Gly Gly Val Met Arg Pro Leu Ser As

```
1               5                  10                 15
Leu Ser Ala Ser Arg Arg Asn Leu His Glu Met Asp Ser Glu Ala Gl
            20                 25                 30

Pro Leu Gln Pro Pro Ala Ser Val Gly Gly Gly Gly Ala Ser Se
            35                 40             45

Pro Ser Ala Ala Ala Ala Ala Ala Ala Val Ser Ser Ala Pr
            50                 55             60

Glu Ile Val Val Ser Lys Pro Glu His Asn Asn Ser Asn Asn Leu Al
65                  70                 75                 80

Leu Tyr Gly Thr Gly Gly Gly Ser Thr Gly Gly Gly Gly Gl
                85                 90                 95

Gly Gly Ser Gly His Gly Ser Ser Gly Thr Lys Ser Ser Ly
            100                105                110

Lys Asn Gln Asn Ile Gly Tyr Lys Leu Gly His Arg Ala Leu Ph
            115                120            125

Glu Lys Arg Lys Arg Leu Ser Asp Tyr Ala Leu Ile Phe Gly Met Ph
            130                135            140

Gly Ile Val Val Met Val Ile Glu Thr Glu Leu Ser Trp Gly Ala Ty
145                150                155                160

Asp Lys Ala Ser Leu Tyr Ser Leu Ala Leu Lys Cys Leu Ile Ser Le
                165                170                175

Ser Thr Ile Ile Leu Leu Gly Leu Ile Ile Val Tyr His Ala Arg Gl
                180                185            190

Ile Gln Leu Phe Met Val Asp Asn Gly Ala Asp Trp Arg Ile Al
            195                200            205

Met Thr Tyr Glu Arg Ile Phe Phe Ile Cys Leu Glu Ile Leu Val Cy
            210                215            220

Ala Ile His Pro Ile Pro Gly Asn Tyr Thr Phe Thr Trp Thr Ala Ar
225                230            235                240

Leu Ala Phe Ser Tyr Ala Pro Ser Thr Thr Ala Asp Val Asp Il
                245                250                255

Ile Leu Ser Ile Pro Met Phe Leu Arg Leu Tyr Leu Ile Ala Arg Va
                260                265            270

Met Leu Leu His Ser Lys Leu Phe Thr Asp Ala Ser Ser Arg Ser Il
            275                280            285

Gly Ala Leu Asn Lys Ile Asn Phe Asn Thr Arg Phe Val Met Lys Th
            290                295            300

Leu Met Thr Ile Cys Pro Gly Thr Val Leu Leu Val Phe Ser Ile Se
305                310                315                320

Leu Trp Ile Ile Ala Ala Trp Thr Val Arg Ala Cys Glu Arg Tyr Hi
                325                330            335

Asp Gln Gln Asp Val Thr Ser Asn Phe Leu Gly Ala Met Trp Leu Il
            340                345            350

Ser Ile Thr Phe Leu Ser Ile Gly Tyr Gly Asp Met Val Pro Asn Th
            355                360            365

Tyr Cys Gly Lys Gly Val Cys Leu Leu Thr Gly Ile Met Gly Ala Gl
    370                375            380

Cys Thr Ala Leu Val Val Ala Val Val Ala Arg Lys Leu Glu Leu Th
385                390                395                400

Lys Ala Glu Lys His Val His Asn Phe Met Met Asp Thr Gln Leu Th
            405                410                415

Lys Arg Val Lys Asn Ala Ala Ala Asn Val Leu Arg Glu Thr Trp Le
            420                425            430
```

```
Ile Tyr Lys Asn Thr Lys Leu Val Lys Lys Ile Asp His Ala Lys Va
            435                 440                 445

Arg Lys His Gln Arg Lys Phe Leu Gln Ala Ile His Gln Leu Arg Se
        450                 455                 460

Val Lys Met Glu Gln Arg Lys Leu Asn Asp Gln Ala Asn Thr Leu Va
465                 470                 475                 480

Asp Leu Ala Lys Thr Gln Asn Ile Met Tyr Asp Met Ile Ser Asp Le
                485                 490                 495

Asn Glu Arg Ser Glu Asp Phe Glu Lys Arg Ile Val Thr Leu Glu Th
            500                 505                 510

Lys Leu Glu Thr Leu Ile Gly Ser Ile His Ala Leu Pro Gly Leu Il
            515                 520                 525

Ser Gln Thr Ile Arg Gln Gln Arg Asp Phe Ile Glu Ala Gln Me
        530                 535                 540

Glu Ser Tyr Asp Lys His Val Thr Tyr Asn Ala Glu Arg Ser Arg Se
545                 550                 555                 560

Ser Ser Arg Arg Arg Ser Ser Thr Ala Pro Pro Thr Ser Se
                565                 570                 575

Glu Ser Ser
```

(2) INFORMATION FOR SEQ ID NO: 20:

(i) SEQUENCE CHARACTERISTICS:
        (A) LENGTH: 557 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Protein
        (B) LOCATION: 1..557
        (D) OTHER INFORMATION: /note= "N-terminally truncated form
            of human small conductance,
            calcium-activated potassium channel
            protein 3 (hSK3)"

(ix) FEATURE:
        (A) NAME/KEY: Region
        (B) LOCATION: 109..436
        (D) OTHER INFORMATION: /note= "core region of hSK3"

(xi) SEQUENCE DESCRIPTION: SEQ ID NO: 20:

```
Met Ser Ser Cys Lys Tyr Ser Gly Gly Val Met Lys Pro Leu Ser Ar
1               5                   10                  15

Leu Ser Ala Ser Arg Arg Asn Leu Ile Glu Ala Glu Thr Glu Gly Gl
            20                  25                  30

Pro Leu Gln Leu Phe Ser Pro Ser Asn Pro Pro Glu Ile Val Ile Se
            35                  40                  45

Ser Arg Glu Asp Asn His Ala His Gln Thr Leu Leu His His Pro As
        50                  55                  60

Ala Thr His Asn His Gln His Ala Gly Thr Thr Ala Ser Ser Thr Th
65                  70                  75                  80

Phe Pro Lys Ala Asn Lys Arg Lys Asn Gln Asn Ile Gly Tyr Lys Le
                85                  90                  95

Gly His Arg Arg Ala Leu Phe Glu Lys Arg Lys Arg Leu Ser Asp Ty
            100                 105                 110

Ala Leu Ile Phe Gly Met Phe Gly Ile Val Val Met Val Ile Glu Th
            115                 120                 125
```

-continued

```
Glu Leu Ser Trp Gly Leu Tyr Ser Lys Asp Ser Met Phe Ser Leu Al
    130                 135                 140
Leu Lys Cys Leu Ile Ser Leu Ser Thr Ile Ile Leu Leu Gly Leu Il
145                 150                 155                 160
Ile Ala Tyr His Thr Arg Glu Val Gln Leu Phe Val Ile Asp Asn Gl
                165                 170                 175
Ala Asp Asp Trp Arg Ile Ala Met Thr Tyr Glu Arg Ile Leu Tyr Il
            180                 185                 190
Ser Leu Glu Met Leu Val Cys Ala Ile His Pro Ile Pro Gly Glu Ty
        195                 200                 205
Lys Phe Phe Trp Thr Ala Arg Leu Ala Phe Ser Tyr Thr Pro Ser Ar
    210                 215                 220
Ala Glu Ala Asp Val Asp Ile Ile Leu Ser Ile Pro Met Phe Leu Ar
225                 230                 235                 240
Leu Tyr Leu Ile Ala Arg Val Met Leu Leu His Ser Lys Leu Phe Th
                245                 250                 255
Asp Ala Ser Ser Arg Ser Ile Gly Ala Leu Asn Lys Ile Asn Phe As
            260                 265                 270
Thr Arg Phe Val Met Lys Thr Leu Met Thr Ile Cys Pro Gly Thr Va
        275                 280                 285
Leu Leu Val Phe Ser Ile Ser Leu Trp Ile Ile Ala Ala Trp Thr Va
    290                 295                 300
Arg Val Cys Glu Arg Tyr His Asp Gln Gln Asp Val Thr Ser Asn Ph
305                 310                 315                 320
Leu Gly Ala Met Trp Leu Ile Ser Ile Thr Phe Leu Ser Ile Gly Ty
                325                 330                 335
Gly Asp Met Val Pro His Thr Tyr Cys Gly Lys Gly Val Cys Leu Le
            340                 345                 350
Thr Gly Ile Met Gly Ala Gly Cys Thr Ala Leu Val Val Ala Val Va
        355                 360                 365
Ala Arg Lys Leu Glu Leu Thr Lys Ala Glu Lys His Val His Asn Ph
    370                 375                 380
Met Met Asp Thr Gln Leu Thr Lys Arg Ile Lys Asn Ala Ala Ala As
385                 390                 395                 400
Val Leu Arg Glu Thr Trp Leu Ile Tyr Lys His Thr Lys Leu Leu Ly
                405                 410                 415
Lys Ile Asp His Ala Lys Val Arg Lys His Gln Arg Lys Phe Leu Gl
            420                 425                 430
Ala Ile His Gln Leu Arg Ser Val Lys Met Glu Gln Arg Lys Leu Se
        435                 440                 445
Asp Gln Ala Asn Thr Leu Val Asp Leu Ser Lys Met Gln Asn Val Me
    450                 455                 460
Tyr Asp Leu Ile Thr Glu Leu Asn Asp Arg Ser Glu Asp Leu Glu Ly
465                 470                 475                 480
Gln Ile Gly Ser Leu Glu Ser Lys Leu Glu His Leu Thr Ala Ser Ph
                485                 490                 495
Asn Ser Leu Pro Leu Leu Ile Ala Asp Thr Leu Arg Gln Gln Gln Gl
            500                 505                 510
Gln Leu Leu Ser Ala Ile Ile Glu Ala Arg Gly Val Ser Val Ala Va
        515                 520                 525
Gly Thr Thr His Thr Pro Ile Ser Asp Ser Pro Ile Gly Val Ser Se
    530                 535                 540
```

```
Thr Ser Phe Pro Thr Pro Tyr Thr Ser Ser Ser Cys
545                 550                 555
```

(2) INFORMATION FOR SEQ ID NO: 21:

(i) SEQUENCE CHARACTERISTICS:
        (A) LENGTH: 1740 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1740
        (D) OTHER INFORMATION: /note= "human small conductance,
            calcium-activated potassium channel
            protein 2 (hSK2) cDNA"

(xi) SEQUENCE DESCRIPTION: SEQ ID NO: 21:

```
ATGAGCAGCT GCAGGTACAA CGGGGGCGTC ATGCGGCCGC TCAGCAACTT GAGCGCGTCC      60

CGCCGGAACC TGCACGAGAT GGACTCAGAG GCGCAGCCCC TGCAGCCCCC CGCGTCTGT      120

GGAGGAGGTG GCGGCGCGTC CTCCCCGTCT GCAGCCGCTG CCGCCGCCGC CGCTGTTTC      180

TCCTCAGCCC CCGAGATCGT GGTGTCTAAG CCCGAGCACA ACAACTCCAA CAACCTGGC      240

CTCTATGGAA CCGGCGGCGG AGGCAGCACT GGAGGAGGCG GCGGCGGTGG CGGGAGCGG      300

CACGGCAGCA GCAGTGGCAC CAAGTCCAGC AAAAAGAAAA ACCAGAACAT CGGCTACAA      360

CTGGGCCACC GGCGCGCCCT GTTCGAAAAG CGCAAGCGGC TCAGCGACTA CGCGCTCAT      420

TTCGGCATGT TCGGCATCGT GGTCATGGTC ATCGAGACCG AGCTGTCGTG GGGCGCCTA      480

GACAAGGCGT CGCTGTATTC CTTAGCTCTG AAATGCCTTA TCAGTCTCTC CACGATCAT      540

CTGCTCGGTC TGATCATCGT GTACCACGCC AGGGAAATAC AGTTGTTCAT GGTGGACAA      600

GGAGCAGATG ACTGGAGAAT AGCCATGACT TATGAGCGTA TTTTCTTCAT CTGCTTGGA      660

ATACTGGTGT GTGCTATTCA TCCCATACCT GGGAATTATA CATTCACATG GACGGCCCG      720

CTTGCCTTCT CCTATGCCCC ATCCACAACC ACCGCTGATG TGGATATTAT TTTATCTAT      780

CCAATGTTCT TAAGACTCTA TCTGATTGCC AGAGTCATGC TTTTACATAG CAAACTTTT      840

ACTGATGCCT CCTCTAGAAG CATTGGAGCA CTTAATAAGA TAAACTTCAA TACACGTTT      900

GTTATGAAGA CTTTAATGAC TATATGCCCA GGAACTGTAC TCTTGGTTTT TAGTATCTC      960

TTATGGATAA TTGCCGCATG GACTGTCCGA GCTTGTGAAA GGTACCATGA TCAACAGG      1020

GTTACTAGCA ACTTCCTTGG AGCGATGTGG TTGATATCAA TAACTTTTCT CTCCATTG      1080

TATGGTGACA TGGTACCTAA CACATACTGT GGAAAAGGAG TCTGCTTACT TACTGGAA      1140

ATGGGTGCTG GTTGCACAGC CCTGGTGGTA GCTGTAGTGG CAAGGAAGCT AGAACTTA      1200

AAAGCAGAAA AACACGTGCA CAATTTCATG ATGGATACTC AGCTGACTAA AAGAGTAA      1260

AATGCAGCTG CCAATGTACT CAGGGAAACA TGGCTAATTT ACAAAAATAC AAAGCTAG      1320

AAAAAGATAG ATCATGCAAA AGTAAGAAAA CATCAACGAA AATTCCTGCA AGCTATTC      1380

CAATTAAGAA GTGTAAAAAT GGAACAGAGG AAACTGAATG ACCAAGCAAA CACTTTGG      1440

GACTTGGCAA AGACCCAGAA CATCATGTAT GATATGATTT CTGACTTAAA CGAAAGGA      1500

GAAGACTTCG AGAAGAGGAT TGTTACCCTG GAAACAAAAT TAGAGACTTT GATTGGTA      1560

ATCCACGCCC TCCCTGGGCT CATAAGCCAG ACCATCAGGC AGCAGCAGAG AGATTTCA      1620

GAGGCTCAGA TGGAGAGCTA CGACAAGCAC GTCACTTACA ATGCTGAGCG GTCCCGGT      1680
```

```
TCGTCCAGGA GGCGGCGGTC CTCTTCCACA GCACCACCAA CTTCATCAGA GAGTAGCT       1740
```

(2) INFORMATION FOR SEQ ID NO: 22:

(i) SEQUENCE CHARACTERISTICS:
        (A) LENGTH: 1674 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1674
        (D) OTHER INFORMATION: /note= "N-terminally truncated cDNA
            for human small conductance,
            calcium-activated potassium channel
            protein 3 (hSK3)"

(xi) SEQUENCE DESCRIPTION: SEQ ID NO: 22:

```
ATGAGCTCCT GCAAGTATAG CGGTGGGGTC ATGAAGCCCC TCAGCCGCCT CAGCGCCTCC       60
CGGAGGAACC TCATCGAGGC CGAGACTGAG GGCCAACCCC TCCAGCTTTT CAGCCCTAG       120
AACCCCCCGG AGATCGTCAT CTCCTCCCGG AGGACAACC ATGCCCACCA GACCCTGCT       180
CATCACCCTA TGCCACCCA CAACCACCAG CATGCCGGCA CCACCGCCAG CAGCACCAC       240
TTCCCCAAAG CCAACAAGCG GAAAAACCAA AACATTGGCT ATAAGCTGGG ACACAGGAG       300
GCCCTGTTTG AAAAGAGAAA GCGACTGAGT GACTATGCTC TGATTTTTGG GATGTTTGG       360
ATTGTTGTTA TGGTGATAGA GACCGAGCTC TCTTGGGGTT TGTACTCAAA GGACTCCAT       420
TTTTCGTTGG CCCTGAAATG CCTTATCAGT CTGTCCACCA TCATCCTTTT GGGCTTGAT       480
ATCGCCTACC ACACACGTGA AGTCCAGCTC TTCGTGATCG ACAACGGCGC GGATGACTG       540
CGGATAGCCA TGACCTACGA GCGCATCCTC TACATCAGCC TGGAGATGCT GGTGTGCGC       600
ATCCACCCCA TTCCTGGCGA GTACAAGTTC TTCTGGACGG CACGCCTGGC CTTCTCCTA       660
ACACCCTCCC GGGCGGAGGC CGATGTGGAC ATCATCCTGT CTATCCCCAT GTTCCTGCG       720
CTGTACCTGA TCGCCCGAGT CATGCTGCTG CACAGCAAGC TCTTCACCGA TGCCTCGTC       780
CGCAGCATCG GGGCCCTCAA CAAGATCAAC TTCAACACCC GCTTTGTCAT GAAGACGCT       840
ATGACCATCT GCCCTGGCAC TGTGCTGCTC GTGTTCAGCA TCTCTCTGTG GATCATTGC       900
GCCTGGACCG TCCGTGTCTG TGAAAGGTAC CATGACCAGC AGGACGTAAC TAGTAACTT       960
CTGGGTGCCA TGTGGCTCAT CTCCATCACA TTCCTTTCCA TTGGTTATGG GGACATGG      1020
CCCCACACAT ACTGTGGGAA AGGTGTCTGT CTCCTCACTG GCATCATGGG TGCAGGCT      1080
ACTGCCCTTG TGGTGGCCGT GGTGGCCCGA AAGCTGGAAC TCACCAAAGC GGAGAAGC      1140
GTTCATAACT TCATGATGGA CACTCAGCTC ACCAAGCGGA TCAAGAATGC TGCAGCCA      1200
GTCCTTCGGG AAACATGGTT AATCTATAAA CACACAAAGC TGCTAAAGAA GATTGACC      1260
GCCAAAGTGA GGAAACACCA GAGGAAGTTC CTCCAAGCTA TCCACCAGTT GAGGAGCG      1320
AAGATGGAAC AGAGGAAGCT GAGTGACCAA GCCAACACTC TGGTGGACCT TTCCAAGA      1380
CAGAATGTCA TGTATGACTT AATCACAGAA CTCAATGACC GGAGCGAAGA CCTGGAGA      1440
CAGATTGGCA GCCTGGAGTC GAAGCTGGAG CATCTCACCG CCAGCTTCAA CTCCCTGC      1500
CTGCTCATCG CCGACACCCT GCGCCAGCAG CAGCAGCAGC TCCTGTCTGC CATCATCG      1560
GCCCGGGGTG TCAGCGTGGC AGTGGGCACC ACCCACACCC CAATCTCCGA TAGCCCCA      1620
GGGGTCAGCT CCACCTCCTT CCCGACCCCG TACACAAGTT CAAGCAGTTG CTAA          1674
```

(2) INFORMATION FOR SEQ ID NO: 23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

ATGAGCAGCT GCAGGTACAA CG                              22

(2) INFORMATION FOR SEQ ID NO: 24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

CTAGCTACTC TCTGATGAAG TTG                             23

(2) INFORMATION FOR SEQ ID NO: 25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

ATGAGCTCCT GCAAGTATAG C                               21

(2) INFORMATION FOR SEQ ID NO: 26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

TTAGCAACTG CTTGAACTTG TG                              22

(2) INFORMATION FOR SEQ ID NO: 27:

(i) SEQUENCE CHARACTERISTICS:
        (A) LENGTH: 328 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Region
        (B) LOCATION: 1..328
        (D) OTHER INFORMATION: /note= "core region of hSK1 from
            amino acid positions 124 through 451"

(xi) SEQUENCE DESCRIPTION: SEQ ID NO: 27:

-continued

```
Leu Ser Asp Tyr Ala Leu Ile Phe Gly Met Phe Gly Ile Val Val Me
1               5                  10                 15

Val Thr Glu Thr Glu Leu Ser Trp Gly Val Tyr Thr Lys Glu Ser Le
                20                  25                 30

Tyr Ser Phe Ala Leu Lys Cys Leu Ile Ser Leu Ser Thr Ala Ile Le
            35                  40                  45

Leu Gly Leu Val Val Leu Tyr His Ala Arg Glu Ile Gln Leu Phe Me
        50                  55                  60

Val Asp Asn Gly Ala Asp Asp Trp Arg Ile Ala Met Thr Cys Glu Ar
65                  70                  75                  80

Val Phe Leu Ile Ser Leu Glu Leu Ala Val Cys Ala Ile His Pro Va
                85                  90                  95

Pro Gly His Tyr Arg Phe Thr Trp Thr Ala Arg Leu Ala Phe Thr Ty
            100                 105                 110

Ala Pro Ser Val Ala Glu Ala Asp Val Asp Val Leu Leu Ser Ile Pr
            115                 120                 125

Met Phe Leu Arg Leu Tyr Leu Leu Gly Arg Val Met Leu Leu His Se
        130                 135                 140

Lys Ile Phe Thr Asp Ala Ser Ser Arg Ser Ile Gly Ala Leu Asn Ly
145                 150                 155                 160

Ile Thr Phe Asn Thr Arg Phe Val Met Lys Thr Leu Met Thr Ile Cy
                165                 170                 175

Pro Gly Thr Val Leu Leu Val Phe Ser Ile Ser Ser Trp Ile Ile Al
            180                 185                 190

Ala Trp Thr Val Arg Val Cys Glu Arg Tyr His Asp Lys Gln Glu Va
            195                 200                 205

Thr Ser Asn Phe Leu Gly Ala Met Trp Leu Ile Ser Ile Thr Phe Le
        210                 215                 220

Ser Ile Gly Tyr Gly Asp Met Val Pro His Thr Tyr Cys Gly Lys Gl
225                 230                 235                 240

Val Cys Leu Leu Thr Gly Ile Met Gly Ala Gly Cys Thr Ala Leu Va
                245                 250                 255

Val Ala Val Val Ala Arg Lys Leu Glu Leu Thr Lys Ala Glu Lys Hi
            260                 265                 270

Val His Asn Phe Met Met Asp Thr Gln Leu Thr Lys Arg Val Lys As
            275                 280                 285

Ala Ala Ala Asn Val Leu Arg Glu Thr Trp Leu Ile Tyr Lys His Th
        290                 295                 300

Arg Leu Val Lys Lys Pro Asp Gln Ala Arg Val Arg Lys His Gln Ar
305                 310                 315                 320

Lys Phe Leu Gln Ala Ile His Gln
            325
```

(2) INFORMATION FOR SEQ ID NO: 28:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 28:

```
Gly His Arg Arg Ala Leu Phe Glu Lys Arg Lys Arg Leu Ser Asp Ty
1               5                   10                  15
```

(2) INFORMATION FOR SEQ ID NO: 29:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

```
Phe Thr Asp Ala Ser Ser Arg Ser Ile Gly Ala Leu
1               5                   10
```

(2) INFORMATION FOR SEQ ID NO: 30:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 30:

```
Ala Arg Lys Leu Glu Leu Thr Lys Ala Glu Lys His Val His Asn Ph
1               5                   10                  15
Met Met Asp Thr Gln Leu Thr Lys Arg
                20                  25
```

(2) INFORMATION FOR SEQ ID NO: 31:

(i) SEQUENCE CHARACTERISTICS:
        (A) LENGTH: 1287 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1287
        (D) OTHER INFORMATION: /note= "human intermediate
            conductance, calcium-activated
            potassium channel protein 1
            (hIK1) cDNA"

(xi) SEQUENCE DESCRIPTION: SEQ ID NO: 31:

```
ATGGGCGGGG ATCTGGTGCT TGGCCTGGGG GCCTTGAGAC GCCGAAAGCG CTTGCTGGAG      60

CAGGAGAAGT CTCTGGCCGG CTGGGCACTG GTGCTGGCAG GAACTGGCAT TGGACTCAT     120

GTGCTGCATG CAGAGATGCT GTGGTTCGGG GGGTGCTCGT GGGCGCTCTA CCTGTTCCT     180

GTTAAATGCA CGATCAGCAT TTCCACCTTC TTACTCCTCT GCCTCATCGT GGCCTTTCA     240

GCCAAAGAGG TCCAGCTGTT CAGTACCGAC AACGGGCTGC GGGACTGGCG CGTGGTGCT     300

CTGACCGGGC GGCAGGCGGC GCAGATCGTG CTGGAGCTGG TGGTGTGTGG GCTGCACCC     360

GCGCCCGTGC GGGGCCCGCC GTGCGTGCAG GATTTAGGGG CGCCGCTGAC CTCCCCGCA     420

CCCTGGCCGG GATTCCTGGG CCAAGGGGAA GCGCTGCTGT CCCTGGCCAT GCTGCTGCG     480

CTCTACCTGG TGCCCCGCGC CGTGCTCCTG CGCAGCGGCG TCCTGCTCAA CGCTTCCTA     540

CGCAGCATCG GCGCTCTCAA TCAAGTCCGC TTCCGCCACT GGTTCGTGGC CAAGCTTTA     600

ATGAACACGC ACCCTGGCCG CCTGCTGCTC GGCCTCACGC TTGGCCTCTG GCTGACCAC     660

GCCTGGGTGC TGTCCGTGGC CGAGAGGCAG GCTGTTAATG CCACTGGGCA CCTTTCAGA     720
```

-continued

```
ACACTTTGGC TGATCCCCAT CACATTCCTG ACCATCGGCT ATGGTGACGT GGTGCCGGG      780

ACCATGTTGG GCAAGATCGT CTGCCTGTGC ACTGGAGTCA TGGGTGTCTG CTGCACAGC      840

CTGCTGGTGG CCGTGGTGGC CCGGAAGCTG GAGTTTAACA AGGCAGAGAA GCACGTGCA      900

AACTTCATGA TGGATATCCA GAATACCAAA GAGATGAAGG AGTCCGCTGC CCGAGTGCT      960

CAAGAAGCCT GGATGTTCTA CAAACATACT CGCAGGAAGG AGTCTCATGC TGCCCGCA     1020

CATCAGCGCA AGCTGCTGGC CGCCATCAAC GCGTTCCGCC AGGTGCGGCT GAAACACC     1080

AAGCTCCGGG AACAAGTGAA CTCCATGGTG GACATCTCCA AGATGCACAT GATCCTGT     1140

GACCTGCAGC AGAATCTGAG CAGCTCACAC CGGGCCCTGG AGAAACAGAT TGACACGC     1200

GCGGGGAAGC TGGATGCCCT GACTGAGCTG CTTAGCACTG CCCTGGGGCC GAGGCAGC     1260

CCAGAACCCA GCCAGCAGTC CAAGTAG                                        1287
```

(2) INFORMATION FOR SEQ ID NO: 32:

(i) SEQUENCE CHARACTERISTICS:
        (A) LENGTH: 428 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Protein
        (B) LOCATION: 1..428
        (D) OTHER INFORMATION: /note= "human intermediate
            conductance, calcium-activated potassium
            channel protein 1 (hIK1)"

(ix) FEATURE:
        (A) NAME/KEY: Region
        (B) LOCATION: 25..351
        (D) OTHER INFORMATION: /note= "core region of hIK1"

(xi) SEQUENCE DESCRIPTION: SEQ ID NO: 32:

```
Met Gly Gly Asp Leu Val Leu Gly Leu Gly Ala Leu Arg Arg Ly
1               5                   10                  15

Arg Leu Leu Glu Gln Glu Lys Ser Leu Ala Gly Trp Ala Leu Val Le
                20                  25                  30

Ala Gly Thr Gly Ile Gly Leu Met Val Leu His Ala Glu Met Leu Tr
            35                  40                  45

Phe Gly Gly Cys Ser Trp Ala Leu Tyr Leu Phe Leu Val Lys Cys Th
        50                  55                  60

Ile Ser Ile Ser Thr Phe Leu Leu Cys Leu Ile Val Ala Phe Hi
65                  70                  75                  80

Ala Lys Glu Val Gln Leu Phe Ser Thr Asp Asn Gly Leu Arg Asp Tr
                85                  90                  95

Arg Val Val Leu Leu Thr Gly Arg Gln Ala Ala Gln Ile Val Leu Gl
                100                 105                 110

Leu Val Val Cys Gly Leu His Pro Ala Pro Val Arg Gly Pro Pro Cy
            115                 120                 125

Val Gln Asp Leu Gly Ala Pro Leu Thr Ser Pro Gln Pro Trp Pro Gl
        130                 135                 140

Phe Leu Gly Gln Gly Glu Ala Leu Leu Ser Ala Met Leu Leu Ar
145                 150                 155                 160

Leu Tyr Leu Val Pro Arg Ala Val Leu Leu Arg Ser Gly Val Leu Le
                165                 170                 175
```

```
Asn Ala Ser Tyr Arg Ser Ile Gly Ala Leu Asn Gln Val Arg Phe Ar
            180                 185                 190

His Trp Phe Val Ala Lys Leu Tyr Met Asn Thr His Pro Gly Arg Le
            195                 200                 205

Leu Leu Gly Leu Thr Leu Gly Leu Trp Leu Thr Thr Ala Trp Val Le
            210                 215                 220

Ser Val Ala Glu Arg Gln Ala Val Asn Ala Thr Gly His Leu Ser As
225                 230                 235                 240

Thr Leu Trp Leu Ile Pro Ile Thr Phe Leu Thr Ile Gly Tyr Gly As
                245                 250                 255

Val Val Pro Gly Thr Met Leu Gly Lys Ile Val Cys Leu Cys Thr Gl
                260                 265                 270

Val Met Gly Val Cys Cys Thr Ala Leu Leu Val Ala Val Val Ala Ar
            275                 280                 285

Lys Leu Glu Phe Asn Lys Ala Glu Lys His Val His Asn Phe Met Me
            290                 295                 300

Asp Ile Gln Asn Thr Lys Glu Met Lys Glu Ser Ala Ala Arg Val Le
305                 310                 315                 320

Gln Glu Ala Trp Met Phe Tyr Lys His Thr Arg Arg Lys Glu Ser Hi
                325                 330                 335

Ala Ala Arg Arg His Gln Arg Lys Leu Leu Ala Ala Ile Asn Ala Ph
            340                 345                 350

Arg Gln Val Arg Leu Lys His Arg Lys Leu Arg Glu Gln Val Asn Se
            355                 360                 365

Met Val Asp Ile Ser Lys Met His Met Ile Leu Tyr Asp Leu Gln Gl
            370                 375                 380

Asn Leu Ser Ser Ser His Arg Ala Leu Glu Lys Gln Ile Asp Thr Le
385                 390                 395                 400

Ala Gly Lys Leu Asp Ala Leu Thr Glu Leu Leu Ser Thr Ala Leu Gl
                405                 410                 415

Pro Arg Gln Leu Pro Glu Pro Ser Gln Gln Ser Lys
            420                 425
```

(2) INFORMATION FOR SEQ ID NO: 33:

(i) SEQUENCE CHARACTERISTICS:
        (A) LENGTH: 30 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 33:

```
Val Arg Gly Pro Pro Cys Val Gln Asp Leu Gly Ala Pro Leu Thr Se
1               5                   10                  15

Pro Gln Pro Trp Pro Gly Phe Leu Gly Gln Gly Glu Ala Leu
                20                  25                  30
```

(2) INFORMATION FOR SEQ ID NO: 34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:

```
GCCGTGCGTG CAGGATTTAG G                                              21

(2) INFORMATION FOR SEQ ID NO: 35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 35:

CCAGAGGCCA AGCGTGAGGC C                                              21

(2) INFORMATION FOR SEQ ID NO: 36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 36:

TCCAAGATGC ACATGATCCT G                                              21

(2) INFORMATION FOR SEQ ID NO: 37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 37:

GGACTGCTGG CTGGGTTCTG G                                              21

(2) INFORMATION FOR SEQ ID NO: 38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 38:

ATGGGCGGGG ATCTGGTGCT TG                                             22

(2) INFORMATION FOR SEQ ID NO: 39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 39:

CTACTTGGAC TGCTGGCTGG GTTC                                           24
```

-continued (2) INFORMATION FOR SEQ ID NO: 40:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 40:

ATGGGCGGGG ATCTGGTGCT TGG                     23

(2) INFORMATION FOR SEQ ID NO: 41:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 41:

GGGTCCAGCT ACTTGGACTG CTG                     23

(2) INFORMATION FOR SEQ ID NO: 42:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 42:

Ala Arg Lys Leu Glu Leu Thr Lys Ala Glu Lys His Val His Asn Ph
1              5                  10               15

Met Met Asp Thr Gln Leu Thr Lys
            20

(2) INFORMATION FOR SEQ ID NO: 43:

(i) SEQUENCE CHARACTERISTICS:
        (A) LENGTH: 732 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Protein
        (B) LOCATION: 1..732
        (D) OTHER INFORMATION: /note= "full-length rat small
            conductance, calcium-activated potassium
            channel protein 3 (rSK3)"

(xi) SEQUENCE DESCRIPTION: SEQ ID NO: 43:

Met Asp Thr Ser Gly His Phe His Glu Ser Gly Val Gly Asp Leu As
1              5                  10               15

Glu Asp Pro Lys Cys Pro Cys Pro Ser Ser Gly Asp Glu Gln Gln Gl
            20                  25                  30

Gln Gln Gln Pro Pro Pro Ser Ala Pro Pro Ala Val Pro Gln Gl
        35                  40                45

Pro Pro Gly Pro Leu Leu Gln Pro Gln Pro Gln Leu Gln Gln Gl
    50                  55                60

```
Gln Gln Gln Gln Gln Gln Gln Gln Gln Gln Gln Gln Gln Gln Gl
 65                  70                  75                  80

Ala Pro Leu His Pro Leu Pro Gln Leu Ala Gln Leu Gln Ser Gln Va
                 85                  90                  95

Val His Pro Gly Leu Leu His Ser Ser Pro Thr Ala Phe Arg Ala Pr
            100                 105                 110

Asn Ser Ala Asn Ser Thr Ala Ile Leu His Pro Ser Ser Arg Gln Gl
            115                 120                 125

Ser Gln Leu Asn Leu Asn Asp His Leu Val Gly His Ser Pro Ser Se
        130                 135                 140

Thr Ala Thr Ser Gly Pro Gly Gly Ser Arg His Arg Gln Ala Se
145                 150                 155                 160

Pro Val Val His Arg Arg Asp Ser Asn Pro Phe Thr Glu Ile Ala Me
                165                 170                 175

Ser Ser Cys Lys Tyr Ser Gly Gly Val Met Lys Pro Leu Ser Arg Le
            180                 185                 190

Ser Ala Ser Arg Arg Asn Leu Ile Glu Ala Glu Pro Glu Gly Gln Pr
        195                 200                 205

Leu Gln Leu Phe Ser Pro Ser Asn Pro Pro Glu Ile Ile Ser Se
210                 215                 220

Arg Glu Asp Asn His Ala His Gln Thr Leu Leu His His Pro Asn Al
225                 230                 235                 240

Thr His Asn His Gln His Ala Gly Thr Thr Ala Gly Ser Thr Thr Ph
                245                 250                 255

Pro Lys Ala Asn Lys Arg Lys Asn Gln Asn Ile Gly Tyr Lys Leu Gl
            260                 265                 270

His Arg Arg Ala Leu Phe Glu Lys Arg Lys Arg Leu Ser Asp Tyr Al
        275                 280                 285

Leu Ile Phe Gly Met Phe Gly Ile Val Val Met Val Ile Glu Thr Gl
290                 295                 300

Leu Ser Trp Gly Leu Tyr Ser Lys Asp Ser Met Phe Ser Leu Ala Le
305                 310                 315                 320

Lys Cys Leu Ile Ser Leu Ser Thr Ile Ile Leu Leu Gly Leu Ile Il
                325                 330                 335

Ala Tyr His Thr Arg Glu Val Gln Leu Phe Val Ile Asp Asn Gly Al
            340                 345                 350

Asp Asp Trp Arg Ile Ala Met Thr Tyr Glu Arg Ile Leu Tyr Ile Se
        355                 360                 365

Leu Glu Met Leu Val Cys Ala Ile His Pro Ile Pro Gly Glu Tyr Ly
370                 375                 380

Phe Phe Trp Thr Ala Arg Leu Ala Phe Ser Tyr Thr Pro Ser Arg Al
385                 390                 395                 400

Glu Ala Asp Val Asp Ile Ile Leu Ser Ile Pro Met Phe Leu Arg Le
                405                 410                 415

Tyr Leu Ile Ala Arg Val Met Leu Leu His Ser Lys Leu Phe Thr As
            420                 425                 430

Ala Ser Ser Arg Ser Ile Gly Ala Leu Asn Lys Ile Asn Phe Asn Th
        435                 440                 445

Arg Phe Val Met Lys Thr Leu Met Thr Ile Cys Pro Gly Thr Val Le
450                 455                 460

Leu Met Phe Ser Ile Ser Leu Trp Ile Ile Ala Ala Trp Thr Val Ar
465                 470                 475                 480
```

```
Val Cys Glu Arg Tyr His Asp Gln Gln Asp Val Thr Ser Asn Phe Le
                485                 490                 495

Gly Ala Met Trp Leu Ile Ser Ile Thr Phe Leu Ser Ile Gly Tyr Gl
                500                 505                 510

Asp Met Val Pro His Thr Tyr Cys Gly Lys Gly Val Cys Leu Leu Th
                515                 520                 525

Gly Ile Met Gly Ala Gly Cys Thr Ala Leu Val Ala Val Val Al
                530                 535             540

Arg Lys Leu Glu Leu Thr Lys Ala Glu Lys His Val His Asn Phe Me
545                 550                 555                 560

Met Asp Thr Gln Leu Thr Lys Arg Ile Lys Asn Ala Ala Ala Asn Va
                565                 570                 575

Leu Arg Glu Thr Trp Leu Ile Tyr Lys His Thr Lys Leu Leu Lys Ly
                580                 585                 590

Ile Asp His Ala Lys Val Arg Lys His Gln Arg Lys Phe Leu Gln Al
                595                 600                 605

Ile His Gln Leu Arg Gly Val Lys Met Glu Gln Arg Lys Leu Ser As
            610                 615                 620

Gln Ala Asn Thr Leu Val Asp Leu Ser Lys Met Gln Asn Val Met Ty
625                 630                 635                 640

Asp Leu Ile Thr Glu Leu Asn Asp Arg Ser Glu Asp Leu Glu Lys Gl
                645                 650                 655

Ile Gly Ser Leu Glu Ser Lys Leu Glu His Leu Thr Ala Ser Phe As
                660                 665                 670

Ser Leu Pro Leu Leu Ile Ala Asp Thr Leu Arg Gln Gln Gln Gln Gl
            675                 680                 685

Leu Leu Thr Ala Phe Val Glu Ala Arg Gly Ile Ser Val Ala Val Gl
            690                 695                 700

Thr Ser His Ala Pro Pro Ser Asp Ser Pro Ile Gly Ile Ser Ser Th
705                 710                 715                 720

Ser Phe Pro Thr Pro Tyr Thr Ser Ser Ser Cys
                725                 730

(2) INFORMATION FOR SEQ ID NO: 44:

(i) SEQUENCE CHARACTERISTICS:
        (A) LENGTH: 2224 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..2224
        (D) OTHER INFORMATION: /note= "rat small conductance,
            calcium-activated potassium channel
            protein 3 (rSK3) full-length cDNA"

(xi) SEQUENCE DESCRIPTION: SEQ ID NO: 44:

CATGGACACT TCTGGGCACT TCCATGAGTC GGGGGTGGGG GATCTGGATG AAGACCCCAA      60

GTGTCCCTGT CCATCTTCTG GGACGAGCA ACAGCAGCAA CAGCAACCGC CACCACCGT     120

AGCGCCACCA GCAGTCCCCC AGCAGCCTCC GGGACCCTTG CTGCAGCCTC AGCCTCCGC     180

GCTTCAGCAG CAGCAGCAGC AGCAGCAGCA GCAGCAGCAG CAGCAGCAGC AGCAGCAGC     240

GGCTCCACTG CACCCCCTGC CTCAGCTTGC CCAACTCCAG AGCCAGGTTG TCCATCCTG     300

TCTGTTGCAC TCTTCTCCCA CGGCTTTCAG GGCTCCCAAT TCAGCCAACT CCACCGCCA     360
```

| | |
|---|---|
| CCTCCACCCT TCCTCCAGGC AAGGCAGCCA GCTAAATCTC AATGACCACT TGGTTGGCC | 420 |
| CTCTCCAAGT TCCACAGCCA CAAGTGGGCC TGGTGGAGGC AGCCGGCACC GGCAGGCCA | 480 |
| CCCCGTGGTG CACCGGCGGG ACAGCAATCC CTTCACGGAG ATAGCTATGA GCTCCTGCA | 540 |
| ATACAGCGGT GGGGTCATGA AGCCCCTCAG CCGCCTCAGC GCCTCTCGGA GAAACCTTA | 600 |
| CGAGGCCGAG CCTGAGGGCC AACCCCTCCA GCTCTTCAGT CCCAGCAACC CCCCAGAGA | 660 |
| TATCATCTCC TCCAGGGAGG ATAACCATGC CCACCAGACT CTGCTCCATC ACCCCAACG | 720 |
| TACCCACAAC CACCAGCATG CCGGCACCAC TGCTGGCAGC ACCACCTTCC CCAAAGCCA | 780 |
| CAAGCGGAAA AACCAAAACA TTGGCTATAA GCTGGGCAC AGGAGGGCCC TGTTTGAAA | 840 |
| GAGAAAGCGA CTGAGTGACT ATGCTCTGAT TTTTGGGATG TTTGGAATTG TTGTTATGG | 900 |
| GATAGAGACC GAACTGTCTT GGGGTTTGTA CTCAAAGGAT TCCATGTTTT CGTTGGCCC | 960 |
| GAAATGCCTT ATCAGTTTAT CCACCATCAT CCTGCTTGGT TTGATCATCG CCTACCAC | 1020 |
| AAGGGAAGTA CAGCTCTTTG TGATCGACAA TGGTGCAGAT GACTGGCGGA TAGCCATG | 1080 |
| CTATGAGCGC ATCCTCTACA TCAGCCTGGA GATGCTGGTG TGCGCCATCC ACCCCATT | 1140 |
| TGGAGAGTAC AAGTTCTTCT GGACGGCACG CCTGGCCTTC TCCTACACCC CCTCTCGG | 1200 |
| AGAGGCTGAC GTGGACATTA TTCTGTCCAT CCCCATGTTC TTGCGCCTAT ACCTGATC | 1260 |
| CCGAGTCATG CTGCTACATA GCAAGCTCTT CACGGATGCC TCATCCCGAA GCATCGGG | 1320 |
| CCTCAACAAG ATCAACTTCA ACACCCGATT CGTCATGAAG ACGCTCATGA CCATCTGC | 1380 |
| GGGCACGGTG CTGCTAATGT TCAGCATCTC TCTGTGGATC ATCGCTGCCT GGACTGTG | 1440 |
| AGTCTGTGAA AGGTACCATG ACCAGCAGGA CGTAACTAGT AACTTTCTGG GTGCCATG | 1500 |
| GCTCATCTCC ATCACGTTCC TTTCCATTGG CTATGGGGAC ATGGTGCCCC ACACATAC | 1560 |
| TGGGAAAGGT GTCTGTCTTC TCACTGGCAT CATGGGTGCA GGCTGCACTG CCCTCGTG | 1620 |
| AGCTGTGGTT GCCCGGAAGC TCGAACTCAC CAAAGCAGAG AAGCATGTGC ACAACTTC | 1680 |
| GATGGACACT CAGCTCACCA AACGGATCAA GAACGCTGCC GCCAATGTCC TCCGGGAA | 1740 |
| ATGGCTGATC TACAAACACA CAAAGCTGCT AAAGAAGATT GACCACGCCA AAGTCAGG | 1800 |
| ACACCAGAGG AAGTTCCTCC AAGCTATTCA CCAACTGAGG GGTGTCAAGA TGGAACAA | 1860 |
| GAAGCTGAGT GACCAAGCCA ACACCCTGGT GGACCTTTCC AAGATGCAGA ACGTCATG | 1920 |
| TGACTTGATC ACGGAGCTCA ACGACCGGAG TGAAGACCTG GAAAAGCAGA TTGGCAGC | 1980 |
| GGAATCCAAG CTGGAGCACC TCACAGCCAG CTTCAATTCC CTGCCCCTGC TCATCGCA | 2040 |
| CACCCTGCGC CAACAGCAGC AGCAGCTGCT CACTGCCTTC GTGGAGGCCC GGGGCATC | 2100 |
| TGTGGCTGTG GGAACTAGCC ACGCCCCTCC CTCTGACAGC CCTATCGGGA TCAGCTCC | 2160 |
| CTCTTTCCCA ACCCCATACA CAAGTTCAAG CAGTTGCTAA ATAAAACTCC CCACTCCA | 2220 |
| AGCA | 2224 |

(2) INFORMATION FOR SEQ ID NO: 45:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 45:

Phe Xaa Ser Ile Pro Xaa Xaa Xaa Trp Trp Ala Xaa Val Thr Met Th

```
                1               5              10              15

Thr Val Gly Tyr Gly Asp Met Xaa Pro
                20              25

(2) INFORMATION FOR SEQ ID NO: 46:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /note= "Xaa = Ser or Thr"

(xi) SEQUENCE DESCRIPTION: SEQ ID NO: 46:

Asn Xaa Xaa Xaa
1

(2) INFORMATION FOR SEQ ID NO: 47:

(i) SEQUENCE CHARACTERISTICS:
        (A) LENGTH: 736 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Protein
        (B) LOCATION: 1..736
        (D) OTHER INFORMATION: /note= "full length human small
            conductance, calcium-activated
            potassium channel protein 3 (hSK3)"

(xi) SEQUENCE DESCRIPTION: SEQ ID NO: 47:

Met Asp Thr Ser Gly His Phe His Asp Ser Gly Val Gly Asp Leu As
1               5              10              15

Glu Asp Pro Lys Cys Pro Cys Pro Ser Ser Gly Asp Glu Gln Gln Gl
                20              25              30

Gln Gln Gln Gln Gln Gln Gln Gln Gln Pro Pro Pro Ala Pro Pr
            35              40              45

Ala Ala Pro Gln Gln Pro Leu Gly Pro Ser Leu Gln Pro Gln Pro Pr
        50              55              60

Gln Leu Gln Gln Gln Gln Gln Gln Gln Gln Gln Gln Gln Gln Gl
65              70              75              80

Gln Gln Gln Gln Gln Pro Pro His Pro Leu Ser Gln Leu Ala Gln Le
            85              90              95

Gln Ser Gln Pro Val His Pro Gly Leu Leu His Ser Ser Pro Thr Al
            100             105             110

Phe Arg Ala Pro Pro Ser Ser Asn Ser Thr Ala Ile Leu His Pro Se
        115             120             125

Ser Arg Gln Gly Ser Gln Leu Asn Leu Asn Asp His Leu Leu Gly Hi
        130             135             140

Ser Pro Ser Ser Thr Ala Thr Ser Gly Pro Gly Gly Ser Arg Hi
145             150             155             160

Arg Gln Ala Ser Pro Leu Val His Arg Arg Asp Ser Asn Pro Ser Th
            165             170             175
```

-continued

```
Glu Ile Ala Met Ser Ser Cys Lys Tyr Ser Gly Gly Val Met Lys Pr
                180                 185                 190
Leu Ser Arg Leu Ser Ala Ser Arg Arg Asn Leu Ile Glu Ala Glu Th
            195                 200                 205
Glu Gly Gln Pro Leu Gln Leu Phe Ser Pro Ser Asn Pro Pro Glu Il
        210                 215                 220
Val Ile Ser Ser Arg Glu Asp Asn His Ala His Gln Thr Leu Leu Hi
225                 230                 235                 240
His Pro Asn Ala Thr His Asn His Gln His Ala Gly Thr Thr Ala Se
                245                 250                 255
Ser Thr Thr Phe Pro Lys Ala Asn Lys Arg Lys Asn Gln Asn Ile Gl
            260                 265                 270
Tyr Lys Leu Gly His Arg Arg Ala Leu Phe Glu Lys Arg Lys Arg Le
        275                 280                 285
Ser Asp Tyr Ala Leu Ile Phe Gly Met Phe Gly Ile Val Val Met Va
    290                 295                 300
Ile Glu Thr Glu Leu Ser Trp Gly Leu Tyr Ser Lys Asp Ser Met Ph
305                 310                 315                 320
Ser Leu Ala Leu Lys Cys Leu Ile Ser Leu Ser Thr Ile Ile Leu Le
                325                 330                 335
Gly Leu Ile Ile Ala Tyr His Thr Arg Glu Val Gln Leu Phe Val Il
            340                 345                 350
Asp Asn Gly Ala Asp Asp Trp Arg Ile Ala Met Thr Tyr Glu Arg Il
        355                 360                 365
Leu Tyr Ile Ser Leu Glu Met Leu Val Cys Ala Ile His Pro Ile Pr
    370                 375                 380
Gly Glu Tyr Lys Phe Phe Trp Thr Ala Arg Leu Ala Phe Ser Tyr Th
385                 390                 395                 400
Pro Ser Arg Ala Glu Ala Asp Val Asp Ile Ile Leu Ser Ile Pro Me
                405                 410                 415
Phe Leu Arg Leu Tyr Leu Ile Ala Arg Val Met Leu Leu His Ser Ly
            420                 425                 430
Leu Phe Thr Asp Ala Ser Ser Arg Ser Ile Gly Ala Leu Asn Lys Il
        435                 440                 445
Asn Phe Asn Thr Arg Phe Val Met Lys Thr Leu Met Thr Ile Cys Pr
    450                 455                 460
Gly Thr Val Leu Leu Val Phe Ser Ile Ser Leu Trp Ile Ile Ala Al
465                 470                 475                 480
Trp Thr Val Arg Val Cys Glu Arg Tyr His Asp Gln Gln Asp Val Th
                485                 490                 495
Ser Asn Phe Leu Gly Ala Met Trp Leu Ile Ser Ile Thr Phe Leu Se
            500                 505                 510
Ile Gly Tyr Gly Asp Met Val Pro His Thr Tyr Cys Gly Lys Gly Va
        515                 520                 525
Cys Leu Leu Thr Gly Ile Met Gly Ala Gly Cys Thr Ala Leu Val Va
    530                 535                 540
Ala Val Val Ala Arg Lys Leu Glu Leu Thr Lys Ala Glu Lys His Va
545                 550                 555                 560
His Asn Phe Met Met Asp Thr Gln Leu Thr Lys Arg Ile Lys Asn Al
                565                 570                 575
Ala Ala Asn Val Leu Arg Glu Thr Trp Leu Ile Tyr Lys His Thr Ly
            580                 585                 590
```

```
Leu Leu Lys Lys Ile Asp His Ala Lys Val Arg Lys His Gln Arg Ly
            595                 600                 605

Phe Leu Gln Ala Ile His Gln Leu Arg Ser Val Lys Met Glu Gln Ar
        610                 615                 620

Lys Leu Ser Asp Gln Ala Asn Thr Leu Val Asp Leu Ser Lys Met Gl
625                 630                 635                 640

Asn Val Met Tyr Asp Leu Ile Thr Glu Leu Asn Asp Arg Ser Glu As
                645                 650                 655

Leu Glu Lys Gln Ile Gly Ser Leu Glu Ser Lys Leu Glu His Leu Th
            660                 665                 670

Ala Ser Phe Asn Ser Leu Pro Leu Leu Ile Ala Asp Thr Leu Arg Gl
        675                 680                 685

Gln Gln Gln Gln Leu Leu Ser Ala Ile Ile Glu Ala Arg Gly Val Se
        690                 695                 700

Val Ala Val Gly Thr Thr His Thr Pro Ile Ser Asp Ser Pro Ile Gl
705                 710                 715                 720

Val Ser Ser Thr Ser Phe Pro Thr Pro Tyr Thr Ser Ser Ser Cy
                725                 730                 735

(2) INFORMATION FOR SEQ ID NO: 48:

(i) SEQUENCE CHARACTERISTICS:
        (A) LENGTH: 2462 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..2462
        (D) OTHER INFORMATION: /note= "human small conductance,
            calcium-activated potassium channel
            protein 3 (hSK3) full length cDNA"

(xi) SEQUENCE DESCRIPTION: SEQ ID NO: 48:

AGTTCTTTCA CCCCCTCTTC TTTCTCCAAG CTCCCCTCCT GCTCTCCCTC CCTGCCCAAT    60

ACAATGCATT CTTGAGTGGC AGCGTCTGGA CTCCAGGCAG CCCCAGAGAA CCGAAGCAA    120

CCAAAGAGAG GACTGGAGCC AAGATACTGG TGGGGGAGAT GGATGCCTG GCTTTCTTT    180

AGGACATCTT TGGAGCGAGG GTGGCTTTGG GGTGGGGGCT TGTGCTGCAG GGAATACAG    240

CAGGCCCCAA GATGGACACT TCTGGGCACT TCCATGACTC GGGGGTGGGG GACTTGGAT    300

AAGACCCCAA GTGCCCCTGT CCATCCTCTG GGGATGAGCA GCAGCAGCAG CAGCAGCAG    360

AACAGCAGCA GCAGCCACCA CCGCCAGCGC CACCAGCAGC CCCCAGCAG CCCCTGGGA    420

CCTCGCTGCA GCCTCAGCCT CCGCAGCTTC AGCAGCAGCA GCAGCAGCAG CAGCAGCAG    480

AGCAGCAGCA GCAGCAGCAG CAGCAGCCAC CGCATCCCCT GTCTCAGCTC GCCCAACTC    540

AGAGCCAGCC CGTCCACCCT GGCCTGCTGC ACTCCTCTCC CACCGCTTTC AGGGCCCCC    600

CTTCGTCCAA CTCCACCGCC ATCCTCCACC CTTCCTCCAG GCAAGGCAGC CAGCTCAAT    660

TCAATGACCA CTTGCTTGGC CACTCTCCAA GTTCCACAGC TACAAGTGGG CCTGGCGGA    720

GCAGCCGGCA CCGACAGGCC AGCCCCCTGG TGCACCGGCG GGACAGCAAC CCCTCCACG    780

AGATCGCCAT GAGCTCCTGC AAGTATAGCG GTGGGGTCAT GAAGCCCCTC AGCCGCCTC    840

GCGCCTCCCG GAGGAACCTC ATCGAGGCCG AGACTGAGGG CCAACCCCTC AGCTTTTTC    900

GCCCTAGCAA CCCCCCGGAG ATCGTCATCT CCTCCCGGGA GGACAACCAT GCCCACCAG    960
```

```
CCCTGCTCCA TCACCCTAAT GCCACCCACA ACCACCAGCA TGCCGGCACC ACCGCCAG        1020

GCACCACCTT CCCCAAAGCC AACAAGCGGA AAAACCAAAA CATTGGCTAT AAGCTGGG        1080

ACAGGAGGGC CCTGTTTGAA AAGAGAAAGC GACTGAGTGA CTATGCTCTG ATTTTTGG        1140

TGTTTGGAAT TGTTGTTATG GTGATAGAGA CCGAGCTCTC TTGGGGTTTG TACTCAAA        1200

ACTCCATGTT TTCGTTGGCC CTGAAATGCC TTATCAGTCT GTCCACCATC ATCCTTTT        1260

GCTTGATCAT CGCCTACCAC ACACGTGAAG TCCAGCTCTT CGTGATCGAC AACGGCGC        1320

ATGACTGGCG GATAGCCATG ACCTACGAGC GCATCCTCTA CATCAGCCTG GAGATGCT        1380

TGTGCGCCAT CCACCCCATT CCTGGCGAGT ACAAGTTCTT CTGGACGGCA CGCCTGGC        1440

TCTCCTACAC ACCCTCCCGG GCGGAGGCCG ATGTGGACAT CATCCTGTCT ATCCCCAT        1500

TCCTGCGCCT GTACCTGATC GCCCGAGTCA TGCTGCTGCA CAGCAAGCTC TTCACCGA        1560

CCTCGTCCCG CAGCATCGGG GCCCTCAACA AGATCAACTT CAACACCCGC TTTGTCAT        1620

AGACGCTCAT GACCATCTGC CCTGGCACTG TGCTGCTCGT GTTCAGCATC TCTCTGTG        1680

TCATTGCTGC CTGGACCGTC CGTGTCTGTG AAAGGTACCA TGACCAGCAG GACGTAAC        1740

GTAACTTTCT GGGTGCCATG TGGCTCATCT CCATCACATT CCTTTCCATT GGTTATGG        1800

ACATGGTGCC CCACACATAC TGTGGGAAAG GTGTCTGTCT CCTCACTGGC ATCATGGG        1860

CAGGCTGCAC TGCCCTTGTG GTGGCCGTGG TGGCCCGAAA GCTGGAACTC ACCAAAGC        1920

AGAAGCACGT TCATAACTTC ATGATGGACA CTCAGCTCAC CAAGCGGATC AAGAATGC        1980

CAGCCAATGT CCTTCGGGAA ACATGGTTAA TCTATAAACA CACAAAGCTG CTAAAGAA        2040

TTGACCATGC CAAAGTGAGG AAACACCAGA GGAAGTTCCT CCAAGCTATC CACCAGTT        2100

GGAGCGTCAA GATGGAACAG AGGAAGCTGA GTGACCAAGC CAACACTCTG GTGGACCT        2160

CCAAGATGCA GAATGTCATG TATGACTTAA TCACAGAACT CAATGACCGG AGCGAAGA        2220

TGGAGAAGCA GATTGGCAGC CTGGAGTCGA AGCTGGAGCA TCTCACCGCC AGCTTCAA        2280

CCCTGCCGCT GCTCATCGCC GACACCCTGC GCCAGCAGCA GCAGCAGCTC CTGTCTGC        2340

TCATCGAGGC CCGGGGTGTC AGCGTGGCAG TGGGCACCAC CCACACCCCA ATCTCCGA        2400

GCCCCATTGG GGTCAGCTCC ACCTCCTTCC CGACCCCGTA CACAAGTTCA AGCAGTTG        2460

AA                                                                    2462
```